(12) United States Patent
Donnelly et al.

(10) Patent No.: US 11,123,316 B2
(45) Date of Patent: *Sep. 21, 2021

(54) IMAGING COMPOSITION AND USES THEREOF

(71) Applicant: The University of Melbourne, Melbourne (AU)

(72) Inventors: Paul Stephen Donnelly, Brunswick East (AU); Stacey Erin Rudd, Melbourne (AU); Spencer John Williams, Coburg (AU)

(73) Assignee: The University of Melbourne, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,215

(22) Filed: Apr. 8, 2020

(65) Prior Publication Data

US 2020/0246286 A1 Aug. 6, 2020

Related U.S. Application Data

(63) Continuation of application No. 16/511,577, filed on Jul. 15, 2019, now Pat. No. 10,653,649, which is a continuation of application No. 15/963,599, filed on Apr. 26, 2018, now Pat. No. 10,398,660, which is a continuation of application No. 15/518,333, filed as application No. PCT/AU2015/050640 on Oct. 16, 2015, now Pat. No. 9,980,930.

(30) Foreign Application Priority Data

Oct. 16, 2014 (AU) .................... 2014904138

(51) Int. Cl.

| A61K 31/18 | (2006.01) |
|---|---|
| C07K 17/06 | (2006.01) |
| A61K 51/10 | (2006.01) |
| C07C 259/06 | (2006.01) |
| C07C 309/14 | (2006.01) |
| C07C 311/19 | (2006.01) |
| C07C 311/29 | (2006.01) |
| C07C 311/42 | (2006.01) |
| C07C 311/46 | (2006.01) |
| C07C 323/60 | (2006.01) |
| C07D 207/48 | (2006.01) |
| C07D 211/60 | (2006.01) |
| C07D 211/96 | (2006.01) |
| C07D 213/42 | (2006.01) |
| C07D 213/74 | (2006.01) |
| C07D 213/89 | (2006.01) |
| C07D 215/36 | (2006.01) |
| C07D 223/06 | (2006.01) |
| C07D 277/06 | (2006.01) |
| C07D 277/80 | (2006.01) |
| C07D 279/12 | (2006.01) |
| C07D 295/13 | (2006.01) |
| C07D 309/06 | (2006.01) |
| C07D 401/12 | (2006.01) |
| C07D 405/12 | (2006.01) |
| C07D 413/12 | (2006.01) |
| C07D 453/06 | (2006.01) |
| C07D 471/08 | (2006.01) |
| C07D 487/08 | (2006.01) |

(52) U.S. Cl.
CPC .......... *A61K 31/18* (2013.01); *A61K 51/1051* (2013.01); *C07C 259/06* (2013.01); *C07C 309/14* (2013.01); *C07C 311/19* (2013.01); *C07C 311/29* (2013.01); *C07C 311/42* (2013.01); *C07C 311/46* (2013.01); *C07C 323/60* (2013.01); *C07D 207/48* (2013.01); *C07D 211/60* (2013.01); *C07D 211/96* (2013.01); *C07D 213/42* (2013.01); *C07D 213/74* (2013.01); *C07D 213/89* (2013.01); *C07D 215/36* (2013.01); *C07D 223/06* (2013.01); *C07D 277/06* (2013.01); *C07D 277/80* (2013.01); *C07D 279/12* (2013.01); *C07D 295/13* (2013.01); *C07D 309/06* (2013.01); *C07D 401/12* (2013.01); *C07D 405/12* (2013.01); *C07D 413/12* (2013.01); *C07D 453/06* (2013.01); *C07D 471/08* (2013.01); *C07D 487/08* (2013.01); *C07K 17/06* (2013.01); *C07C 2601/04* (2017.05)

(58) Field of Classification Search
None
See application file for complete search history.

(56) References Cited

U.S. PATENT DOCUMENTS

| 6,656,876 B1 | 12/2003 | Aberg |
|---|---|---|
| 9,980,930 B2 | 5/2018 | Donnelly et al. |
| 10,398,660 B2 | 9/2019 | Donnelly et al. |

(Continued)

OTHER PUBLICATIONS

Perk, L.R. et al "p-Isothiocyanatobenzyl-desferroixamine: a new bifunctional chelate for facile radiolabeling of monoclonal antibodies with zirconium-89 for immuno-PET imaging", Eur J. Nucl. Med. Mol. Imaging, 2010, vol. 37, p. 250-259.

Tinianow, J. N. et al "Site-specifically 89Zr-labaled monoclonal antibodies for ImmunoPET", Nuclear Medicine and Biology, 2010, vol. 37, p. 289-297.

Verel, I. et al. "$^{89}$Zr Immuno-PET: Comprehensive Procedures for the Production of $^{89}$Zr-Labeled Monoclonal Antibodies", The Journal of Nuclear Medicine, 2003, vol. 44, No. 8, p. 1271-1281.

(Continued)

*Primary Examiner* — Brian J Davis
(74) *Attorney, Agent, or Firm* — Cooley LLP; Matthew Pavao

(57) ABSTRACT

The invention discussed in this application relates to hydroxamic acid-based compounds that are useful as imaging agents when bound to an appropriate metal centre, particularly for the imaging of tumours.

17 Claims, 57 Drawing Sheets

(56) References Cited

U.S. PATENT DOCUMENTS

| | | |
|---|---|---|
| 10,653,649 B2 * | 5/2020 | Donnelly .............. C07C 311/46 |
| 2011/0200533 A1 | 8/2011 | Port et al. |
| 2020/0009090 A1 | 1/2020 | Donnelly et al. |

OTHER PUBLICATIONS

Yoganathan et al. "Chemical synthesis and biological evaluation of gallidermin-siderophore conjugates", Organic & Biomolecular Chemistry, 2011, vol. 9, No. 7, p. 2133-2141.

Zeglis B. et al. "Modular Strategy for the Construction of Radiometalated Antibodies for Positron Emission Tomography Based on Inverse Electron Demand Diets—Alder Click Chemistry", Bioconjugate Chemistry, 2011, vol. 22, p. 2048-2059.

* cited by examiner

Retention time (min)

1 hr reaction time 1.5 hr reaction time 2 hr reaction time

Retention time (min)

Retention time (min)

IMAGING COMPOSITION AND USES THEREOF

CROSS-REFERENCE TO RELATED APPLICATIONS

This application is a Continuation of U.S. patent application Ser. No. 16/511,577, filed Jul. 15, 2019, which is a Continuation of U.S. patent application Ser. No. 15/963,599, filed Apr. 26, 2018, now U.S. Pat. No. 10,398,660 issued on Sep. 3, 2019, which is a Continuation of U.S. patent application Ser. No. 15/518,333, filed Apr. 11, 2017, now U.S. Pat. No. 9,980,930, issued on May 29, 2018 and is a National Stage Application, filed under 35 U.S.C. 371, of International Application No. PCT/AU2015/050640, filed on Oct. 16, 2015, which claims priority to, and the benefit of, AU Application No. 2014904138, filed Oct. 16, 2014. The contents of each of these applications are incorporated by reference in their entirety.

FIELD OF THE INVENTION

The present invention relates to hydroxamic acid-based compounds that are useful as imaging agents when bound to an appropriate metal centre, particularly for the imaging of tumours. The present invention also relates to compositions including the compounds, and to methods of imaging patients using the compounds.

BACKGROUND OF THE INVENTION

Zirconium-89 ($^{89}$Zr) is a positron-emitting radionuclide that is used in medical imaging applications. In particular, it is used in positron emission tomography (PET) for cancer detection and imaging. It has a longer half-life ($t_{1/2}$=79.3 hours) than other radionuclides used for medical imaging, such as $^{18}$F. For example, $^{18}$F has a $t_{1/2}$ of 110 minutes, which means that its use requires close proximity to a cyclotron facility and rapid and high-yielding synthesis techniques for the preparation of the agents into which it is incorporated. $^{89}$Zr is not plagued by these same problems, which makes $^{89}$Zr particularly attractive for use in medical imaging applications.

Desferrioxamine (DFO) is a bacterial siderophore that has been used since the late 1960s to treat iron overload. The three hydroxamic acid groups in DFO form co-ordination bonds with $Fe^{3+}$ ions, essentially making DFO a hexadentate ligand that chelates the $Fe^{3+}$ ions. Due to the co-ordination geometry of $^{89}$Zr, DFO has also been used as a chelator for $^{89}$Zr in PET imaging applications (Holland, J. P. et al (2012) Nature 10:1586).

Other DFO-based radioisotope chelators have also been prepared for use in PET imaging applications. These include N-succinyl-desferrioxamine-tetrafluorophenol ester (N-suc-DFO-TFP ester) p-isothiocyanatobenzyl-desferrioxamine (DFO-Bz-NCS, also known as DFO-Ph-NCS) and desferrioxamine-maleimide (DFO-maleimide). All of these chelators can be conjugated with antibodies or antibody fragments to provide a means of targeting the imaging agent to the tumour to be imaged.

However, these chelators suffer from a number of disadvantages. The synthesis of N-suc-DFO-TFP ester involves the addition of $Fe^{3+}$, to prevent the reaction of the tetrafluorophenol ester with one of the hydroxamate groups of desferrioxamine (DFO). Upon completion of the synthesis (which includes the step of coupling N-suc-DFO-TFP ester to an antibody), the $Fe^{3+}$ then needs to be removed. This is achieved using a 100-fold molar excess of EDTA at a pH of 4.2-4.5. These conditions can be detrimental to pH-sensitive antibodies.

With regard to DFO-Bz-NCS, if this compound is added to an antibody solution too quickly without shaking or proper mixing, DFO-Bz-NCS causes the formation of antibody aggregates. In addition, the stability of the radiolabelled and antibody-conjugated chelators is a concern when stored for extended periods of time, and buffers containing chloride ions need to be avoided as they result in detachment of the radionuclide from the complex.

DFO-maleimide conjugates to antibodies via Michael addition to thiol groups. There are two main issues with this. The first is that Michael additions to thiols can lead to mixtures of isomers. This is a disadvantage because the isomers may interact in different ways with biological systems. The second issue is that Michael addition to thiol groups is reversible. This increases the risk that the DFO-maleimide-radionulide complex will dissociate from the antibody, resulting in distribution of the complex throughout the body. This not only decreases the imaging selectivity but also increases the likelihood of toxic side effects as the radiation emitted from the radionuclide in the complex interacts with other organs.

Therefore, there is a need to develop new agents for use with radioisotopes, which do not have these drawbacks.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present inventors have found that the compound of formula (I) set out below (also referred to herein as "DFO-squaramide" or "DFOSq"), and its conjugate with a biological molecule (when complexed to a radionuclide such as $^{89}$Zr), is an effective PET imaging agent:

(I)

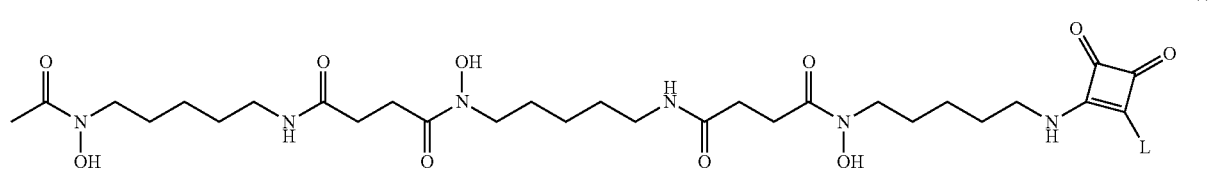

wherein L is a leaving group. In one embodiment, L is OR. R may be selected from $C_1$ to $C_{10}$ alkyl, $C_1$ to $C_{10}$ heteroalkyl, $C_2$ to $C_{10}$ alkene, $C_2$ to $C_{10}$ alkyne, and aryl, each of which is optionally substituted. R may be $C_1$ to $C_{10}$ alkyl (e.g. $C_1$ to $C_6$ alkyl, such as methyl, ethyl, propyl or butyl). R may be methyl or ethyl. R may be ethyl.

Therefore, in one aspect, the present invention relates to a compound of formula (I), as defined above, or a pharmaceutically acceptable salt thereof.

In another aspect, the present invention relates to a radionuclide complex of a compound of formula (I):

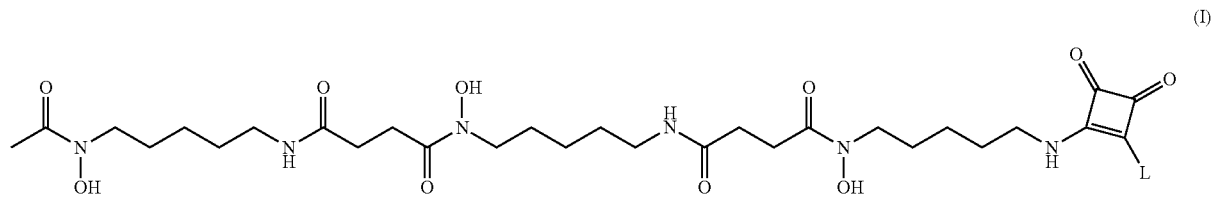

(I)

or a pharmaceutically acceptable salt thereof, wherein L is a leaving group. L may be OR. R may be selected from $C_1$ to $C_{10}$ alkyl, $C_1$ to $C_{10}$ heteroalkyl, $C_2$ to $C_{10}$ alkene, $C_2$ to $C_{10}$ alkyne, and aryl, each of which is optionally substituted. R may be alkyl (e.g. $C_1$ to $C_6$ alkyl, such as methyl, ethyl, propyl or butyl). R may be methyl or ethyl. R may be ethyl.

The radionuclide may be a radioisotope of zirconium, gallium or indium. The radioisotope of zirconium may be $^{89}$Zr. The radioisotope of gallium may be $^{68}$Ga. The radioisotope of indium may be $^{111}$In. The radionuclide may be a radioisotope of zirconium (e.g. $^{89}$Zr).

In another aspect, the present invention also relates to a conjugate of:
a compound of formula (I):

The target molecule may be a polypeptide (such as a transfer protein or an antibody). The target molecule may be a peptide (such as a targeting peptide). The polypeptide may be an antibody. The antibody may be selected from Herceptin (trastuzumab), rituximab and cetuximab.

The radionuclide may be a radioisotope of zirconium, gallium or indium. The radioisotope of zirconium may be $^{89}$Zr. The radioisotope of gallium may be $^{68}$Ga. The radioisotope of indium may be $^{111}$In. The radionuclide may be an isotope of zirconium (e.g. $^{89}$Zr).

The radionuclide-labelled complex and the radionuclide-labelled conjugate have improved affinity when compared with DFO-Ph-NCS or a conjugate of DFO-Ph-NCS and the target molecule.

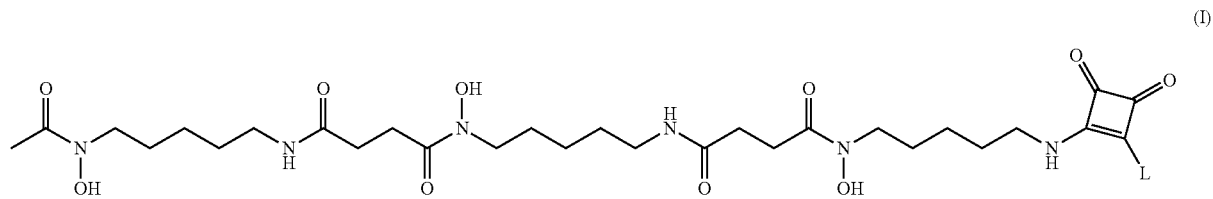

(I)

or a pharmaceutically-acceptable salt thereof, wherein L is a leaving group (as defined herein), and
a target molecule.

The target molecule may be a polypeptide (such as a transfer protein or an antibody). The target molecule may be a peptide (such as a targeting peptide). The polypeptide may be an antibody. The antibody may be selected from Herceptin (trastuzumab), rituximab and cetuximab.

In another aspect, the present invention relates to a radionuclide-labelled conjugate of:
a compound of formula (I):

In another aspect, the present invention relates to a method of imaging a patient, the method including:
administering to a patient a radionuclide-labelled conjugate, as defined above, and
imaging the patient.

In another aspect, the present invention relates to a method of imaging a cell or in vitro biopsy sample, the method including:
administering to a cell or in vitro biopsy sample a radionuclide-labelled conjugate, as defined above, and
imaging the cell or in vitro biopsy sample.

(I)

or a pharmaceutically-acceptable salt thereof, wherein L is a leaving group (as defined herein),
a target molecule, and
a radionuclide complexed thereto.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 21B: radiation signal (mV); $^{89}$Zr-DFOSq-trastuzumab elutes at ~12 mins, gentisate elutes at 20-25 mins).

FIG. 34A shows iTLC analysis of $^{89}$Zr-DFOPhNCS-trastuzumab reaction mixture after 1 hr, showing ~30% labelling efficiency (origin is at 60 mm, solvent front at 150 mm; labelled trastuzumab remains at the origin, activity with a distance of >70 mm (r.f.>0.1) represents non-chelated $^{89}$Zr). FIG. 34B shows iTLC analysis of $^{89}$Zr-DFOPhNCS-trastuzumab reaction mixture after 1.5 hr, showing ~50% labelling efficiency (origin is at 55 mm, solvent front at 135 mm; Labelled trastuzumab remains at the origin, activity with a distance of >65 mm (r.f.>0.1) represents non-chelated $^{89}$Zr). FIG. 34C shows iTLC analysis of $^{89}$Zr-DFOPhNCS-trastuzumab reaction mixture after 2 hr, showing ~65% labelling efficiency (origin is at 60 mm, solvent front at 145 mm; labelled trastuzumab remains at the origin, activity with a distance of >70 mm (r.f.>0.1) represents non-chelated $^{89}$Zr).

FIG. 36B: radiation signal (mV); $^{89}$Zr-DFOPhNCS-trastuzumab begins to elute at ~12 mins, gentisic acic elutes at 20-25 mins).

FIG. 39A: absorbance at 280/254 nm; FIG. 39B: radiation.

FIG. 40A: absorbance at 254; FIG. 40B: absorbance at 280 nm; FIG. 40C: radiation.

FIG. 41A: absorbance at 280/254 nm; FIG. 41B: radiation.

DETAILED DESCRIPTION OF THE EMBODIMENTS

Figure 1:
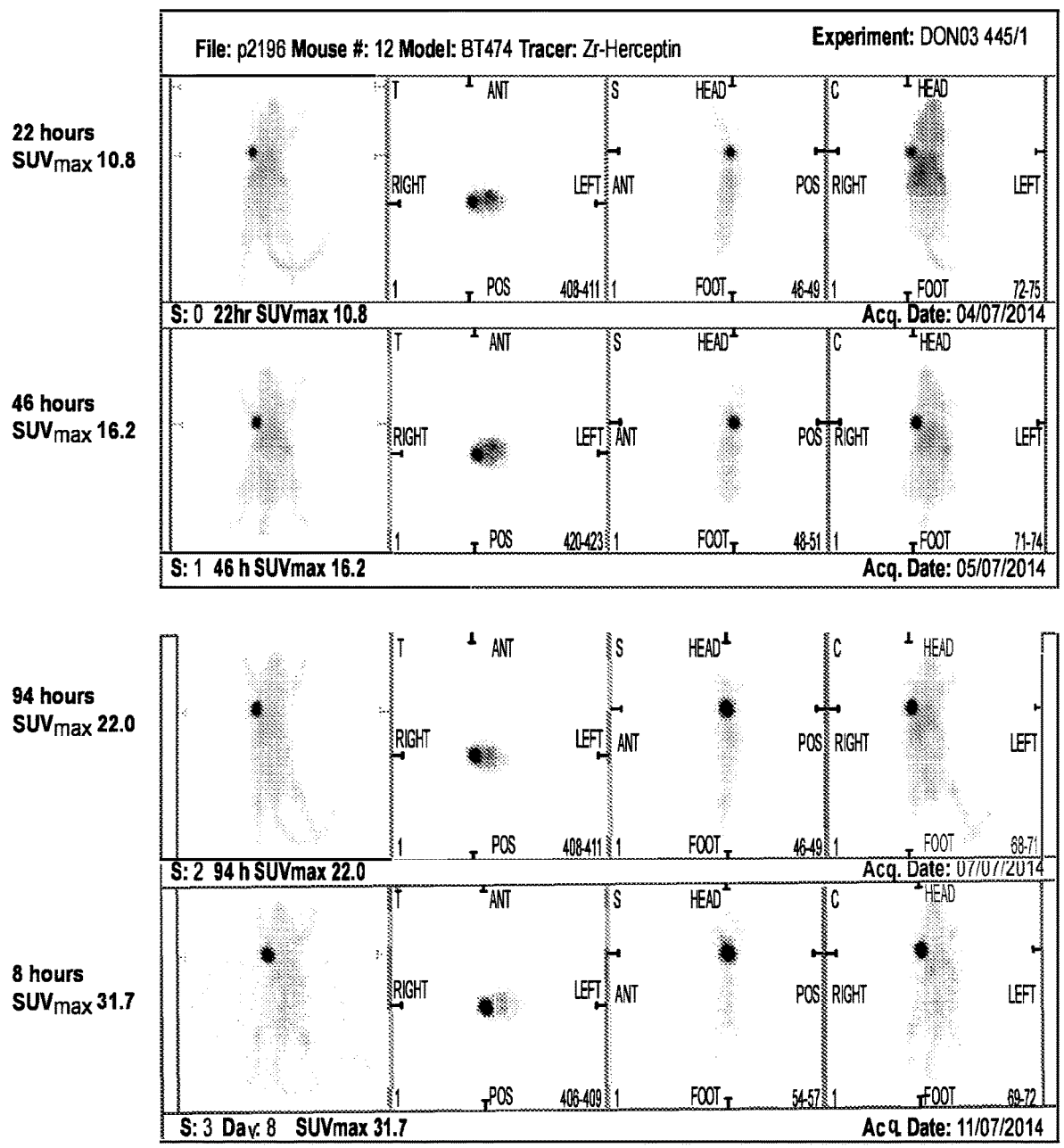
FIG. 1. Micro-PET imaging of HER2-positive tumour (BT474 breast carcinoma model) using $^{89}$Zr(DFO-squarate-trastuzumab).

The present inventors have found that the synthesis of the compound of formula (I) (and, in particular, the synthesis of conjugates of this compound with biological molecules) is simpler and more amendable to the presence of pH-sensitive molecules, such as antibodies, than that of N-suc-DFO-TFP, as it is not necessary to use Fe$^{3+}$ ions to protect the hydroxamic acid groups. This makes antibody conjugation and radiolabelling with $^{89}$Zr straightforward. In addition, the compound of formula (I) is not sensitive to chloride-containing buffers, does not result in the formation of aggregates during conjugation with biomolecules, and does not bind reversibly to biological molecules.

In addition, unexpectedly, the radiolabelled conjugates of the compounds of formula (I) with target molecules exhibit improved tumour targeting and tissue selectivity over a number of the known radionuclide chelators (particularly other DFO-based chelators) that are used as PET imaging agents.

There are a number of potential factors that could contribute to this improved tumour targeting and tissue selectivity, including the strength with which the radioisotope is chelated, metabolic stability, and the excretion rate of metabolites. None of these advantages of the compounds of the present invention are disclosed in the prior art, nor could they expected, and the relative weighting of their contributions to the overall improved performance of the compounds of the present invention is unknown.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutically acceptable salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaieic, hydroiodic, phenylacetic, alkanoic (such as acetic, HOOC—(CH$_2$)$_n$—COOH where n is any integer from 0 to 6, i.e. 0, 1, 2, 3, 4, 5 or 6), and the like. Similarly, pharmaceutically acceptable cations include, but are not limited to sodium, potassium, calcium, aluminum, lithium and ammonium. A person skilled in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent (such as ether, ethyl acetate, ethanol, isopropanol or acetonitrile), or in a mixture of the two.

It will be apparent that the compounds of formula (I) may, but need not, be present as a hydrate, solvate or non-covalent complex (to a metal other than the radionuclide). In addition, the various crystal forms and polymorphs are within the scope of the present invention, as are prodrugs of the compounds provided herein.

A "prodrug" is a compound that may not fully satisfy the structural requirements of the compounds provided herein, but is modified in vivo, following administration to a subject or patient, to produce a radiolabelled conjugate as provided herein. For example, a prodrug may be an acylated derivative of a radiolabelled conjugate. Prodrugs include compounds wherein hydroxyl or amine groups are bonded to any group that, when administered to a mammalian subject, cleaves to form a free hydroxyl or amine group, respectively. Examples of prodrugs include, but are not limited to, acetate, formate, phosphate and benzoate derivatives of amine functional groups within the radiolabelled conjugate. Prodrugs of the may be prepared by modifying functional groups present in the compounds in such a way that the modifications are cleaved in vivo to generate the parent compounds.

A "substituent" as used herein, refers to a molecular moiety that is covalently bonded to an atom within a molecule of interest. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then two hydrogens on the atom are replaced. An oxo group that is a substituent of an aromatic carbon atom results in a conversion of —CH— to —C(=O)— and a loss of aromaticity. For example a pyridyl group substituted by oxo is a pyridone. Examples of suitable substituents are alkyl, heteroalkyl, halogen (for example, fluorine, chlorine, bromine or iodine atoms), OH, =O, SH, SO$_2$, NH$_2$, NHalkyl, =NH, N$_3$ and NO$_2$ groups.

The term "optionally substituted" refers to a group in which one, two, three or more hydrogen atoms have been replaced independently of each other by alkyl, halogen (for example, fluorine, chlorine, bromine or iodine atoms), OH, =O, SH, =S, SO$_2$, NH$_2$, NHalkyl, =NH, N$_3$ or NO$_2$ groups.

As used herein a wording defining the limits of a range of length such as, for example, "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range.

The term "leaving group" refers to any moiety that is capable of being displaced from the squarate moiety upon reaction with a target molecule. The leaving group will be displaced and a bond will form between a group (such as an amino group of a lysine side chain) of the target molecule and the squarate. In one embodiment, the leaving group ("L") is OR. In one embodiment, R is selected from $C_1$ to $C_{10}$ alkyl, $C_1$ to $C_{10}$ heteroalkyl, $C_2$ to $C_{10}$ alkene and $C_2$ to $C_{10}$ alkyne, and aryl, each of which is optionally substituted. In one embodiment, R is $C_1$ to $C_{10}$ alkyl (e.g. $C_1$ to $C_6$ alkyl, such as methyl, ethyl, propyl or butyl). In one embodiment, R is methyl or ethyl. In one embodiment, R is ethyl. In another embodiment, L is halogen (e.g. fluorine, chlorine, bromine or iodine), or L is an azide group.

The term "alkyl" refers to a saturated, straight-chain or branched hydrocarbon group that contains from 1 to 10 carbon atoms, for example a n-octyl group, especially from 1 to 6, i.e. 1, 2, 3, 4, 5, or 6, carbon atoms. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl.

The term "heteroalkyl" refers to an alkyl group as defined above that contains one or more heteroatoms selected from oxygen, nitrogen and sulphur. Specific examples of heteroalkyl groups are methoxy, trifluoromethoxy, ethoxy, n-propyloxy, iso-propyloxy, butoxy, tert-butyloxy, methoxymethyl, ethoxymethyl, —$CH_2CH_2OH$, —$CH_2OH$, methoxyethyl, 1-methoxyethyl, 1-ethoxyethyl, 2-methoxyethyl or 2-ethoxyethyl, methylamino, ethylamino, propylamino, iso-propylamino, dimethylamino, diethylamino, iso-propyl-ethylamino, methylamino methyl, ethylamino methyl, di-iso-propylamino ethyl, methylthio, ethylthio, iso-propylthio, methanesulfonyl, trifluoromethanesulfonyl, enol ether, dimethylamino methyl, dimethylamino ethyl, acetyl, propionyl, butyryloxy, acetyloxy, methoxycarbonyl, ethoxy-carbonyl, propionyloxy, acetylamino, propionylamino, carboxymethyl, carboxyethyl or carboxypropyl, N-ethyl-N-methylcarbamoyl and N-methylcarbamoyl. Further examples of heteroalkyl groups are nitrile, iso-nitrile, cyanate, thiocyanate, iso-cyanate, iso-thiocyanate and alkylnitrile groups.

The term "alkenyl" refers to an at least partially unsaturated, straight-chain or branched hydrocarbon group that contains from 2 to 10 carbon atoms, especially from 2 to 6, i.e. 2, 3, 4, 5 or 6, carbon atoms. Specific examples of alkenyl groups are ethenyl (vinyl), propenyl (allyl), iso-propenyl, butenyl, ethinyl, propinyl, butinyl, acetylenyl, propargyl, iso-prenyl and hex-2-enyl group. Preferably, alkenyl groups have one or two double bond(s).

The term "alkynyl" refers to an at least partially unsaturated, straight-chain or branched hydrocarbon group that contains from 2 to 10 carbon atoms, especially from 2 to 6, i.e. 2, 3, 4, 5 or 6, carbon atoms. Specific examples of alkynyl groups are ethynyl, propynyl, butynyl, acetylenyl and propargyl groups. Preferably, alkynyl groups have one or two (especially preferably one) triple bond(s).

The term "aryl" refers to an aromatic group that contains one or more rings containing from 6 to 14 ring carbon atoms, preferably from 6 to 10 (especially 6) ring carbon atoms. Examples are phenyl, naphthyl and biphenyl groups. Examples of substituted aryl groups suitable for use in the present invention include p-toluenesulfonyl (Ts), benzenesulfonyl (Bs) and m-nitrobenzenesulfonyl (Ns).

Preferred compounds of the present invention are those where R is $C_1$ to $C_{10}$ alkyl (and in particular, where R is ethyl).

In one embodiment, the leaving group is selected from $OCH_2CH_3$, O-p-toluenesulfonate (OTs), O-methanesulfonate (OMs), O-trifluoromethanesulfonate (OTf), O-benzenesulfonate (OBs), O-m-nitrobenzenesulfonate (ONs), cyanate (CN), azide ($N_3$) and halogen (e.g. fluorine, chlorine, bromine or iodine).

As used herein, the term "radionuclide complex" refers to a compound of formula (I), as defined above, which has formed a co-ordination complex with a radionuclide. Generally, this occurs as a result of the formation of co-ordination bonds between the electron donating groups (such as the hydroxamate groups) of the compound of formula (I) and the radionuclide.

In the compounds of the present invention, co-ordination bonds are postulated to form between the hydroxamic acid groups of the DFO and the radionuclide. However, without wishing to be bound by theory, the present inventors also believe that the oxo groups on the squarate moiety (in addition to the hydroxamic acid groups of DFO) also act as donor atoms, providing one or two additional sites by which the compound of formula (I) can bind to the radionuclide. This results in an eight-coordinate complex, which is very favourable from a stability perspective for radionuclides that have eight-coordinate geometry (such as $^{89}Zr$), and may explain the stability observed in respect of the complexes of the present invention. In particular, it may explain why the radionuclide does not as readily leach out of the target tissue (into other tissue, such as bone) therefore resulting in improved imaging quality when compared to other DFO-based imaging agents. These advantages of the compounds of the present invention over the currently-used chelators are illustrated in the Figures and Examples.

Figure 2:
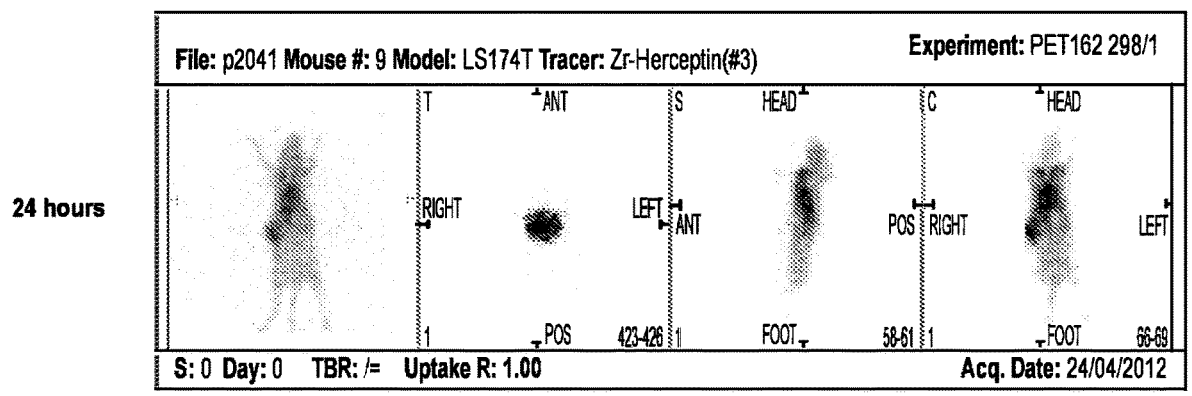
FIG. 2. Micro-PET imaging of HER2-positive tumour (LS174T colorectal tumour model) using $^{89}$Zr(DFO-maleimide-trastuzumab).
Figure 3:
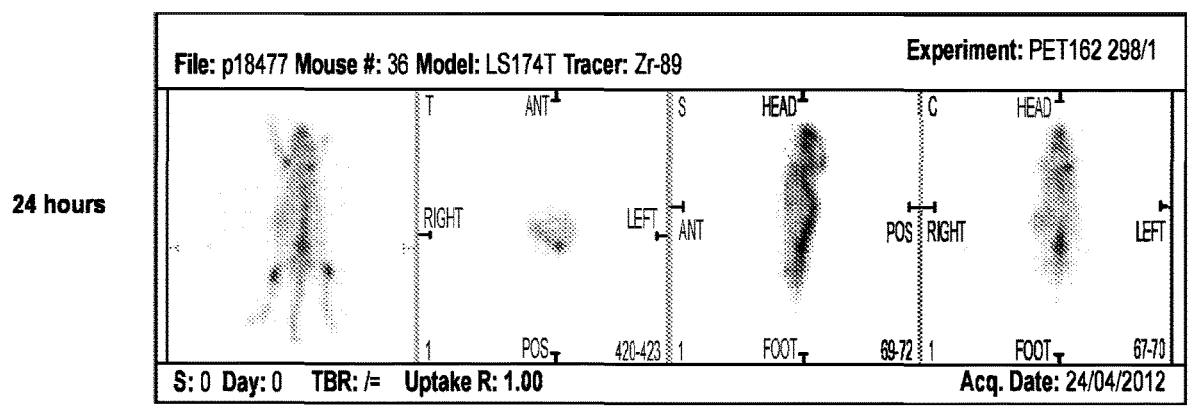
FIG. 3. Micro-PET imaging of HER2-positive tumour (LS174T colorectal tumour model) using $^{89}$ZrCl.
Figure 18:
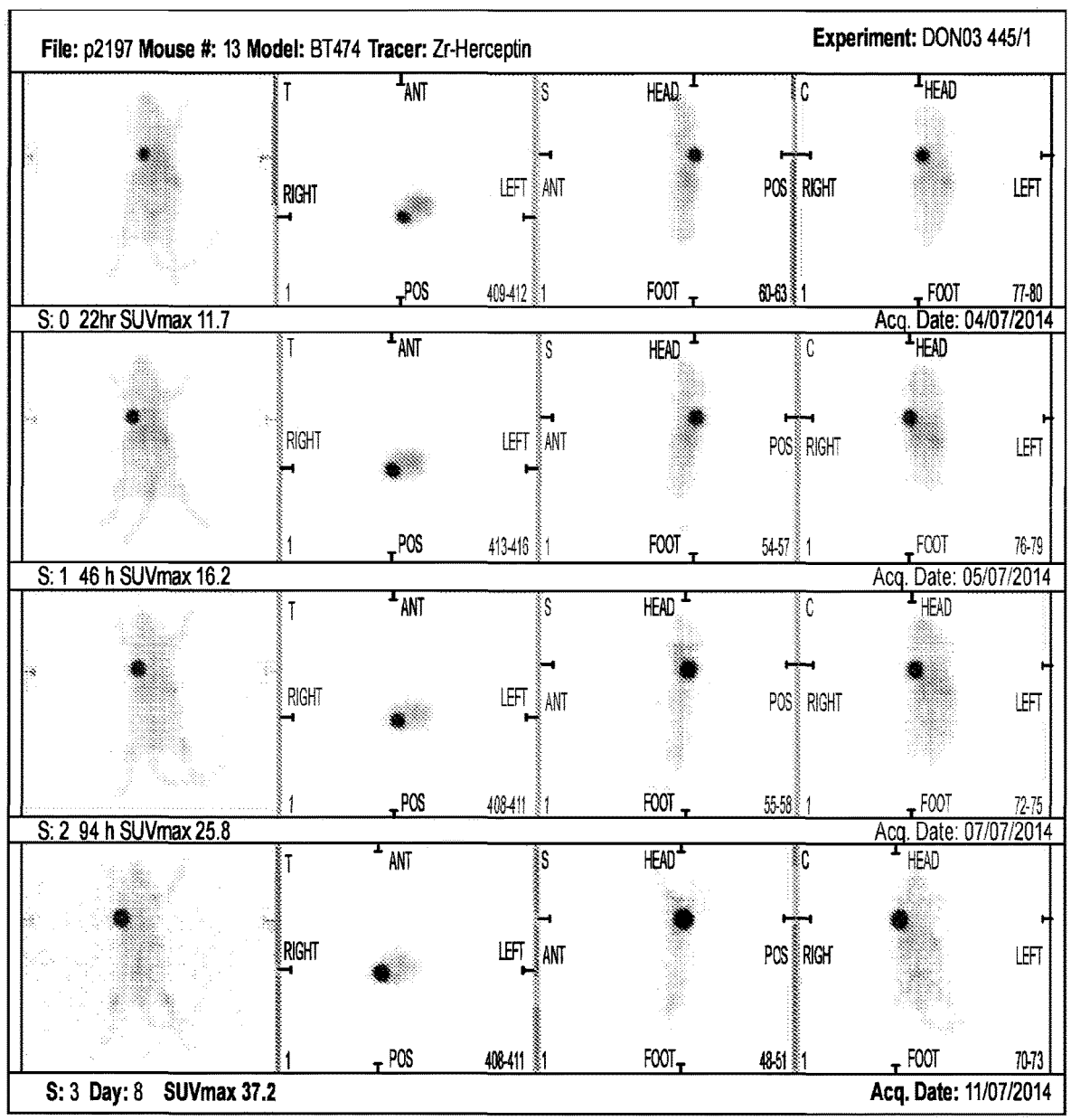
FIG. 18. PET image of mouse 2 after administration of $^{89}$ZrDFOSq-Herceptin.
Figure 19:
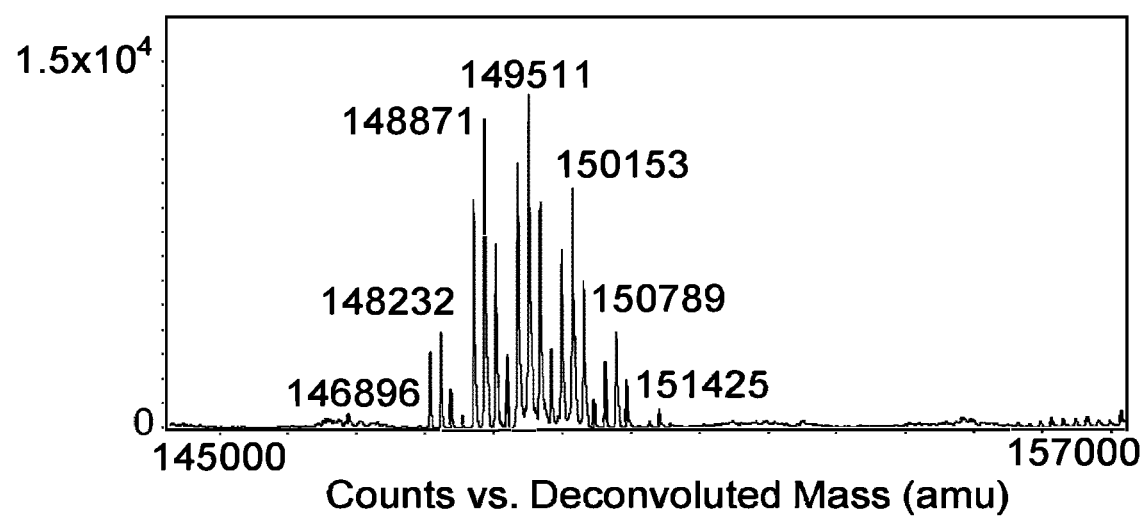
FIG. 19. Deconvoluted ESI-MS of DFOSq-trastuzumab (unlabelled trastuzumab=148,232).
Figure 20:
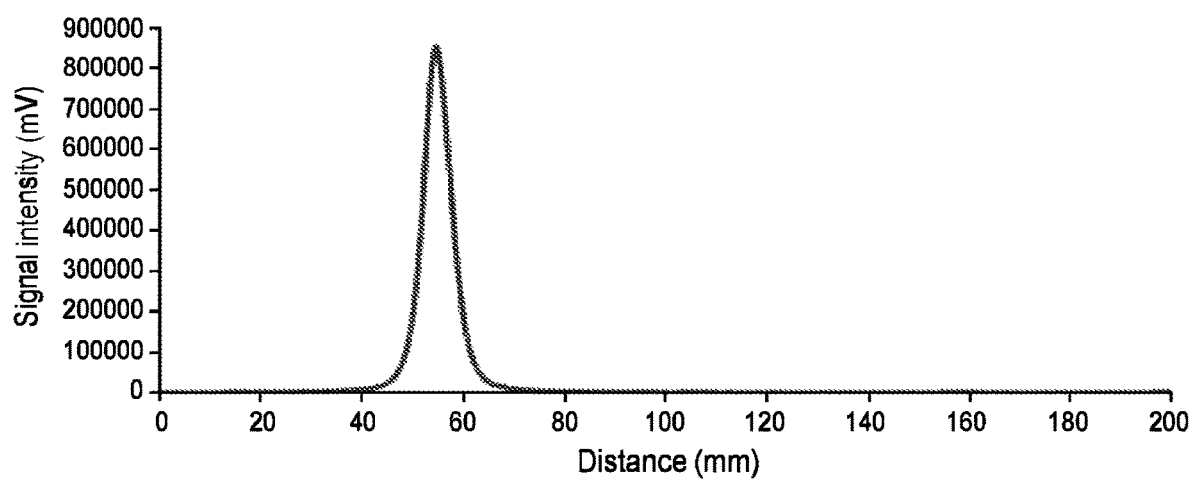
FIG. 20. iTLC analysis of $^{89}$Zr-DFOPhNCS-trastuzumab reaction mixture after 30 min (origin is at 55 mm, solvent front at 150 mm; labelled trastuzumab remains at the origin, activity with a distance of >70 mm (r.f.>0.1) represents non-chelated $^{89}$Zr).
Figure 21A:
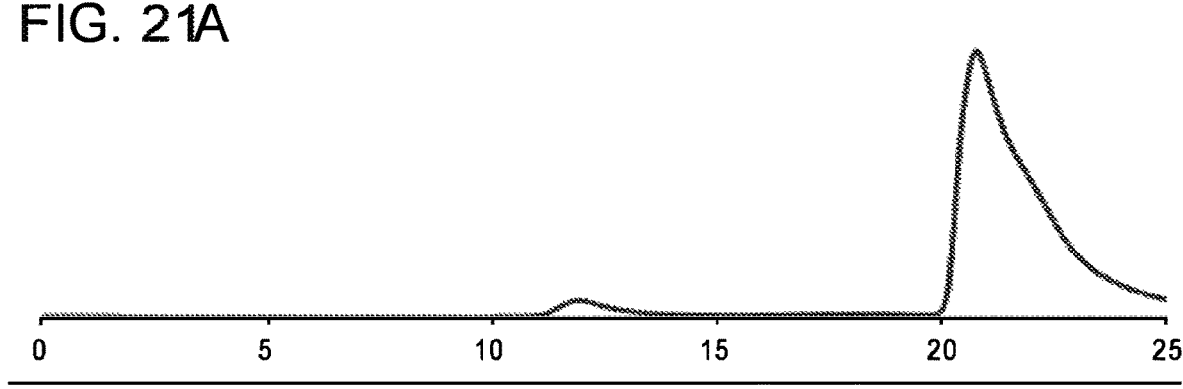
FIGS. 21A-21B. SE-HPLC analysis of $^{89}$Zr-DFOSq-trastuzumab after PD-10 purification (FIG. 21A: absorbance at 280 nm.
Figure 21B:
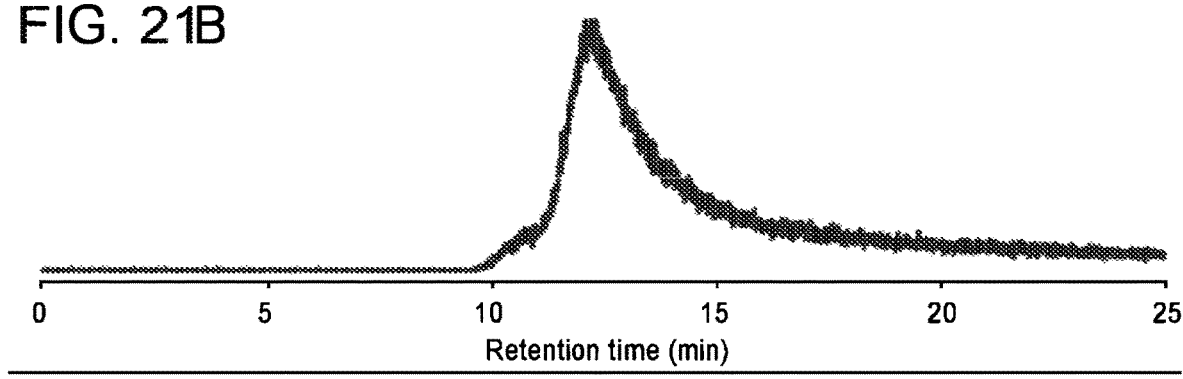
Figure 22:
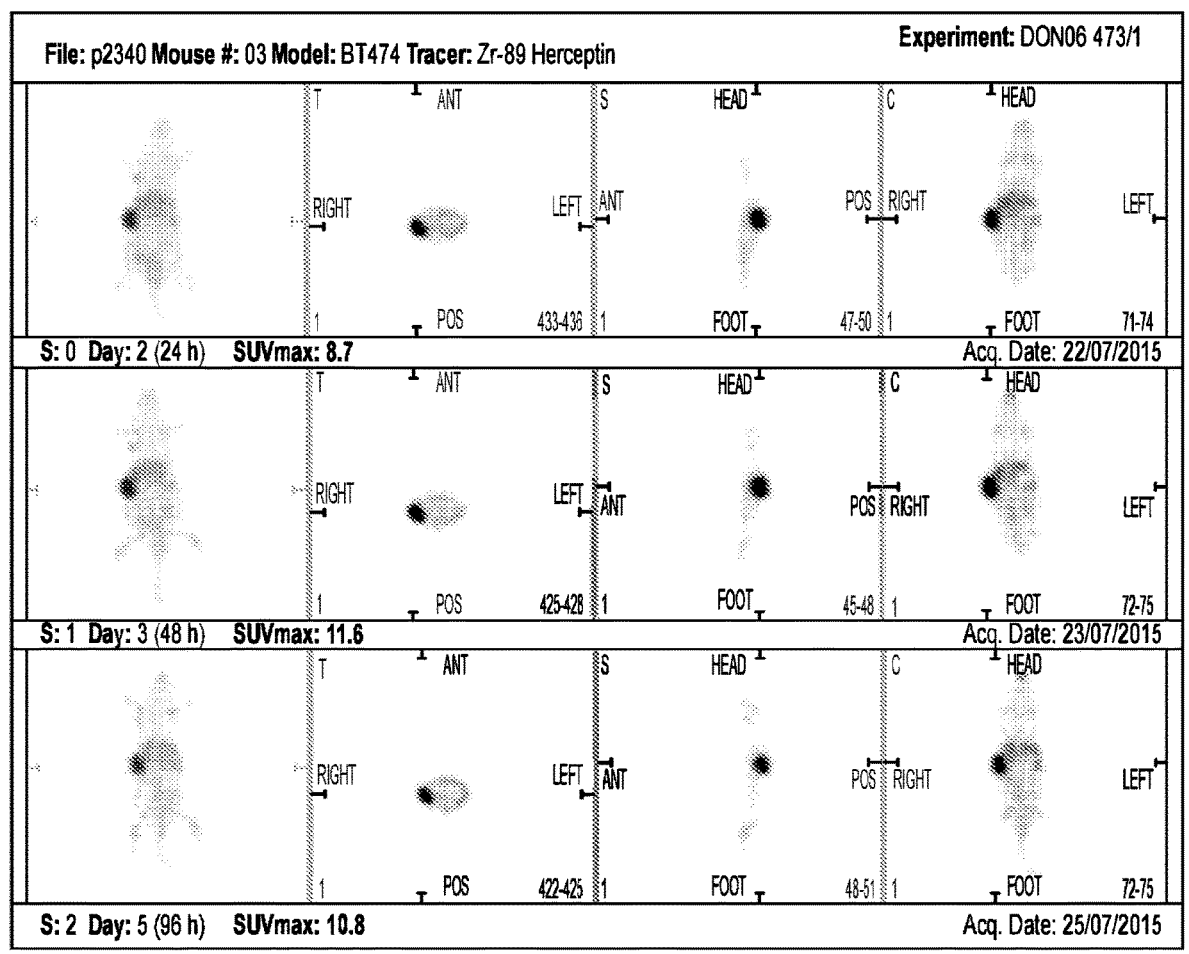
FIG. 22. PET imaging of BT474 tumour bearing NOD/SCID mice using $^{89}$Zr-DFOSq-trastuzumab.
Figure 22:
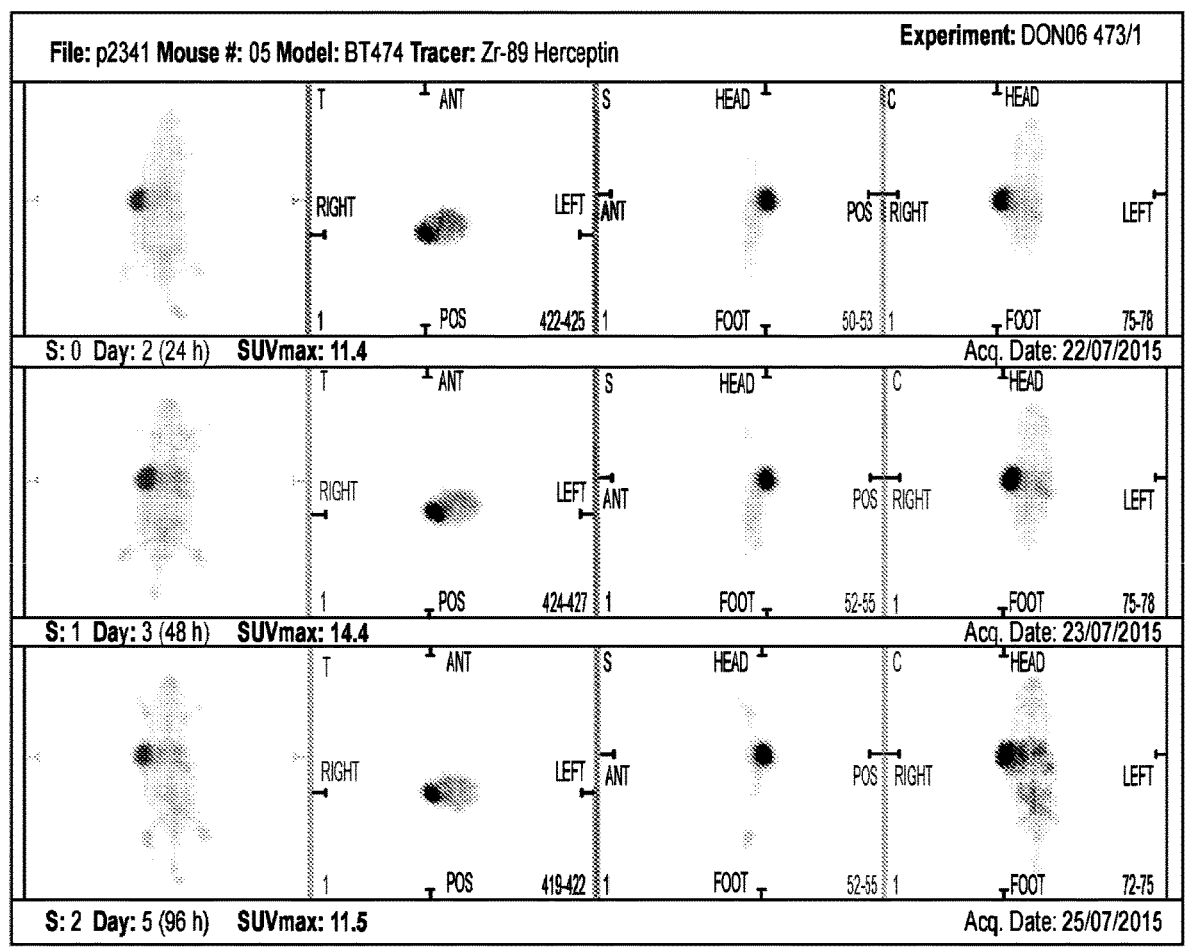
Figure 22:
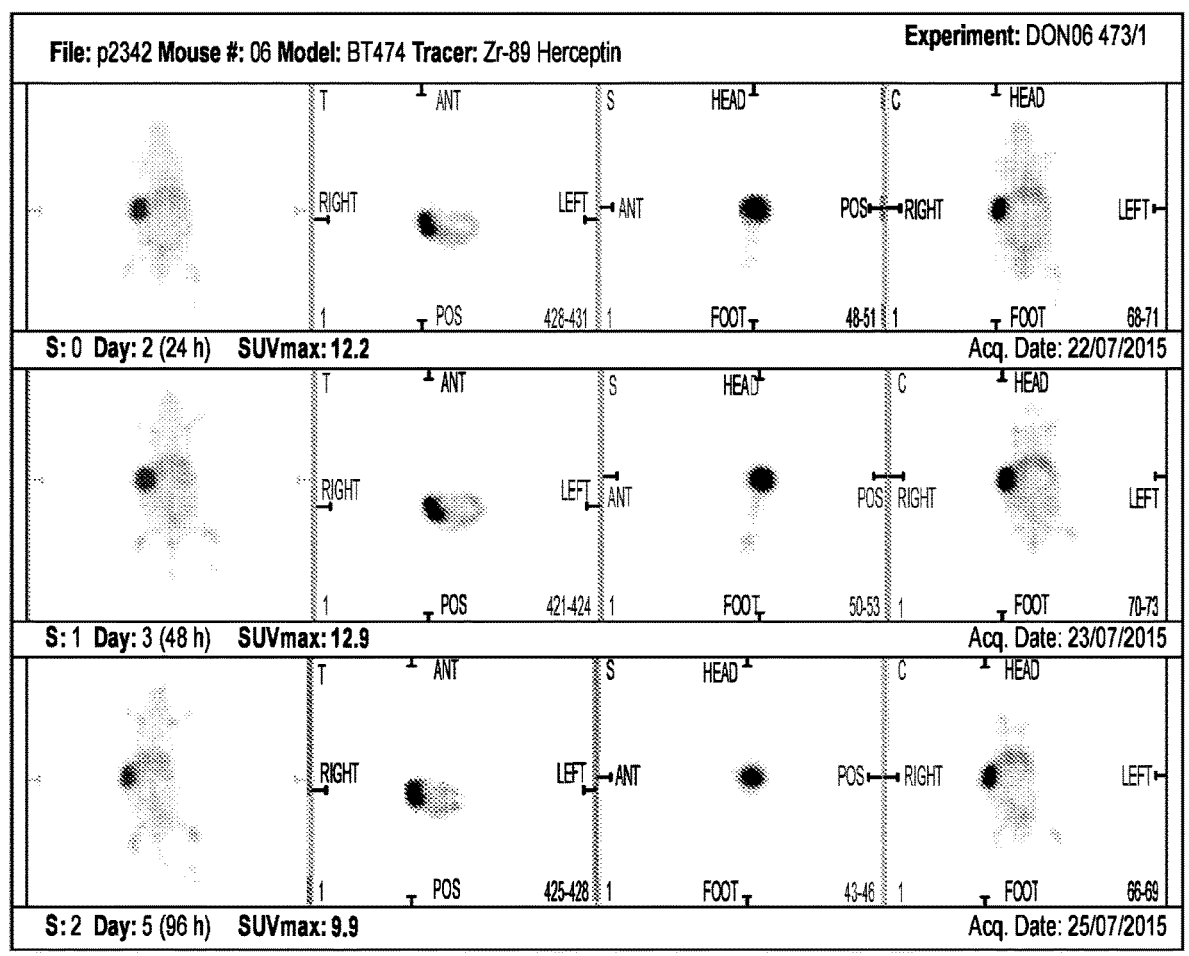
Figure 22:
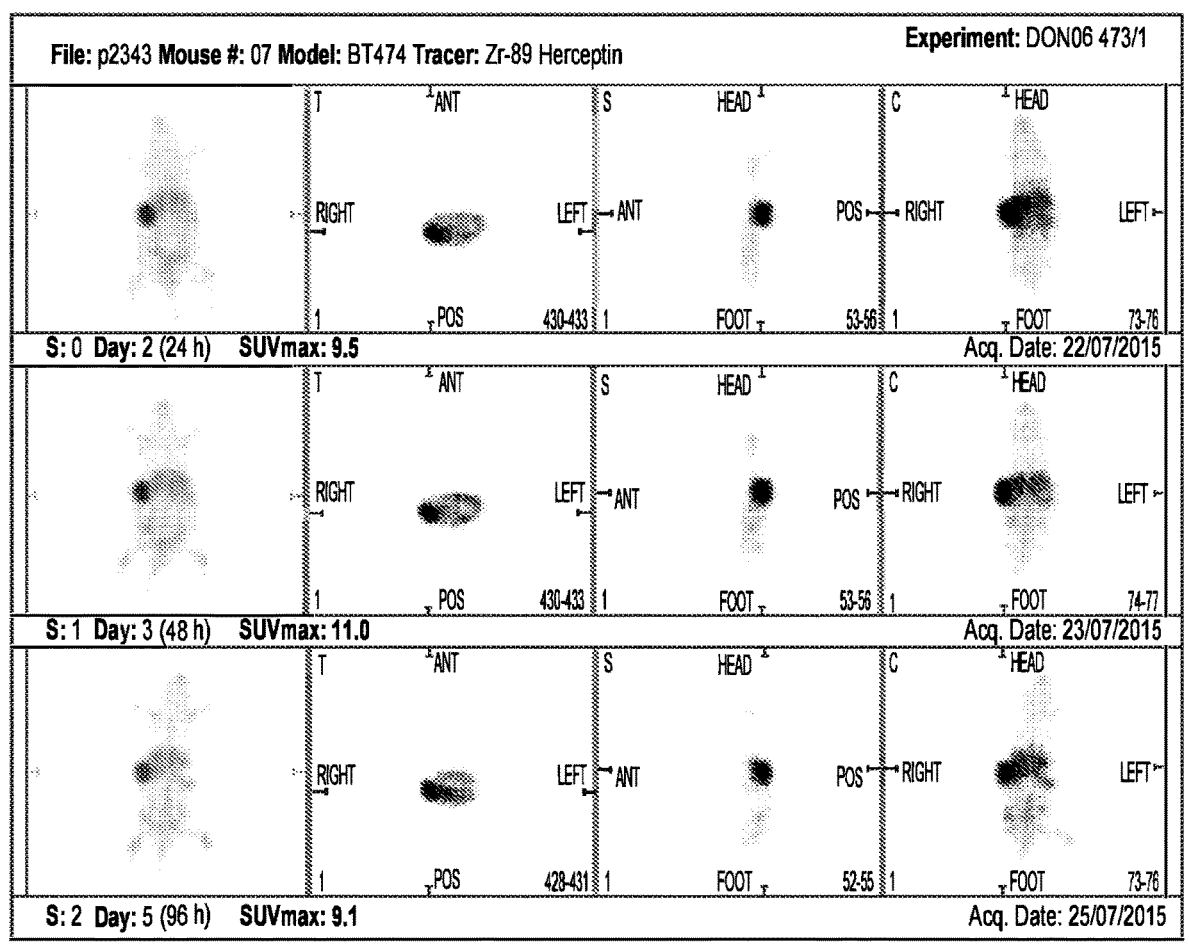
Figure 23:
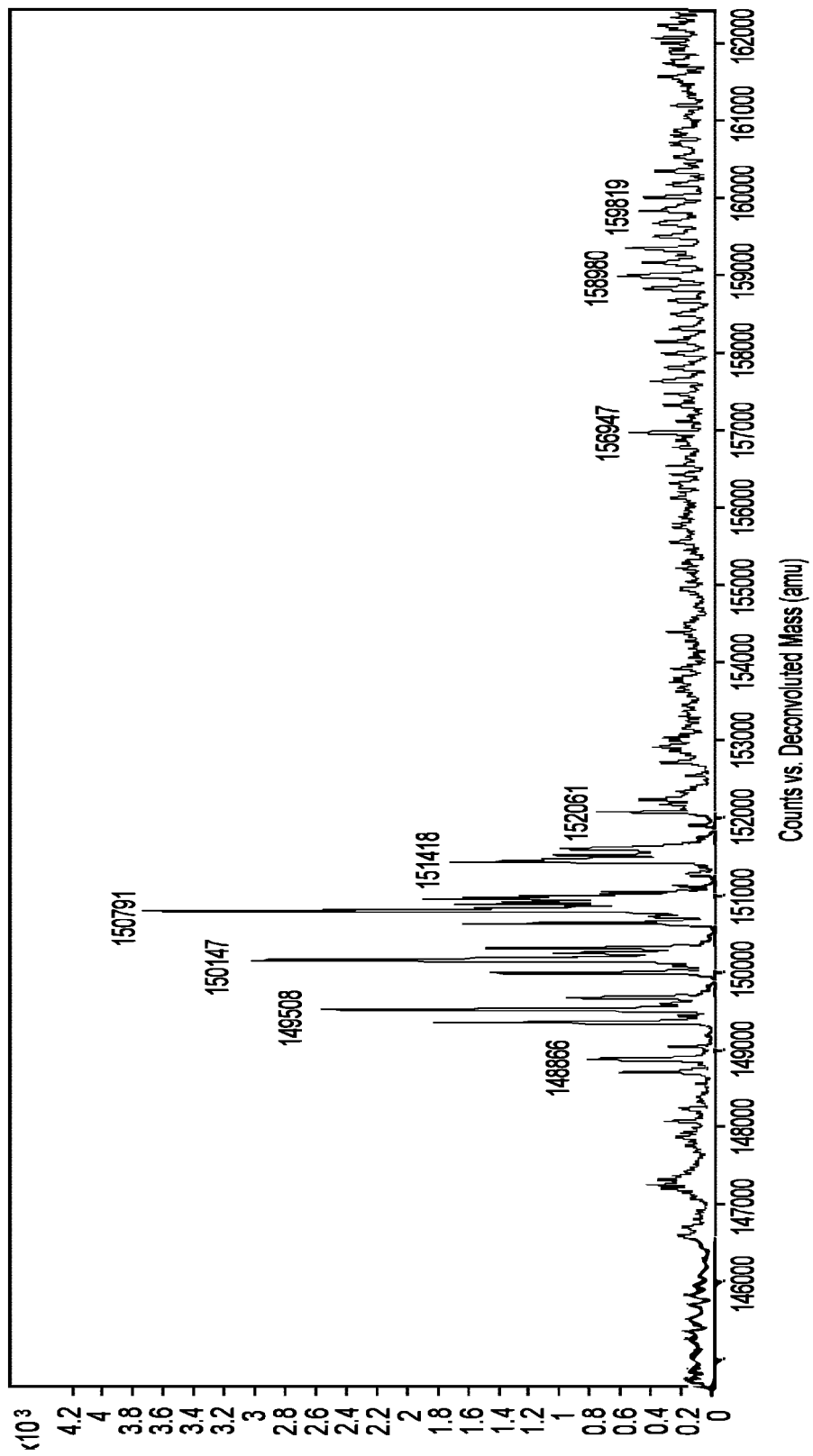
FIG. 23. Deconvoluted ESI-MS of DFOSq-trastuzumab (unlabelled trastuzumab=148,232).
Figure 24:
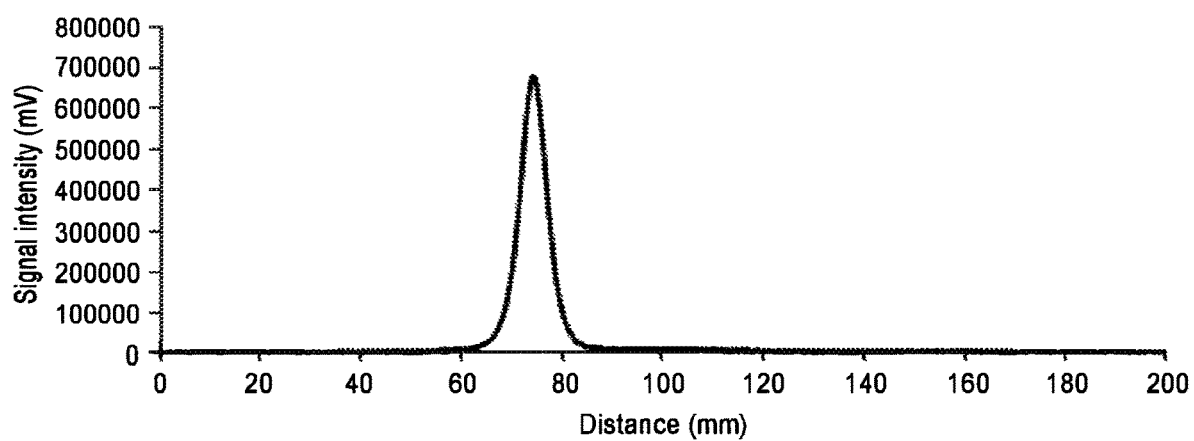
FIG. 24. iTLC analysis of $^{89}$Zr-DFOSq-trastuzumab reaction mixture after 1 hr (origin is at 70 mm, solvent front at 160 mm; labelled trastuzumab remains at the origin, activity with a distance of >80 mm (r.f.>0.1) represents non-chelated $^{89}$Zr).
Figure 25:
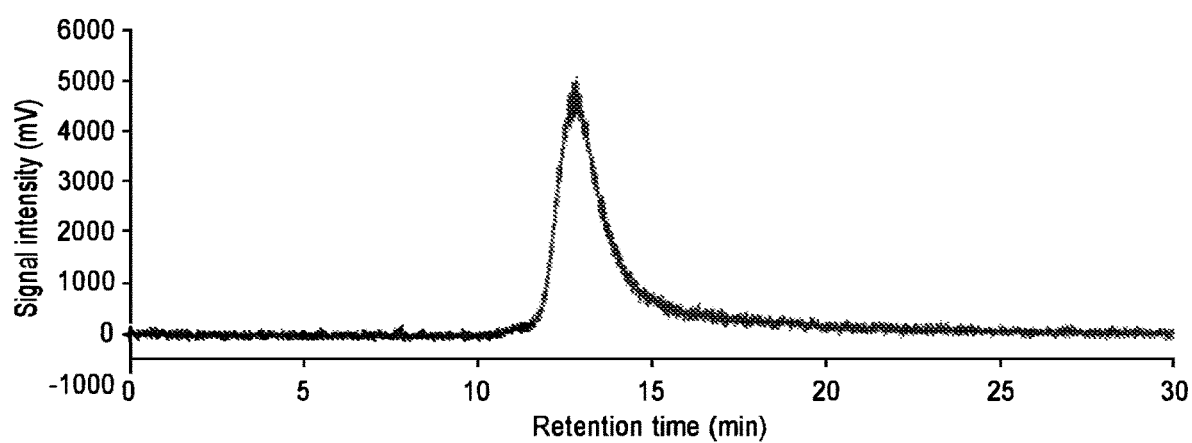
FIG. 25. Radiation trace by SE-HPLC analysis of the purified $^{89}$Zr-DFOSq-trastuzumab (product retention time ~12.5 min).
Figure 26:
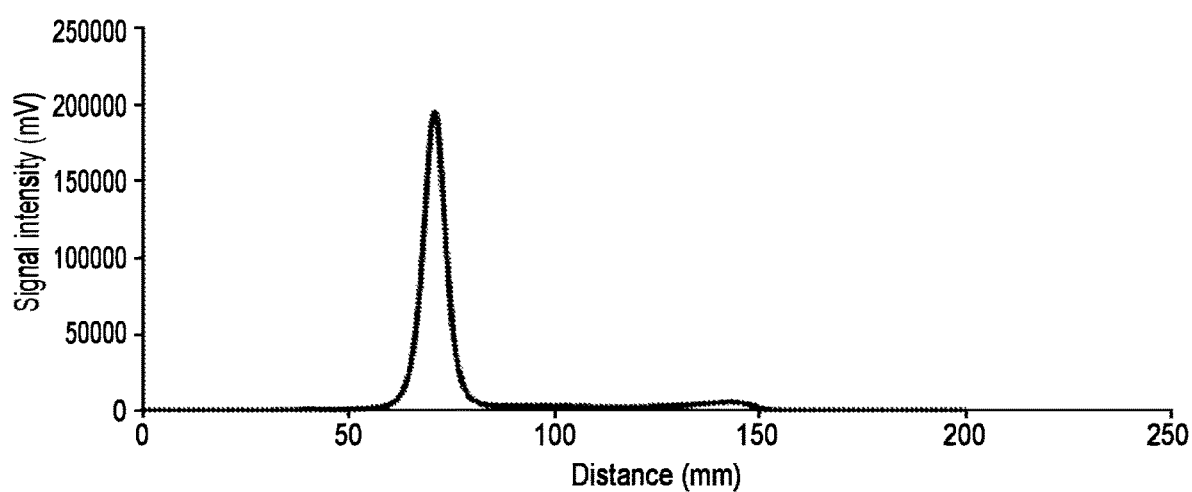
FIG. 26. iTLC analysis of $^{89}$Zr-DFOSq-trastuzumab reaction mixture after 1.5 hr (origin is at 70 mm, solvent front at 145 mm; labelled trastuzumab remains at the origin, activity with a distance of >80 mm (r.f.>0.1) represents non-chelated $^{89}$Zr).
Figure 27:
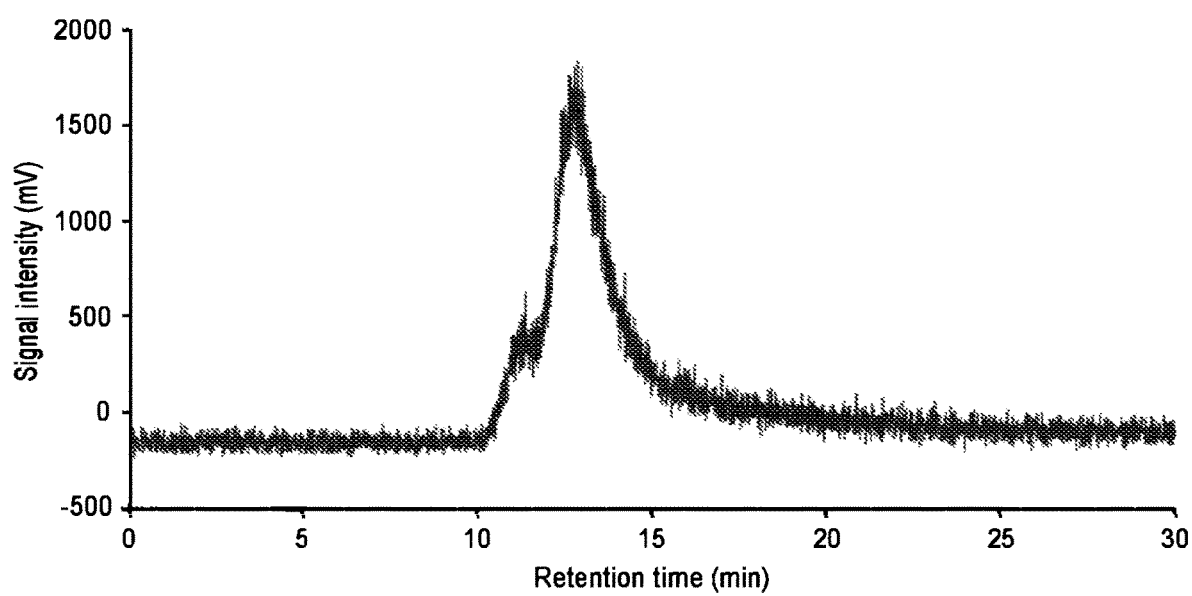
FIG. 27. Radiation trace by SE-HPLC analysis of the purified $^{89}$Zr-DFOSq-trastuzumab (product retention time ~12.5 min).

As shown in FIGS. 1, 18 and 22, $^{89}Zr(DFOSq$-trastuzumab) very selectively targets, and remains concentrated at the site of, the HER2-positive tumour BT474 (a breast carcinoma). This is in contrast to the results shown in FIGS. 2 and 3, which demonstrate significant distribution of the radionuclide (when administered as $^{89}Zr(DFO$-maleimide-trastuzumab) and $^{89}ZrCl$, respectively) throughout the bodies of the mice. As discussed above, one possible contributor to the improved specificity is that the squarate-based agent has strong chelating potential thereby preventing its distribution throughout the body and accumulation in other tissue, such as bone (for which zirconium has a very high affinity), the liver and the kidneys.

Figure 39A:
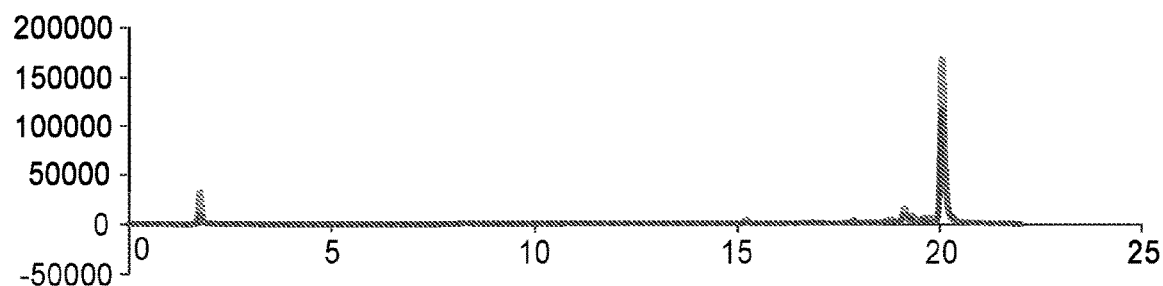
FIGS. 39A-39B. HPLC analysis of $^{89}$Zr-DFOPhNCS-cRGDfK reaction mixture.
Figure 39B:
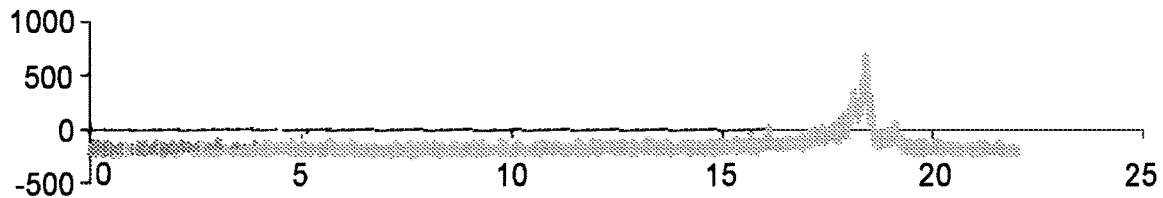
Figure 40A:
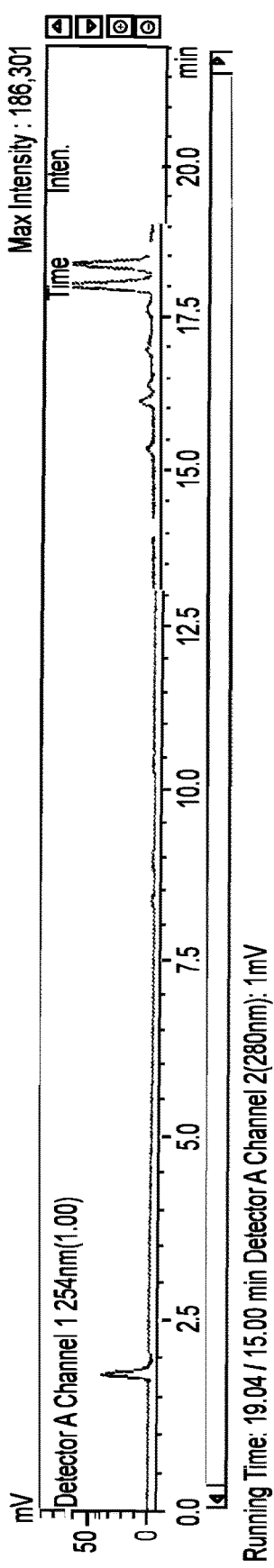
FIGS. 40A-40C. HPLC analysis of $^{89}$Zr-DFOSq-cRGDfK reaction mixture.
Figure 40B:
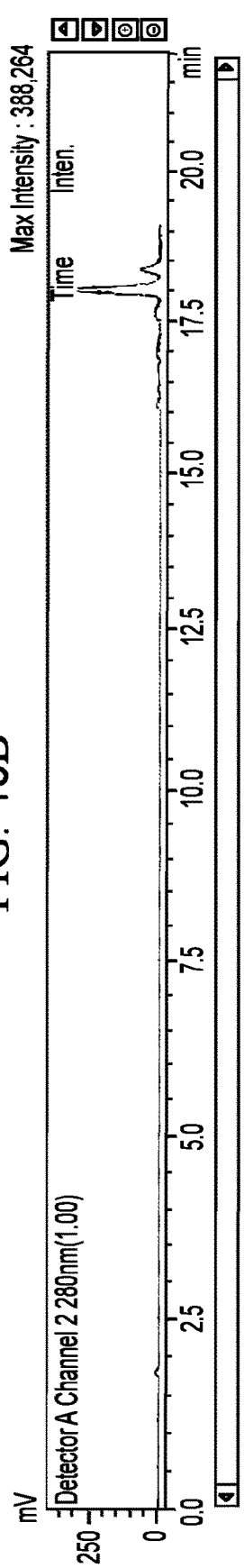
Figure 40C:
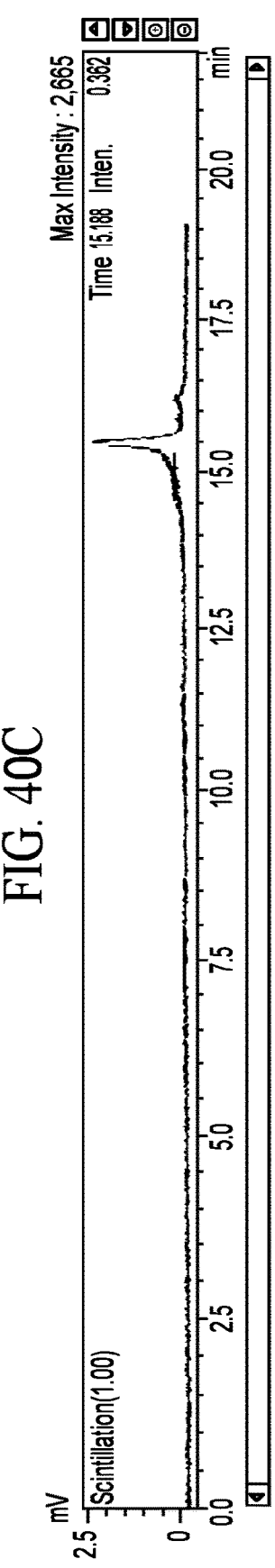
Figure 41A:
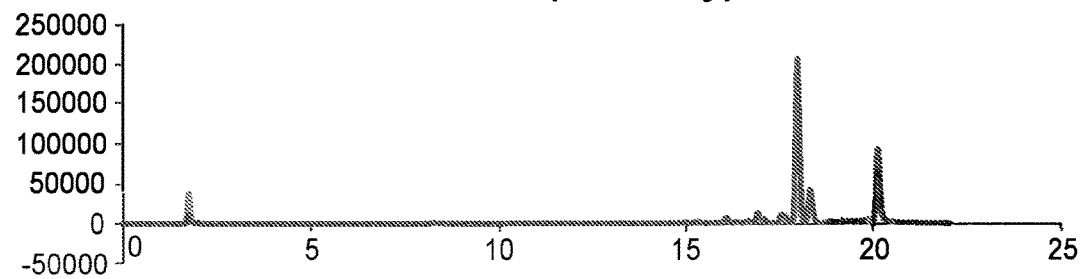
FIGS. 41A-41B. HPLC analysis of DFOPhNCS-cRGDfK/DFOSq-cRGDfK/$^{89}$Zr reaction mixture.
Figure 41B:
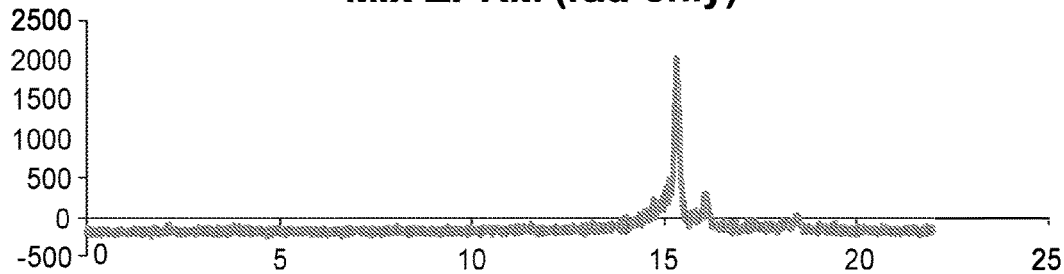

The high affinity for zirconium as compared with $^{89}Zr$ (DFO-PhNCS) is demonstrated in a competition study (see the Examples and FIGS. 39 to 41). The absorbance and radiation spectra show that $^{89}Zr$ is complexed almost exclusively by the conjugate of the present invention when $^{89}Zr$ is exposed to a mixture of a conjugate of the present invention (DFOSq-cRGDfK) with DFOPhNCS-cRGDfK.

Another contributor to the specificity may be the metabolic stability of the radionuclide-labelled compound of the present invention. Metabolites that contain the radionuclide but that are free of the trastuzumab moiety ("non-targeted metabolites") would have no targeting ability, resulting in distribution of the radionuclide throughout the body. This metabolic stability of the compounds of the present invention could not be expected, and cannot readily be explained.

The present inventors also postulate that, even if metabolites of the radionuclide-labelled conjugates of the present invention are formed, they may have a high excretion rate, leading to less accumulation of the radionuclide at non-target sites. This would also be an unexpected property.

Figure 28:
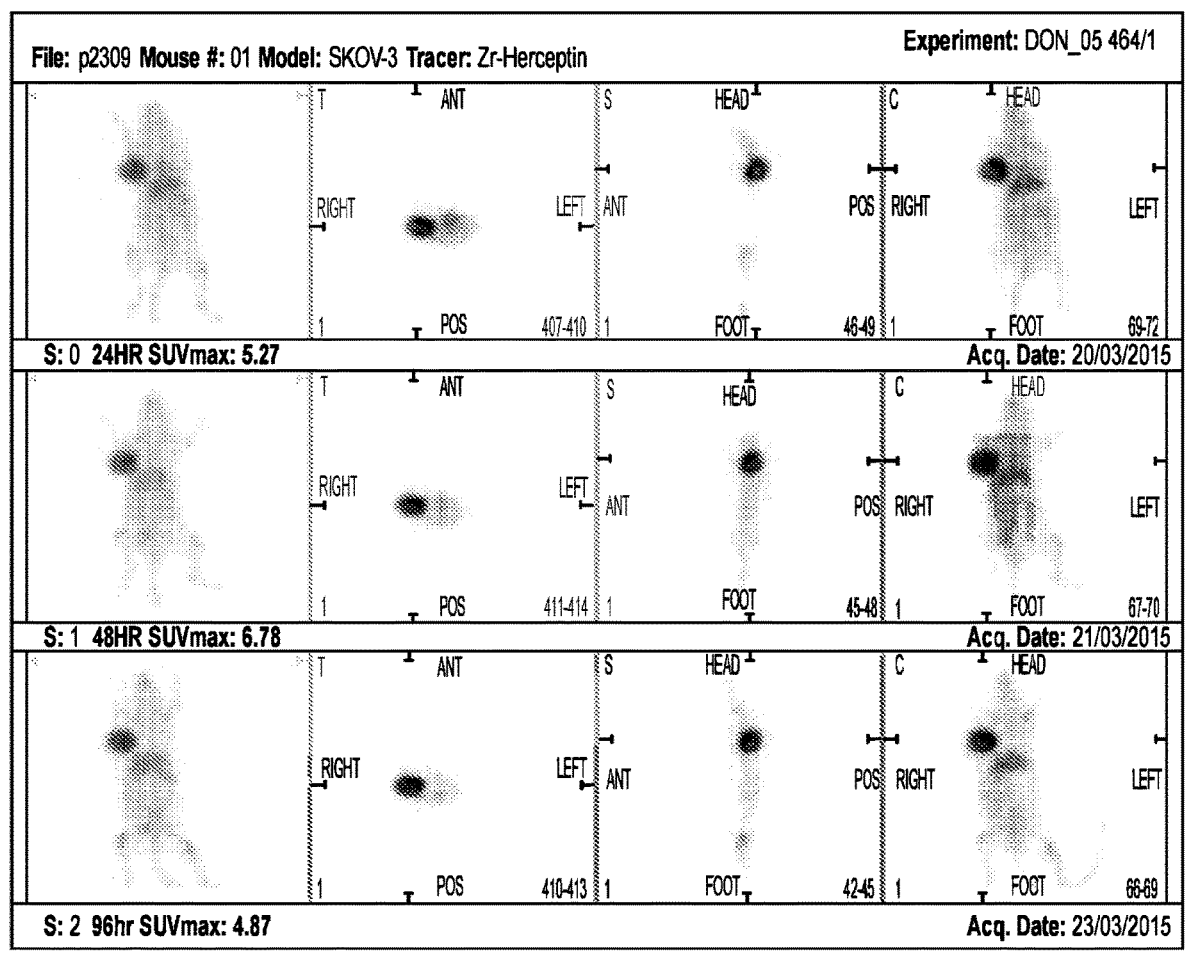
FIG. 28. PET imaging of SKOV3 tumour-bearing mice using $^{89}$Zr-DFOSq-trastuzumab as the imaging agent.
Figure 28:
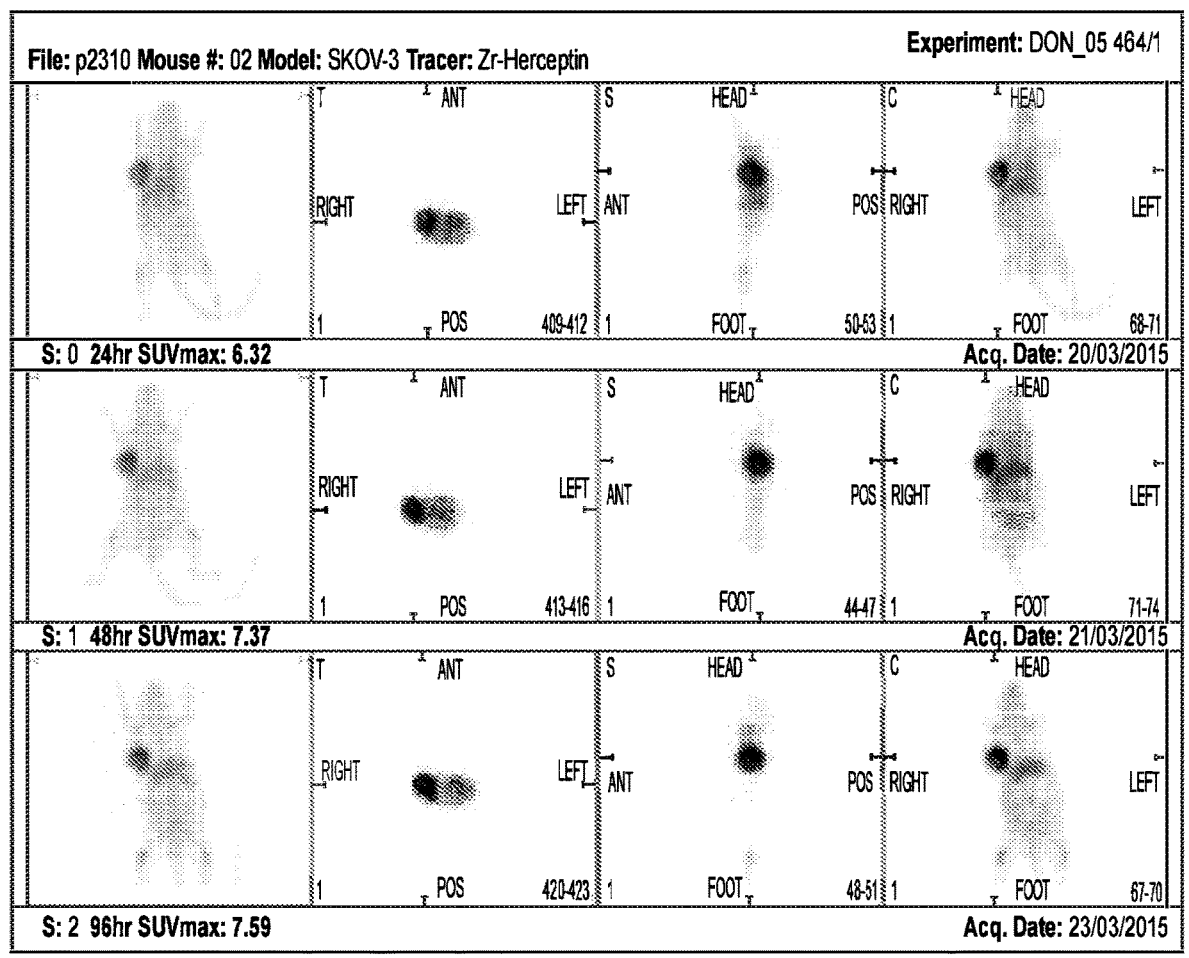
Figure 28:
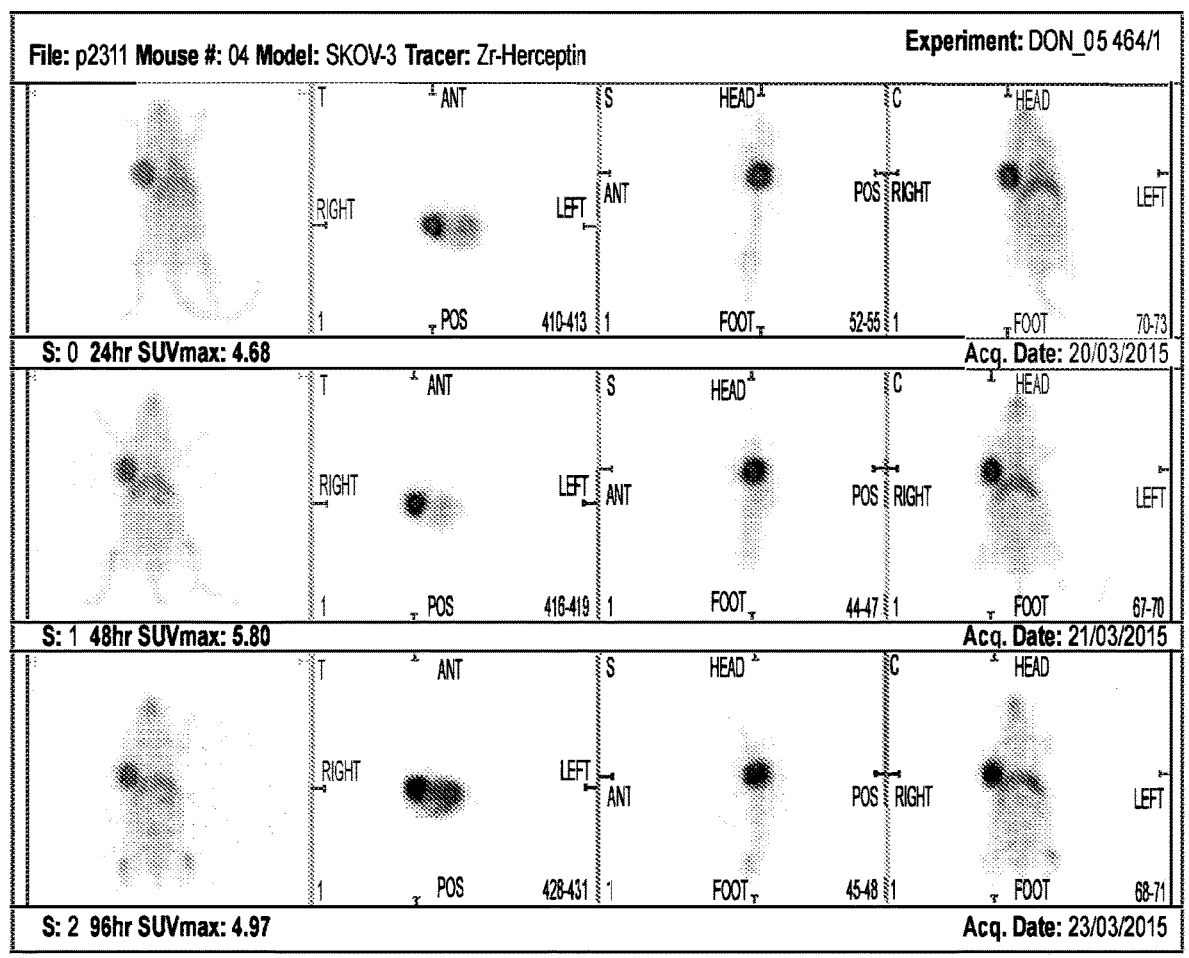
Figure 29:
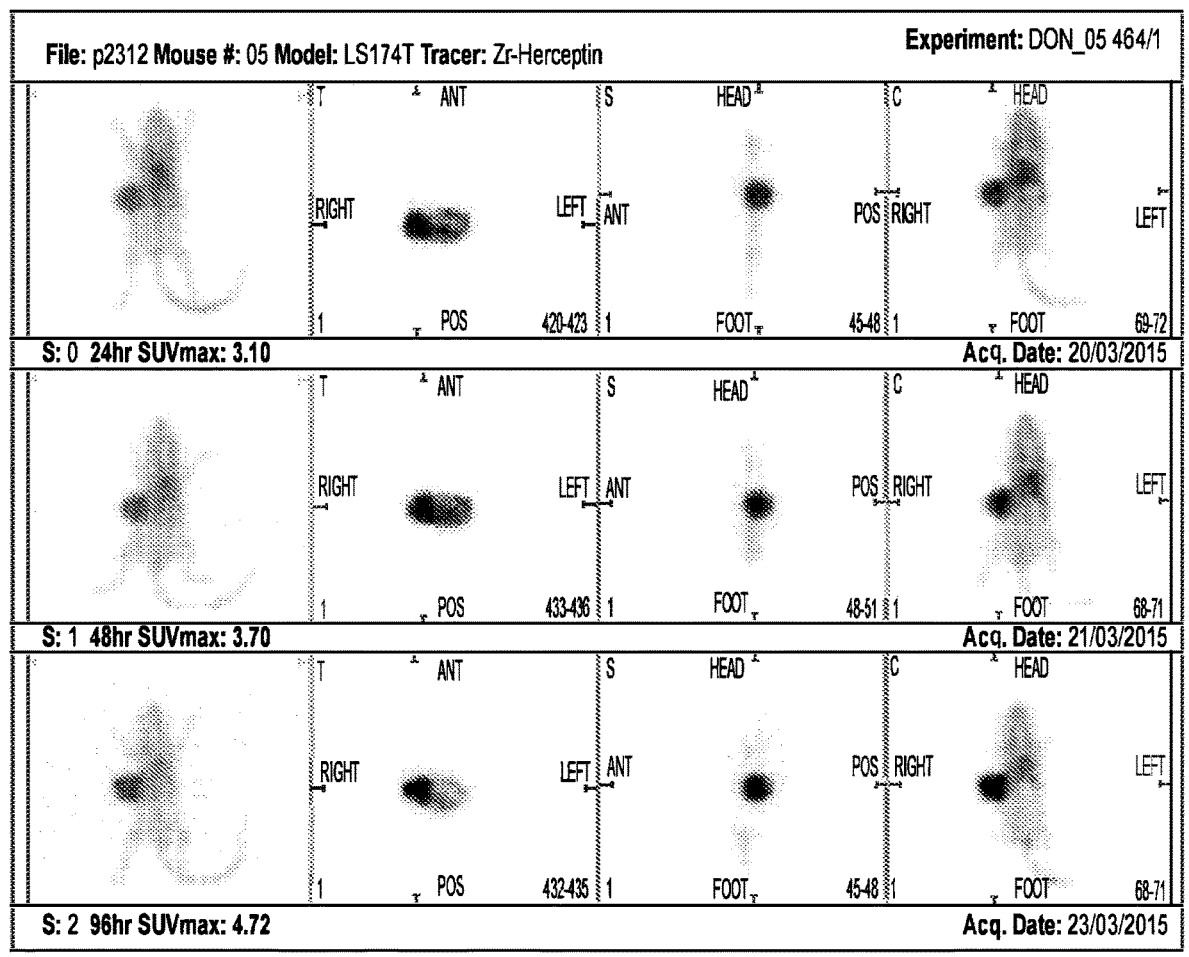
FIG. 29. PET imaging of LS174T tumour-bearing mice using $^{89}$Zr-DFOSq-trastuzumab as the imaging agent.
Figure 29:
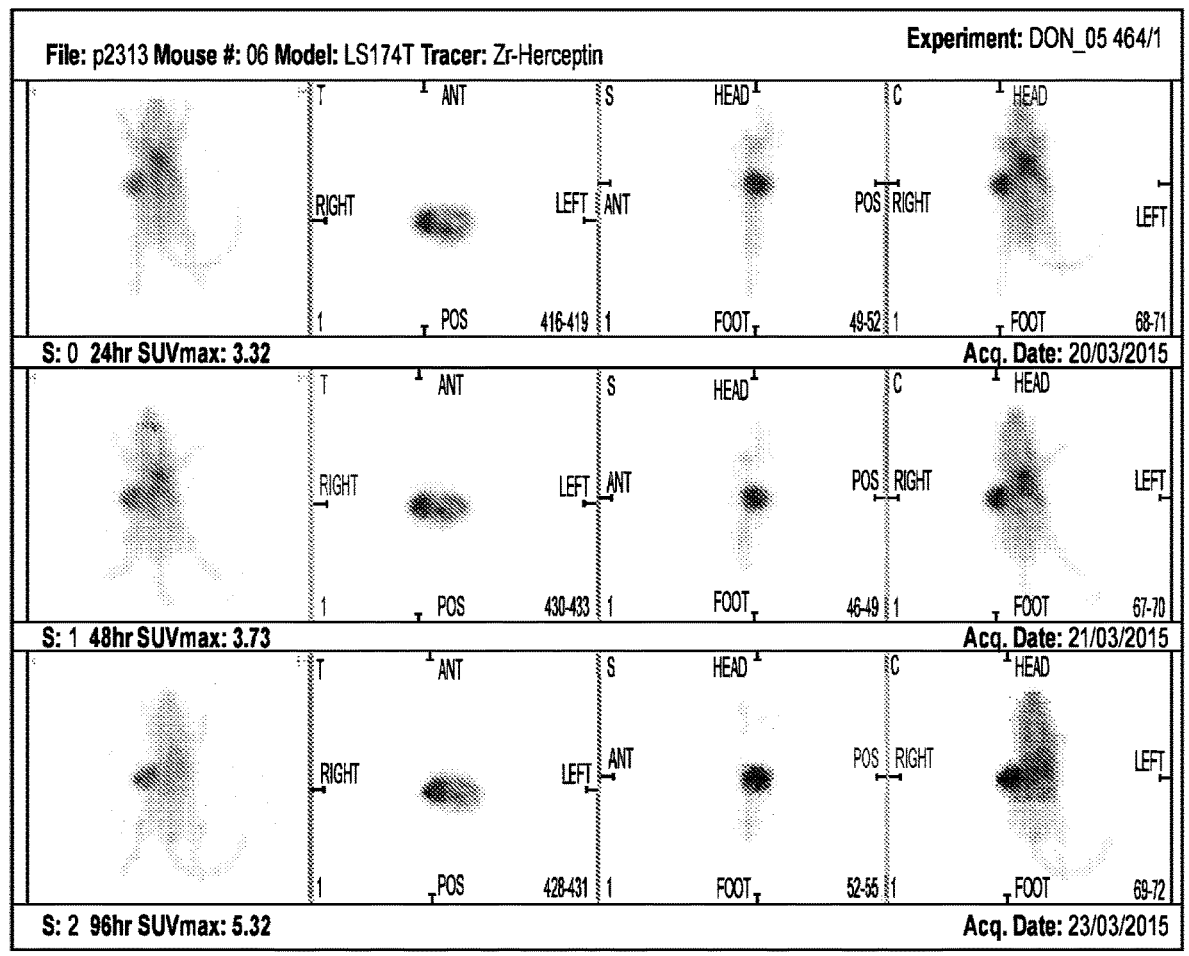
Figure 29:
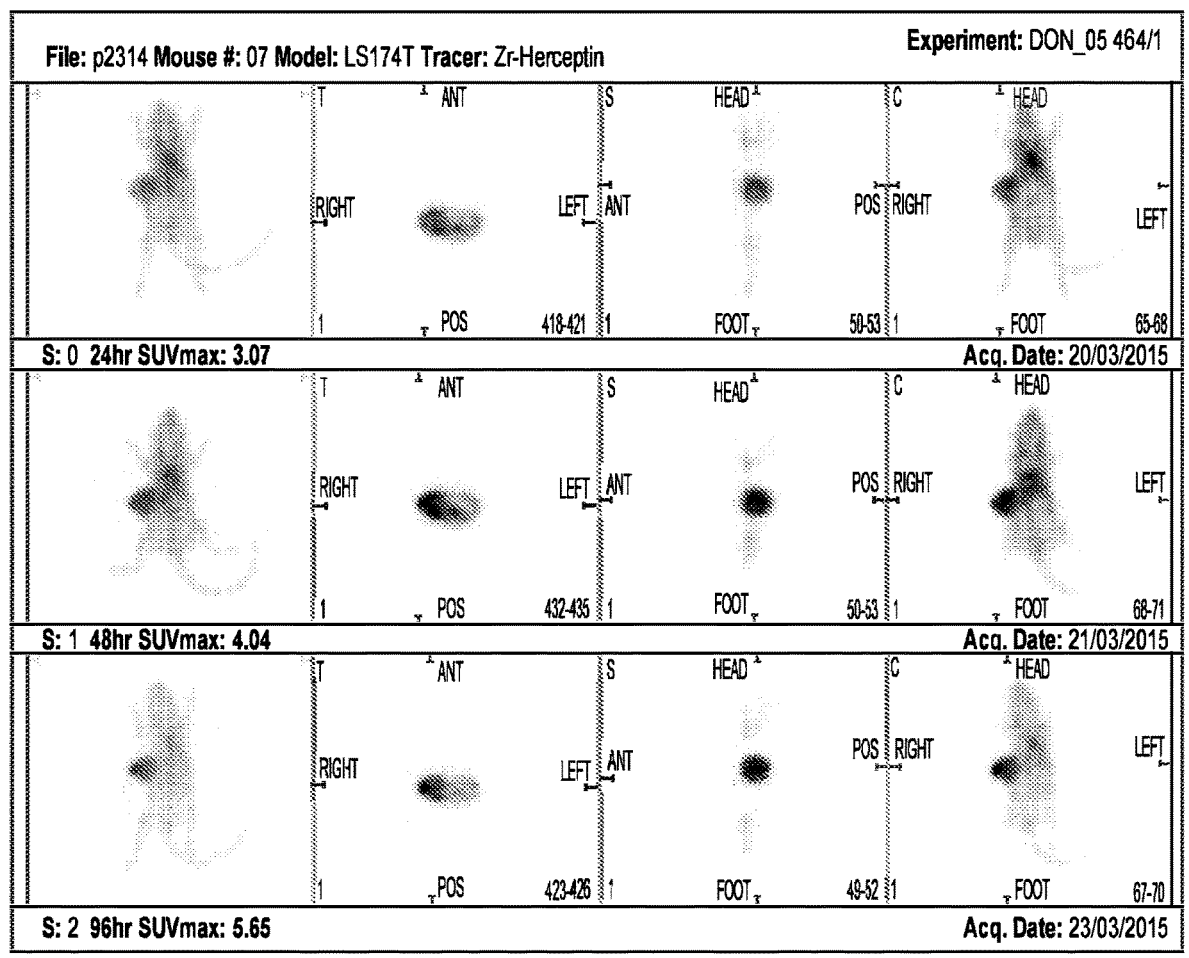
Figure 30:
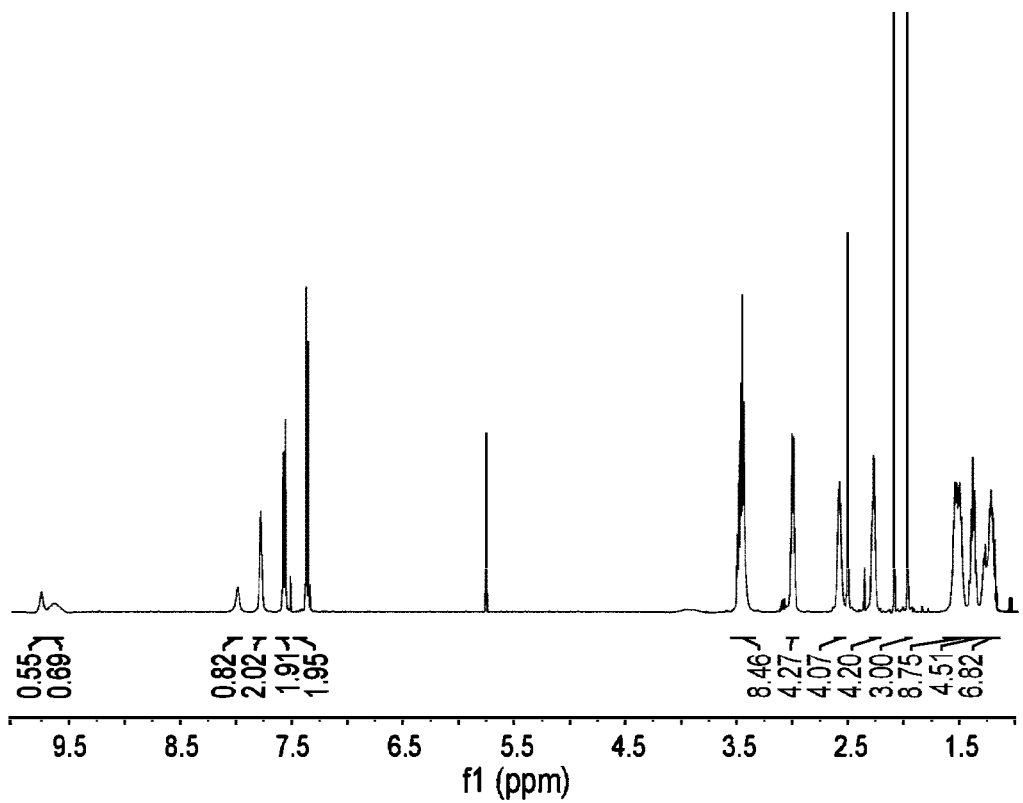
FIG. 30. $^1$H NMR analysis of DFOPhNCS ($d_6$-DMSO, 400 MHz).
Figure 31:
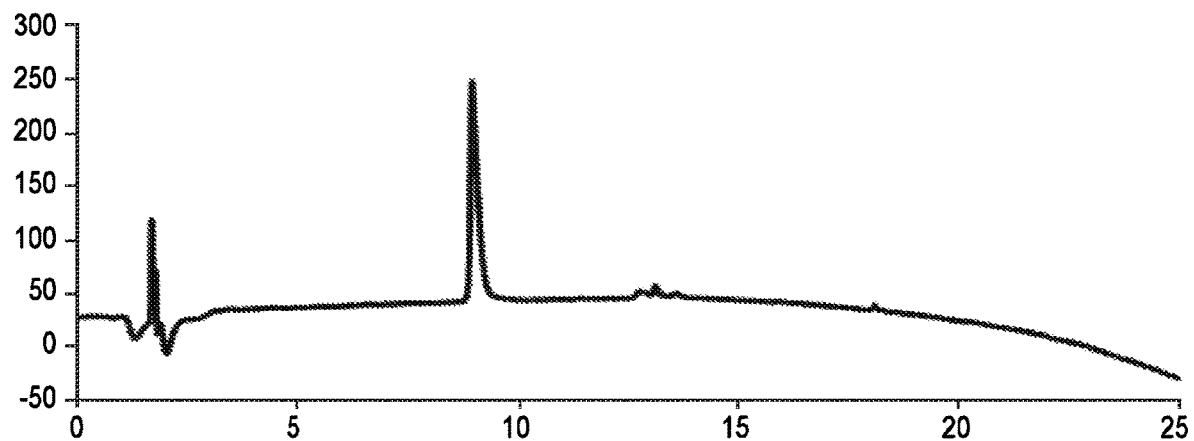
FIG. 31. Analytical HPLC trace (absorbance at 214 nm) of purified DFOPhNCS (signal at 1.5 min=DMSO, 8.95 min=DFOPhNCS).
Figure 32:
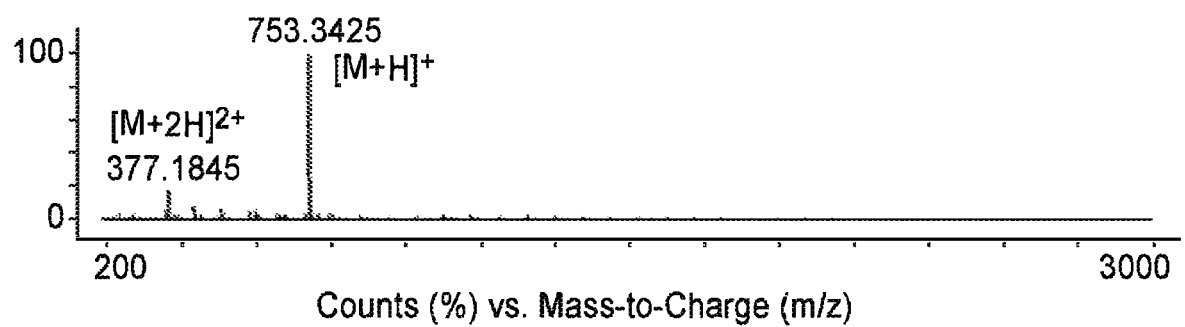
FIG. 32. ESI-MS analysis of purified DFOPhNCS.
Figure 33:
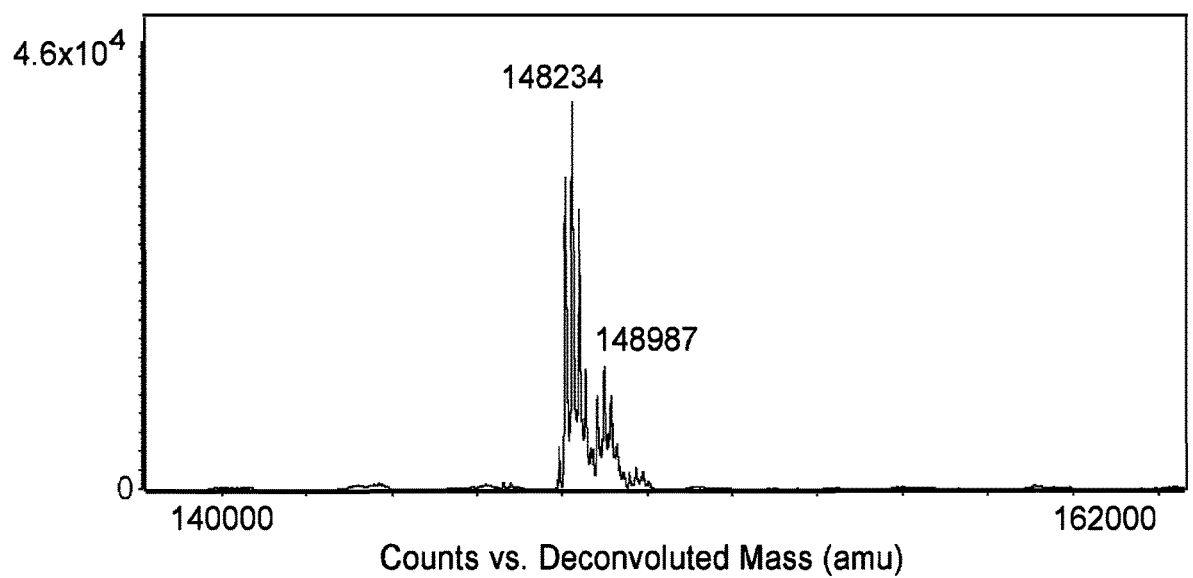
FIG. 33. Deconvoluted ESI-MS of DFOPhNCS-trastuzumab (unlabelled trastuzumab=148,234; trastuzumab with one DFOPhNCS attachment=148,987).
Figure 34A:
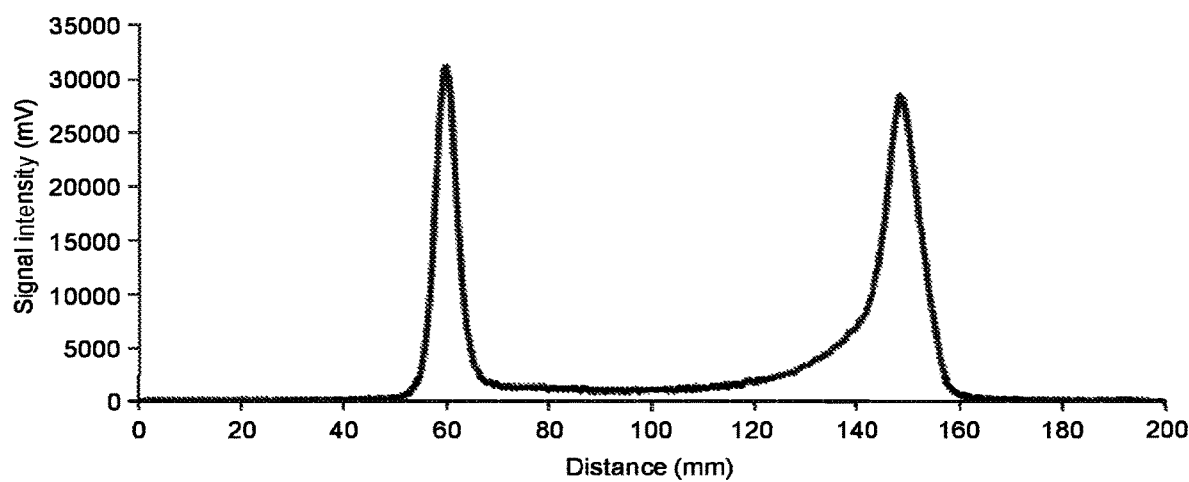
FIGS. 34A-34C.
Figure 34B:
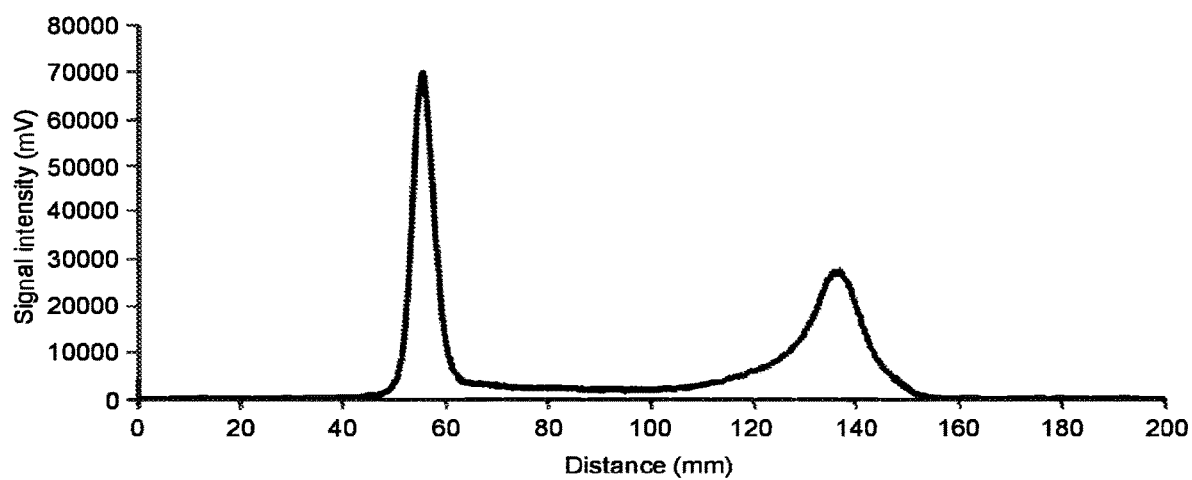
Figure 34C:
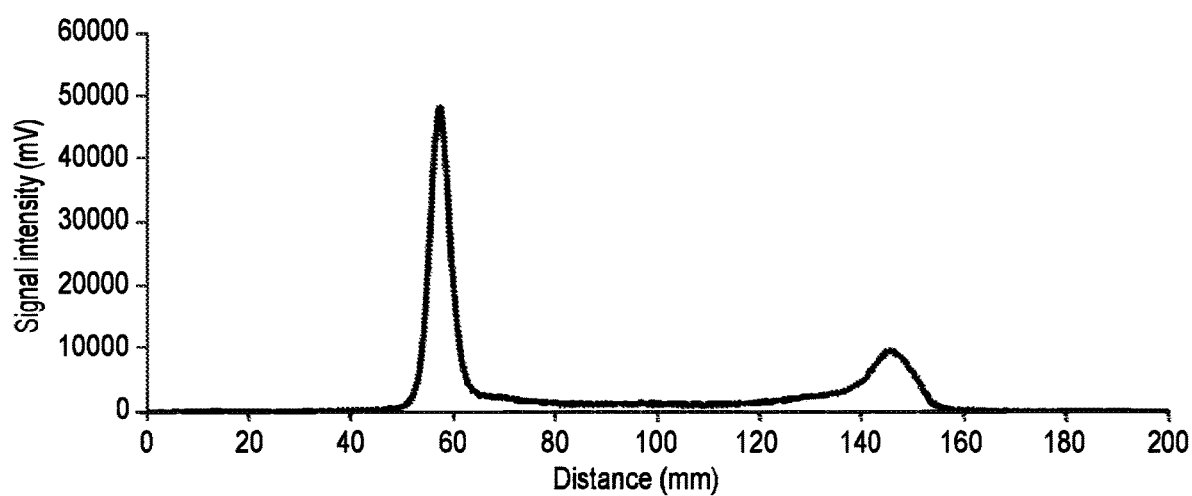
Figure 35:
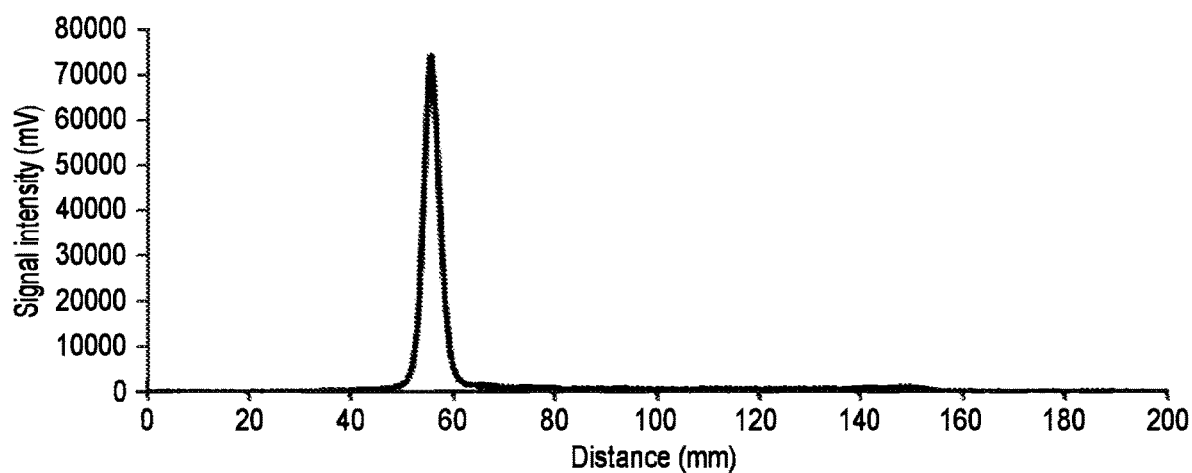
FIG. 35. iTLC analysis of $^{89}$Zr-DFOPhNCS-trastuzumab after PD-10 purification (origin is at 55 mm, solvent front at 150 mm; labelled trastuzumab remains at the origin, activity with a distance of >70 mm (r.f.>0.1) represents non-chelated $^{89}$Zr).
Figure 36A:
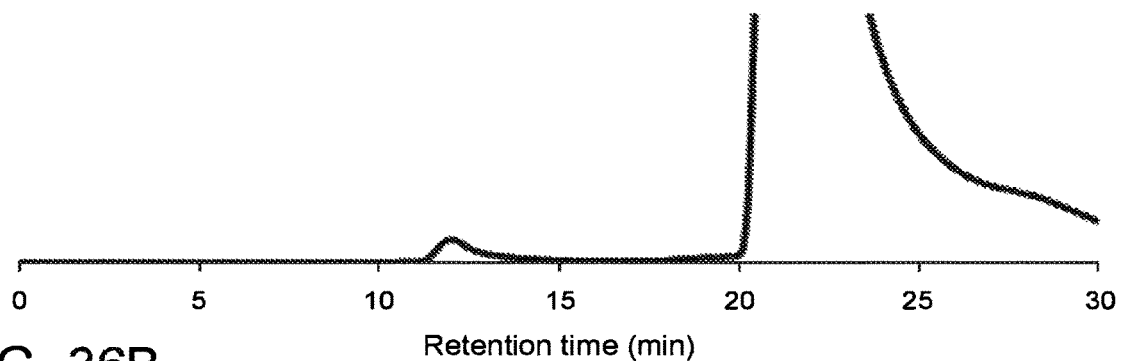
FIGS. 36A-36B. SEC-HPLC analysis of $^{89}$Zr-DFOPhNCS-trastuzumab after PD-10 purification (FIG. 36A: absorbance at 280 nm.
Figure 36B:
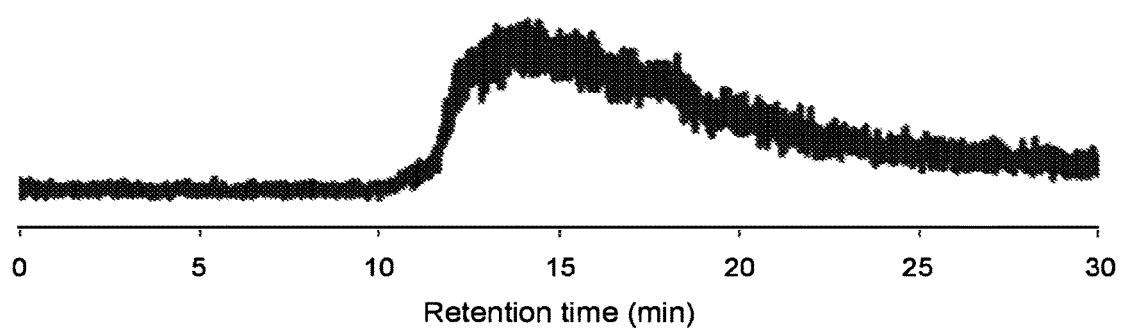
Figure 37:
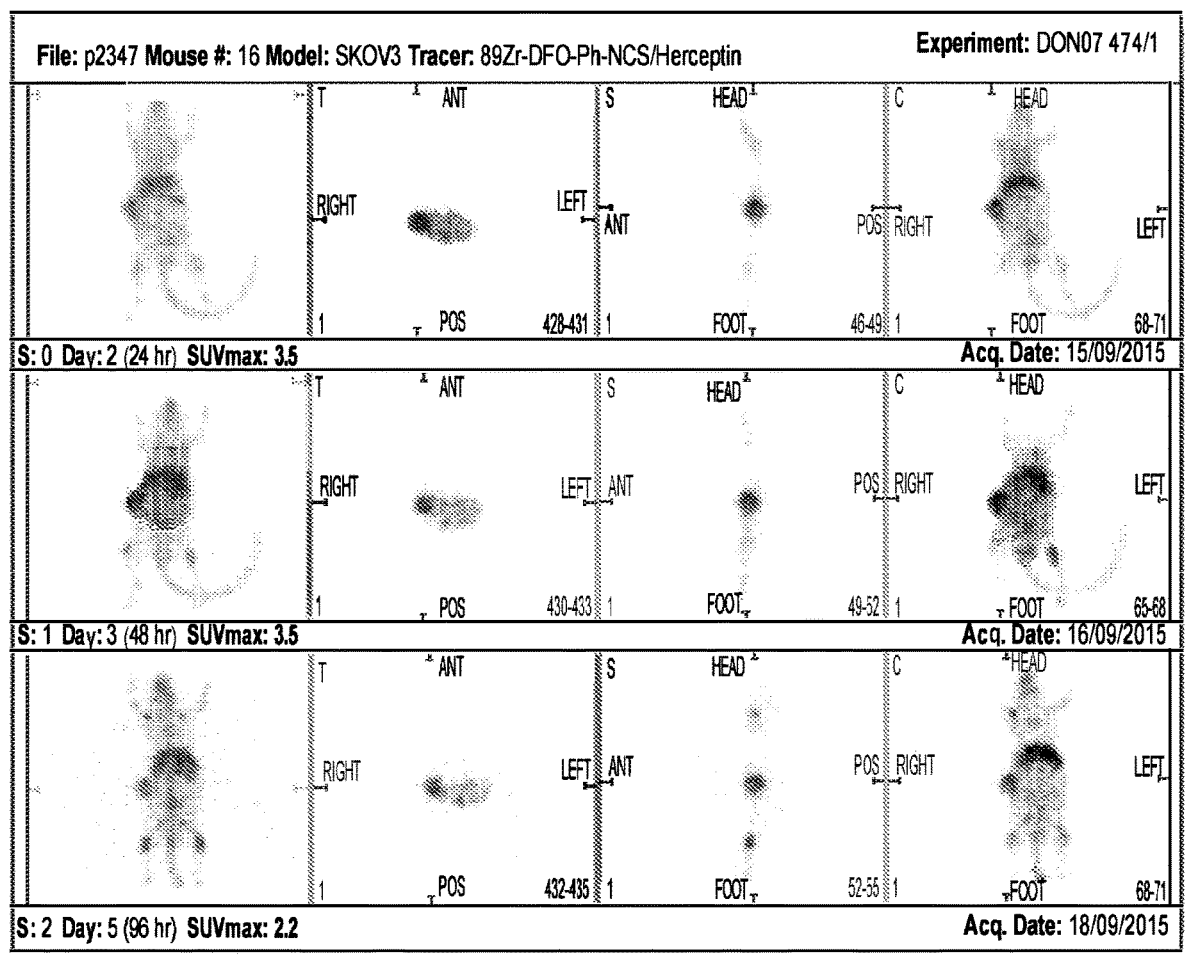
FIG. 37. PET imaging of SKOV3 tumour bearing mice using $^{89}$Zr-DFOPhNCS-trastuzumab as the imaging agent.
Figure 37:
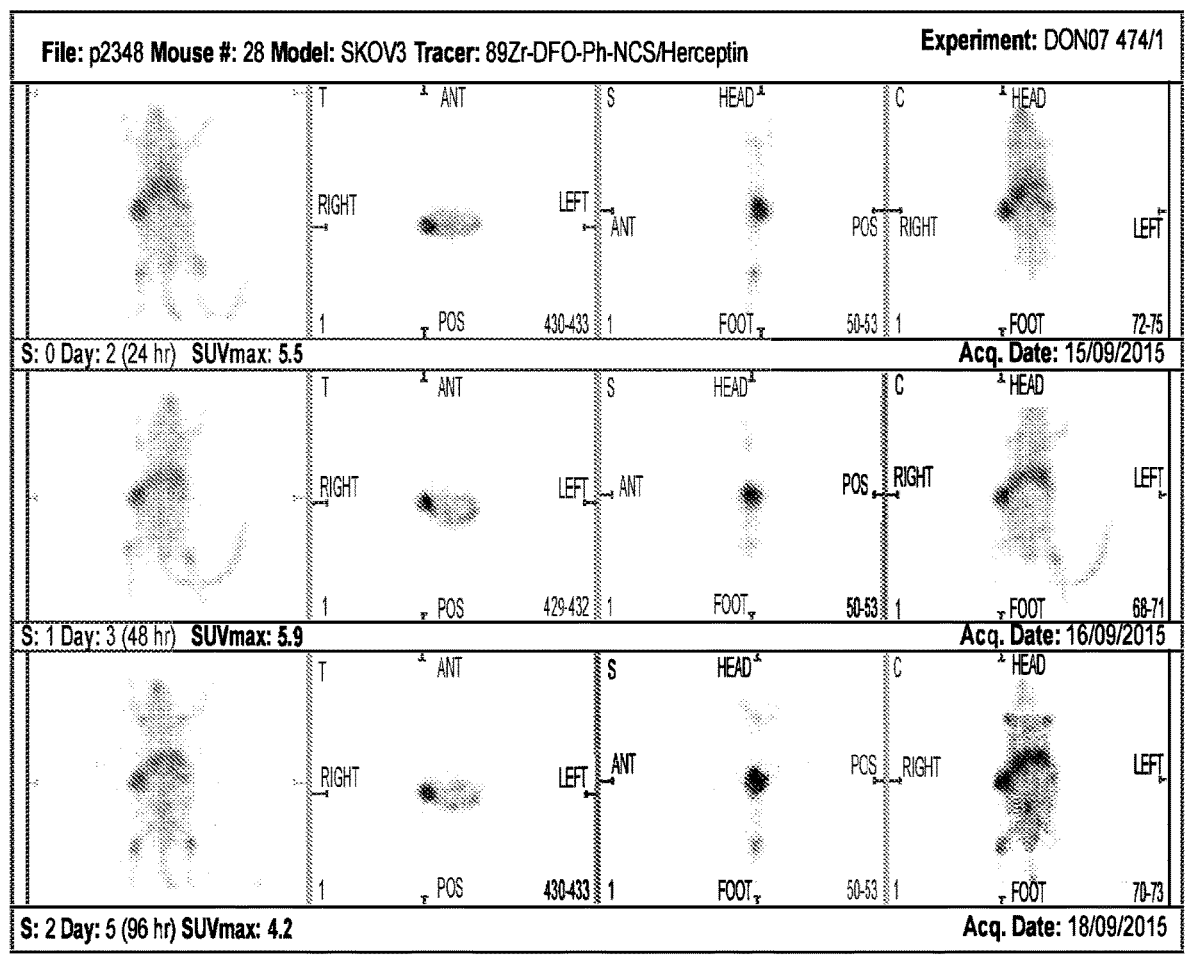
Figure 37:
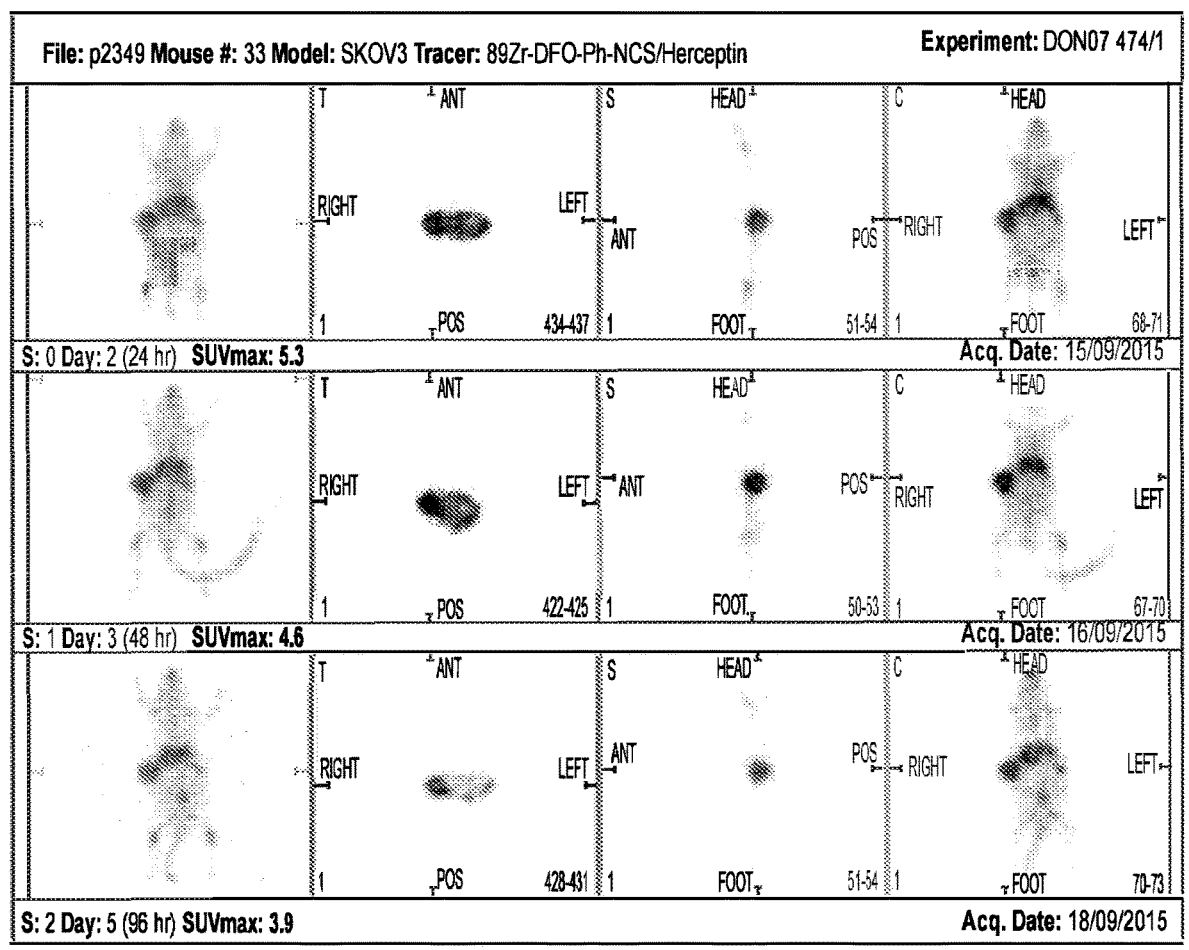

This specificity and stability of the conjugate of the present invention is also illustrated in FIGS. 28 and 29, which demonstrate the imaging ability of $^{89}Zr(DFOSq$-trastuzumab) in respect of other HER2-positive tumours (LS174T, which is a colorectal tumour model, and SKOV3, which is an ovarian cancer model). The results obtained with $^{89}Zr(DFOSq$-trastuzumab) in the SKOV3 tumour model (FIG. 28) can also be qualitatively contrasted with those obtained in the same tumour model but using $^{89}$Zr(DFO-PhNCS-trastuzumab) as the imaging agent (see FIG. 37), which shows significant distribution of the radionuclide throughout the treated mice.

The superior activity of the radiolabelled conjugate of the present invention over other conjugates, such as $^{89}$Zr(DFO-PhNCS-trastuzumab) is also demonstrated by the Standardized Uptake Values (SUVs) obtained from the imaging of SKOV3 tumours using $^{89}$Zr(DFO-squarate-trastuzumab) (see Table 3 in the Examples) compared with the SUVs obtained from the imaging of SKOV3 tumours using $^{89}$Zr(DFO-PhNCS-trastuzumab) (see Table 7 in the Examples). SUV is basically the tissue radioactivity concentration (at time point t), divided by the injected activity divided by the body weight of the animal. Therefore, the SUV standardises for different amounts of radioactivity injected and the size of the animal.

Figure 38:
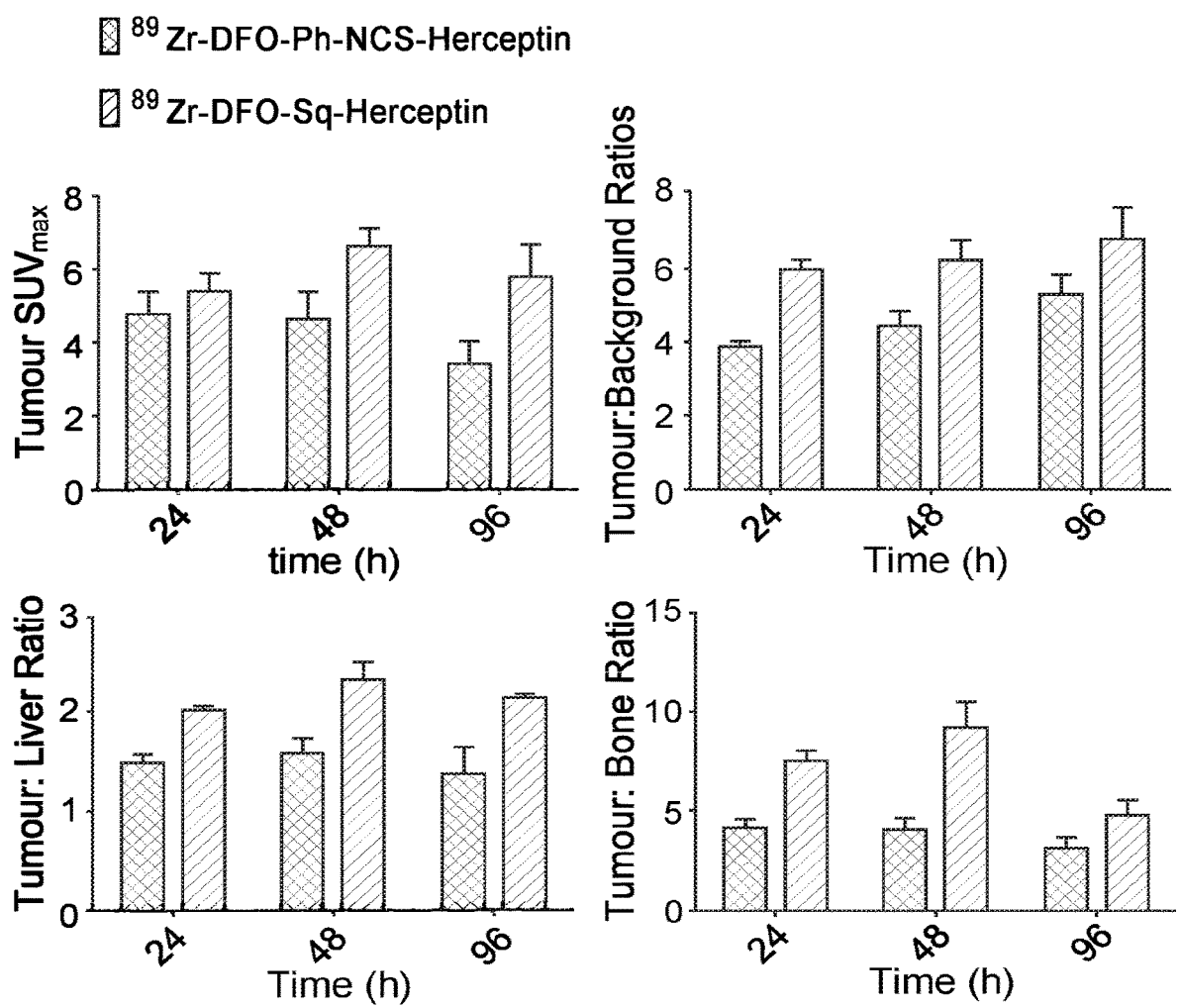
FIG. 38. PET imaging results of $^{89}$Zr-DFO-Sq/Herceptin vs $^{89}$Zr-DFO-Ph-NCS/Herceptin uptake in SKOV3 tumour-bearing mice.

In general, the best images (and less radio toxicity to non-target organs) are obtained when the ratio of radioimaging agent uptake in a tumour to the uptake of the agent by non-target tissue (such as bone and the liver) is higher. The higher the ratio, the better the image and selectivity of the radioimaging agent. The graphs in FIG. 38 show the tumour $SUV_{max}$, as well as the SUV ratio for tumour:background, tumour:liver and tumour:bone, for a radiolabelled conjugate of the present invention ($^{89}$Zr(DFOSq-trastuzumab)), and $^{89}$Zr(DFO-PhNCS-trastuzumab). From FIG. 38, it can be seen that the SUV ratio of $^{89}$Zr(DFOSq-trastuzumab is higher across all experiments than the SUV ratio of $^{89}$Zr(DFO-PhNCS-trastuzumab) because there is more radioactivity at the target site than in the other tissue (liver and bone). This demonstrates that the radiolabelled conjugate of the present invention is a more selective and stable agent than $^{89}$Zr(DFO-PhNCS-trastuzumab). The high tumour:background ratio is advantageous.

Notably, the uptake of the radiolabelled conjugate of the present invention is also dependent on the HER2 expression level of the tumours. The data presented here demonstrate that tumours that have a high HER2 expression level (such as BT474) have greater uptake of the conjugate (and therefore produce a stronger PET image) than tumours that have a lower level of HER2 expression (e.g. LS174T, which will result in a "dimmer" image). This difference in image strength as a result of varying the HER2 expression level is a strong indication that it is the HER2 expression level on a tumour that influences the strength of the PET image obtained, not the presence of different metabolites, As used herein, the term "radionuclide" (also commonly referred to as a radioisotope or radioactive isotope), is an atom with an unstable nucleus. It radioactively decays resulting in the emission of nuclear radiation (such as gamma rays and/or subatomic particles such as alpha or beta particles). In one embodiment, the radionuclide is one that is also useful in radioimmunotherapy applications (e.g. a beta particle emitter). Preferably, the radionuclide has eight-coordinate geometry. Examples of radionuclides suitable for use in the present invention include radioisotopes of zirconium (e.g. $^{89}$Zr), gallium (e.g. $^{67}$Ga and $^{68}$Ga), lutetium (e.g. $^{176}$Lu and $^{177}$Lu), holmium (e.g. $^{166}$Ho), scandium (e.g. $^{44}$Sc and $^{47}$Sc), titanium (e.g. $^{45}$Ti), indium (e.g. $^{111}$In and $^{115}$In), yttrium (e.g. $^{86}$Y and $^{90}$Y), terbium e.g. ($^{149}$Tb, 152Tb, $^{155}$Tb and $^{161}$Tb), technetium (e.g. $^{99m}$Tc), samarium (e.g. $^{153}$Sm) and niobium (e.g. $^{95}$Nb and $^{90}$Nb). The radionuclide for use in the present invention may be selected from gallium (specifically, $^{67}$Ga and $^{68}$Ga), indium (specifically, $^{111}$In), and zirconium (specifically, $^{89}$Zr). The radionuclide for use in the present invention may be selected from $^{68}$Ga, $^{111}$In and $^{89}$Zr. For example, $^{68}$Ga has been shown to bind with DFO (see Ueda et al (2015) *Mol Imaging Biol*, vol. 17, pages 102-110), and indium has similar co-ordination chemistry to zirconium (and therefore would be expected to bind to the compound of formula (I) in a similar way).

It will be understood by a person skilled in the art that the compound of the present invention can also complex non-radioactive metals used in imaging applications, such as MRI. An example of such a metal is gadolinium (e.g. $^{152}$Gd).

As mentioned above, the present invention also relates to a conjugate of a compound of formula (I), or a pharmaceutically-acceptable salt thereof, and a target molecule.

As used herein, the term "target molecule" refers to a biological molecule, or a fragment of a biological molecule, that has the ability to target a particular tissue or tumour. The target molecule may be a polypeptide, such as a protein (e.g. a transport protein such as transferrin), an albumin (e.g. serum albumin) or an antibody (e.g. trastuzumab, also known as herceptin, ranibizumab, bevacizumab, fresolimumab, cetuximab, panitumumab, rituximab, pertuzumab, and ofatumumab). The antibody may be selected from Herceptin, rituximab and cetuximab. The target molecule may be a peptide (e.g. a targeting peptide that is used to target cells involved in tumour angiogenesis, such as cyclic RGD sequences, or another targeting peptide, such as octreotate, bombesin and glu-N(CO)N-lys PSMA). The target molecule will have a functional group (such as an amine group of a lysine residue) that will react with the squarate moiety to form a covalent link between the target molecule and the compound of formula (I). This results in formation of the conjugate. The conjugate may also include a radionuclide complexed thereto. This produces a radionuclide-labelled conjugate of a compound of formula (I), or a pharmaceutically-acceptable salt thereof, a target molecule, and a radionuclide complexed thereto. In one embodiment, the radionuclide is a radioisotope of zirconium (e.g. $^{89}$Zr).

The compounds of formula (I) and the radionuclide complexes can be synthesised by any suitable method known to a person skilled in the art. An example of a synthetic method is given below in Scheme 1.

Scheme 1

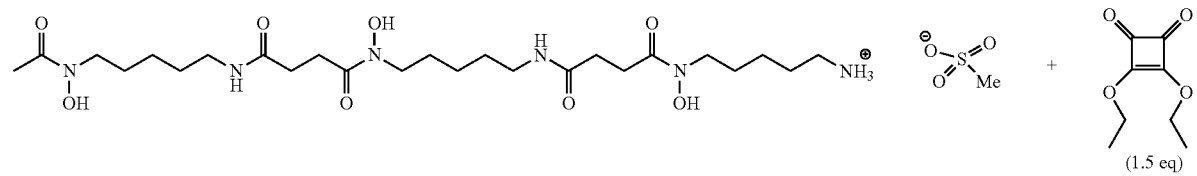

(1.5 eq)

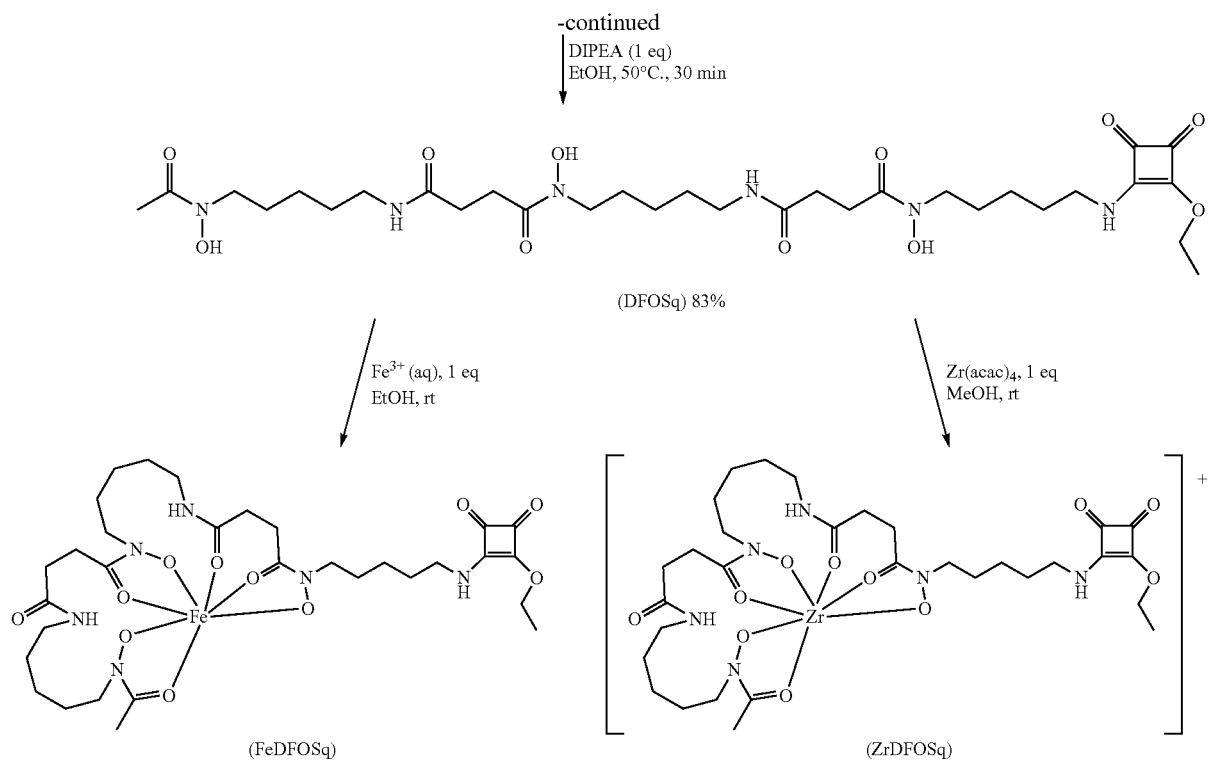

(DFOSq) 83%

(FeDFOSq)  (ZrDFOSq)

The radionuclide complexes can be conjugated with the target molecules of interest (to produce a radiolabelled conjugate) by any suitable method known to a person skilled in the art. An example of a suitable method is set out as follows:

1. Prepare target molecule in borate buffer, pH 9, at a concentration such that the final buffer concentration of the reaction mixture is 0.5 M.
2. Prepare DFOSq solution in 4% DMSO in MilliQ water (DMSO should be added first to ensure the DFOSq is fully dissolved).
3. DFOSq solution should be added to the target molecule as required and the reaction mixture left to stand at room temperature overnight (shorter reaction times will result in lower average chelators per target molecule).
4. Conjugates can be purified using spin filters with an appropriate molecular weight limit (at least 1 kDa). After initial filtration the conjugate should be washed on the spin filter at least twice with 4% DMSO in MilliQ to remove all excess DFOSq.
5. A buffer exchange step using the spin filter then allows for storage of the conjugate (0.9% NaCl solution is recommended for DFOSq-Herceptin).

It will also be clear to a person skilled in the art that the conjugate can be prepared in the absence of the radionuclide. In this embodiment, the radionuclide is added to the conjugate once the conjugate has been prepared.

The present invention also relates to pharmaceutical compositions including a radionuclide-labelled conjugate of:

a compound of formula (I):

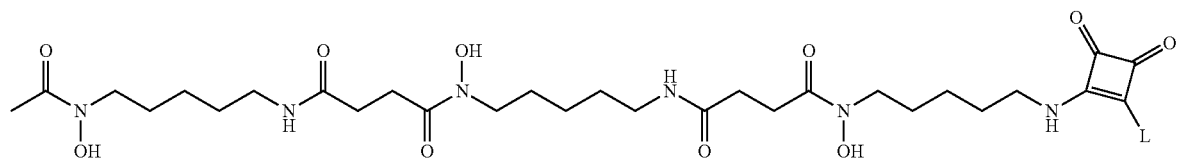

(I)

or a pharmaceutically-acceptable salt thereof, wherein L is a leaving group (as defined herein), a target molecule, and a radionuclide complexed thereto, and one or more pharmaceutically acceptable carrier substances, excipients and/or adjuvants.

Pharmaceutical compositions may include, for example, one or more of water, buffers (for example, neutral buffered saline, phosphate buffered saline, citrates and acetates), ethanol, oil, carbohydrates (for example, glucose, fructose, mannose, sucrose and mannitol), proteins, polypeptides or amino acids such as glycine, antioxidants (e.g. sodium bisulfite), tonicity adjusting agents (such as potassium and calcium chloride), chelating agents such as EDTA or glutathione, vitamins and/or preservatives.

Pharmaceutical compositions will preferably be formulated for parenteral administration. The term "parenteral" as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. Intravenous administration is preferred. Suitable components of parenteral formulations, and methods of making such formulations, are detailed in various texts, including "Remington's Pharmaceutical Sciences".

The composition of the present invention will be administered to a patient parenterally in the usual manner. The DFO-squaramide conjugate complex may then take anywhere from 1 hour to 24 hours to distribute throughout the body to the target site. Once the desired distribution has been achieved, the patient will be imaged.

Accordingly, the present invention also relates to a method of imaging a patient, the method including:
  administering to a patient the radionuclide-labelled conjugate, as defined herein; and
  imaging said patient.

The present invention also relates to a method of imaging a cell or in vitro biopsy sample, the method including:
  administering to a cell or in vitro biopsy sample the radionuclide-labelled conjugate, as defined herein; and
  imaging the cell or in vitro biopsy sample.

Preferably, the target molecule serves to target the conjugate to a desired site in vivo, or to a desired site in the cell or in the biopsy sample. Preferably, the desired site is a tumour.

It will be understood, that the specific dose level for any particular patient, and the length of time that the agent will take to arrive at the target site, will depend upon a variety of factors including the activity of the specific compound employed, the age, body weight, general health, sex, diet, time of administration, route of administration, and rate of excretion, and the severity of the particular disorder undergoing therapy.

The term "effective amount" refers to an amount of the that results in a detectable amount of radiation following administration of the radionuclide-labelled conjugate to a patient. A person skilled in the art will know how much of the radionuclide-labelled conjugate to administer to a patient to achieve the optimal imaging capability without causing problems from a toxicity perspective. The radionuclide-labelled conjugates of the present invention find particular use in assisting clinicians to determine where a cancer is (including whether a target, such a receptor, is homogeneously present on a tumour), what treatment a cancer will respond to (which facilitates treatment selection and determination of optimal dosages), and how much of the treatment will ultimately reach the target site. The radionuclide-labelled conjugates of the present invention can also be used to study the pharmacokinetics and biodistribution of particular target molecules (e.g. during drug development of new biological therapeutic agents, such as monoclonal antibodies).

Patients may include but are not limited to primates, especially humans, domesticated companion animals such as dogs, cats, horses, and livestock such as cattle, pigs and sheep, with dosages as described herein.

As mentioned above, the radionuclide-labelled conjugates of the present invention are particularly useful for imaging tumours (which form as a result of uncontrolled or progressive proliferation of cells). Some such uncontrolled proliferating cells are benign, but others are termed "malignant" and may lead to death of the organism. Malignant neoplasms or "cancers" are distinguished from benign growths in that, in addition to exhibiting aggressive cellular proliferation, they may invade surrounding tissues and metastasize. Moreover, malignant neoplasms are characterized in that they show a greater loss of differentiation (greater "dedifferentiation"), and greater loss of their organization relative to one another and their surrounding tissues. This property is also called "anaplasia". Neoplasms treatable by the present invention also include solid phase tumors/malignancies, i.e. carcinomas, locally advanced tumors and human soft tissue sarcomas. Carcinomas include those malignant neoplasms derived from epithelial cells that infiltrate (invade) the surrounding tissues and give rise to metastastic cancers, including lymphatic metastases.

Adenocarcinomas are carcinomas derived from glandular tissue, or which form recognizable glandular structures. Another broad category of cancers includes sarcomas, which are tumors whose cells are embedded in a fibrillar or homogeneous substance like embryonic connective tissue.

The type of cancer or tumor cells that may be amenable to imaging according to the invention include, for example, breast, colon, lung, and prostate cancers, gastrointestinal cancers including esophageal cancer, stomach cancer, colorectal cancer, polyps associated with colorectal neoplasms, pancreatic cancer and gallbladder cancer, cancer of the adrenal cortex, ACTH-producing tumor, bladder cancer, brain cancer including intrinsic brain tumors, neuroblastomas, astrocytic brain tumors, gliomas, and metastatic tumor cell invasion of the central nervous system, Ewing's sarcoma, head and neck cancer including mouth cancer and larynx cancer, kidney cancer including renal cell carcinoma, liver cancer, lung cancer including small and non-small cell lung cancers, malignant peritoneal effusion, malignant pleural effusion, skin cancers including malignant melanoma, tumor progression of human skin keratinocytes, squamous cell carcinoma, basal cell carcinoma, and hemangiopericytoma, mesothelioma, Kaposi's sarcoma, bone cancer including osteomas and sarcomas such as fibrosarcoma and osteosarcoma, cancers of the female reproductive tract including uterine cancer, endometrial cancer, ovarian cancer, ovarian (germ cell) cancer and solid tumors in the ovarian follicle, vaginal cancer, cancer of the vulva, and cervical cancer, breast cancer (small cell and ductal), penile cancer, retinoblastoma, testicular cancer, thyroid cancer, trophoblastic neoplasms, and Wilms' tumor.

It may also be advantageous to administer the radionuclide-labelled conjugates of the present invention with drugs that have anti-cancer activity. Examples of suitable drugs in this regard include fluorouracil, imiquimod, anastrozole, axitinib, belinostat, bexarotene, bicalutamide, bortezomib, busulfan, cabazitaxel, capecitabine, carmustine, cisplatin, dabrafenib, daunorubicin hydrochloride, docetaxel, doxorubicin, eloxati, erlotinib, etoposide, exemestane, fulvestrant, methotrexate, gefitinib, gemcitabine, ifosfamide, irinotecan, ixabepilone, lanalidomide, letrozole, lomustine, megestrol acetate, temozolomide, vinorelbine, nilotinib, tamoxifen, oxaliplatin, paclitaxel, raloxifene, pemetrexed, sorafenib, thalidomide, topotecan, vermurafenib and vincristine.

The radionuclide-labelled conjugates of the present invention can also be used to determine whether a particular tumour has one or more types of receptor, and therefore whether a patient may benefit from a particular therapy. For example, by using herceptin as a target molecule in the radiolabelled conjugate, the presence of HER2 receptors on a patient's tumour can be tested for. If the tumour is HER2-negative (i.e. does not have HER2 receptors), the imaging agent will not "stick" to the tumour, indicating that herceptin may not be a useful therapy for the patient.

It will be understood that the invention disclosed and defined in this specification extends to all alternative combinations of two or more of the individual features mentioned or evident from the text or drawings. All of these different combinations constitute various alternative aspects of the invention.

EXAMPLES

All reagents and solvents were obtained from standard commercial sources and unless otherwise stated were used as received.

$^1$H and $^{13}$C spectra were recorded with a Varian FT-NMR 400 or Varian FT-NMR 500 (Varian, California USA). $^1$H-NMR spectra were acquired at 400 or 500 MHz and $^{13}$C-NMR spectra were acquired at 101 or 125 MHz. All NMR spectra were recorded at 25° C. unless otherwise stated. The reported chemical shifts (in parts per million) are referenced relative to residual solvent signal.

ESI-MS of non-protein samples were recorded on an Agilent 6510 ESI-TOF LC/MS Mass Spectrometer (Agilent, California USA).

Analytical reverse phase HPLC was performed on an Agilent 1100 Series. Protein samples were analysed using an Agilent 6220 ESI-TOF LC/MS Mass Spectrometer coupled to an Agilent 1200 LC system (Agilent, Palo Alto, Calif.). All data were acquired and reference mass corrected via a dual-spray electrospray ionisation (ESI) source. Acquisition was performed using the Agilent Mass Hunter Acquisition software version B.02.01 (B2116.30). Ionisation mode: Electrospray Ionisation; Drying gas flow: 7 L/min; Nebuliser: 35 psi; Drying gas temperature: 325° C.; Capillary Voltage (Vcap): 4000 V; Fragmentor: 300 V; Skimmer: 65 V; OCT RFV: 250 V; Scan range acquired: 300-3200 m/z Internal Reference ions: Positive Ion Mode=m/z=121.050873 & 922.009798.

Protein desalting and chromatographic separation was performed using an Agilent Poroshell C18 2.1×75 mm, 5 μm column using 5% (v/v) acetonitrile ported to waste (0-5 min). Upon desalting of sample the flow was ported back into the ESI source for subsequent gradient elution with (5% (v/v) to 100% (v/v)) acetonitrile/0.1% formic acid over 8 min at 0.25 mL/min. Analysis was performed using Mass Hunter version B.06.00 with BioConfirm software using the maximum entropy protein deconvolution algorithm; mass step 1 Da; Baseline factor 3.00; peak width set to uncertainty.

Size exclusion HPLC was performed on a Shimadzu SCL-10A VP/LC-10 AT VP system with a Shimadzu SPD-10A VP UV detector followed by a radiation detector (Ortec model 276 photomultiplier base with preamplifier, Ortec 925-SCINT ACE mate preamplifier, BIAS supply and SCA, Bicron 1M 11/2 photomultiplier tube). A Biosuite 125 HR SEC 5 μm 7.8×300 mm column was used with a flow rate of 0.6 mL/min and Dulbecco's PBS with 5% isopropanol as eluent. Radio-iTLC were analysed using a Raytest Rita-Star TLC scanner.

Synthesis of DFO-Squaramide (DFOSq)

DFO (mesylate) +

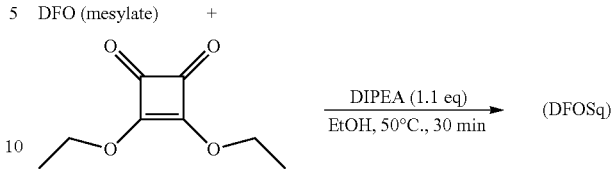

$\xrightarrow[\text{EtOH, 50°C., 30 min}]{\text{DIPEA (1.1 eq)}}$ (DFOSq)

A mixture of Desferrioxamine B mesylate (0.20 g, 0.31 mmol) and DIPEA (0.05 mL, 0.3 mmol) was stirred in EtOH (6 mL) at 50° C. After 1 h, 3,4-diethoxy-3-cyclobutene-1,2-dione (0.1 mL, 0.7 mmol) in EtOH (9 mL) was added. After a further 30 mins of stirring at 50° C. the solvent was removed under reduced pressure, and the residue was triturated with EtOH (3×10 mL). The product was dried in vacuo to give DFOSq as a white powder (0.17 g, 83%).

$^1$H NMR (d$_6$-DMSO, 500 MHz) δ 9.61 (s, 6H), 8.77 (t, J=5.8 Hz, 1H), 8.58 (t, J=5.7 Hz, 1H), 7.77 (d, J=4.7 Hz, 5H), 4.64 (p, J=6.9 Hz, 5H), 3.45 (t, J=7.0 Hz, 3H), 3.38 (s, 5H), 3.26 (dd, J=13.0, 6.6 Hz, 1H), 3.00 (dd, J=12.7, 6.4 Hz, 10H), 2.56 (d, J=6.5 Hz, 1H), 2.26 (t, J=7.2 Hz, 1H), 1.96 (s, 7H), 1.50 (d, J=6.6 Hz, 3H), 1.42-1.31 (m, 3H), 1.24 (ddd, J=20.2, 14.7, 8.0 Hz, 2H); $^{13}$C NMR (d$_6$-DMSO, 101 MHz) δ 189.39, 189.30, 182.05, 181.84, 176.93, 176.47, 172.58, 172.17, 171.97, 171.30, 170.13, 70.18, 68.77, 68.73, 47.09, 47.01, 46.79, 43.68, 43.39, 39.52, 38.42, 30.10, 29.90, 29.60, 28.82, 27.56, 26.04, 25.82, 23.50, 22.92, 20.35, 15.64; HRMS ESI [M+H$^+$]: 685.3768, calculated for (C$_{31}$H$_{53}$N$_6$O$_{11}$)$^+$: 685.3767, [M+Na$^+$]: 707.3589, calculated for (C$_{31}$H$_{52}$NaN$_6$O$_{11}$)$^+$: 707.3586.

Radiolabelling

Aqueous Na$_2$CO$_3$ (2 M, 4.5 μL) was added to a solution of $^{89}$Zr in 1 M oxalic acid (10 MBq, 10 μL) until the pH increased to 10. HEPES buffer (0.5 M, pH 7, 50 μL) was then added and the solution allowed to stand for 5 min. Neutral pH was confirmed, and then a solution of DFOSq in DMSO (1 μL, 0.18 μmol) was added. After 1 h, reaction completion was confirmed by radio-iTLC (Silica infused glass fiber plate, 20 mM pH 5 citrate buffer, product R$_f$=0) and SEHPLC (BioSuite 125, 5 μm HR SEC 7.8×300 mm column, 20 mM pH 7 Dulbecco's PBS with 5% i-PrOH as eluent, 0.6 mL/min, product retention time 21.80 min).

Radio-iTLC

Figure 4:
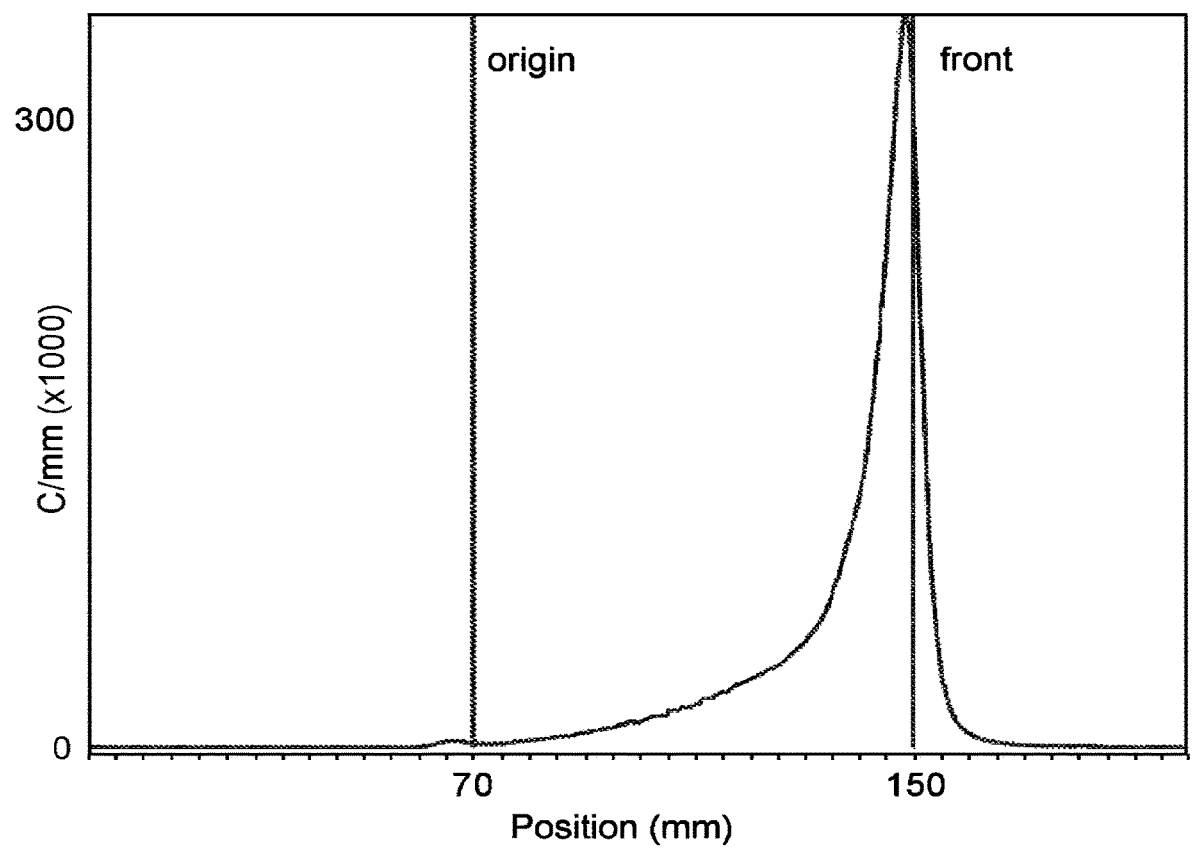
FIG. 4. A radio-iTLC chromatogram of a control sample (i.e. no DFOSq).

The chromatogram of the control (i.e. no DFOSq) is shown in FIG. 4. This shows that the zirconium-containing solution moves with the solvent front (as expected) when DFOSq is not present.

Figure 5:
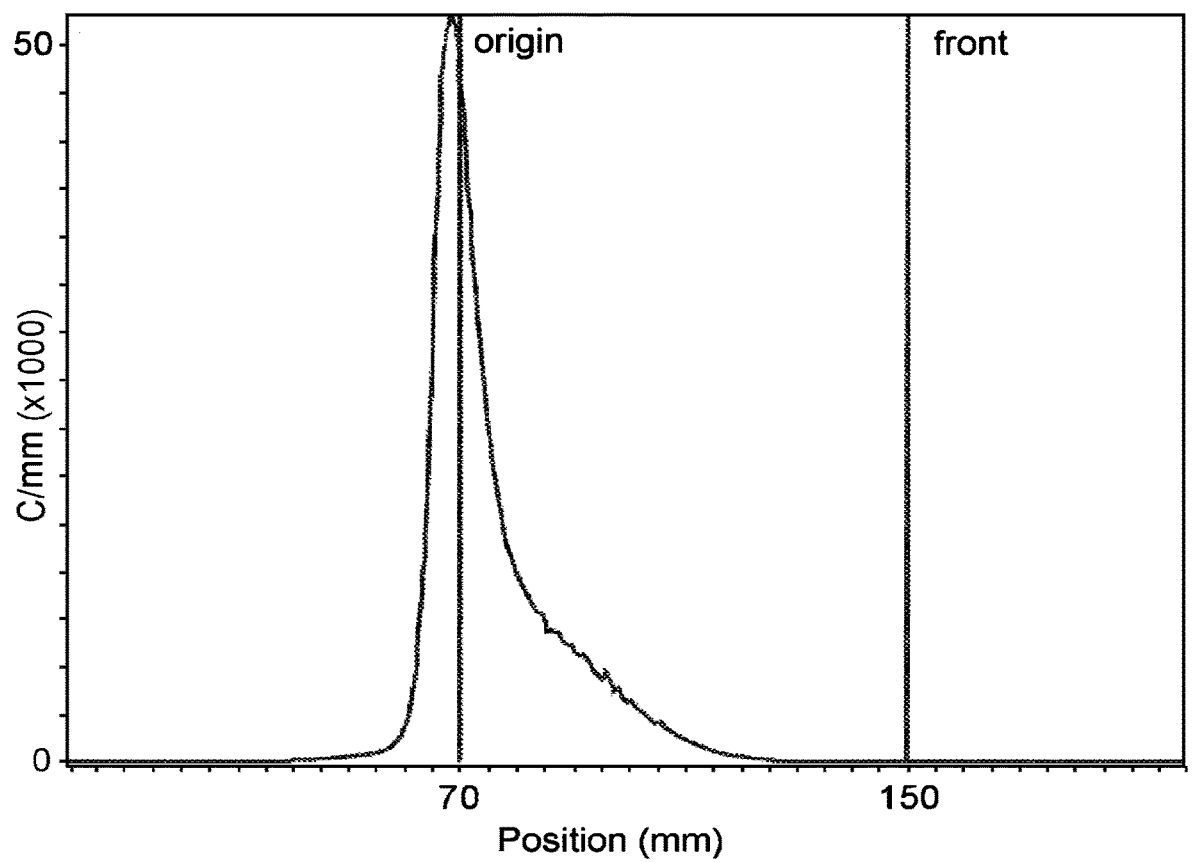
FIG. 5. A radio-iTLC chromatogram of the $^{89}$Zr DFOSq complex (60 minutes after addition of $^{89}$Zr).

The chromatogram of the $^{89}$Zr DFOSq complex (60 minutes after addition of $^{89}$Zr) is shown in FIG. 5. This shows that the zirconium has now been retained on the base line (i.e. the "origin") by virtue of it being complexed to DFOSq.

Size Exclusion HPLC

Figure 6A:
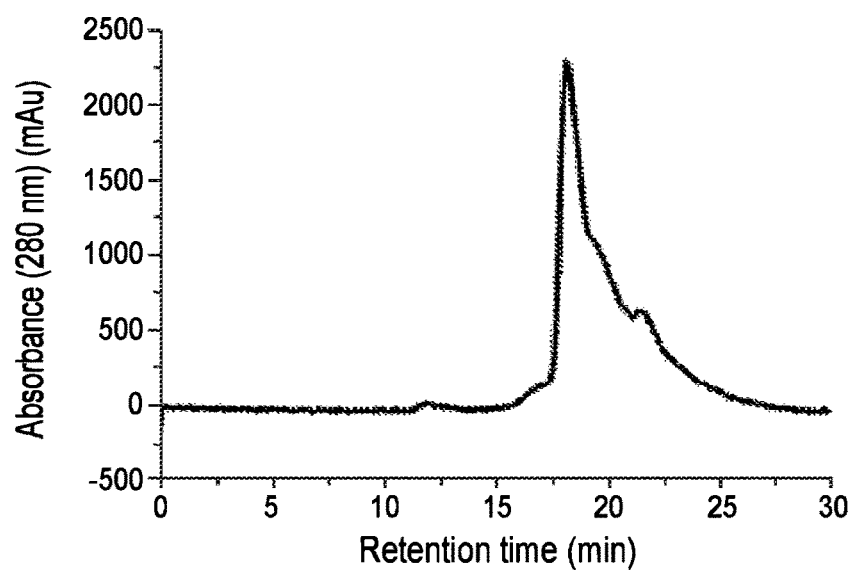
FIGS. 6A-6C. Two Size Exclusion HPLC UV-Vis chromatograms (at two different absorption wavelengths of 280 (FIG. 6A) and 254 nm (FIG. 6B)) and a radiation chromatogram of a control sample (FIG. 6C).
Figure 6B:
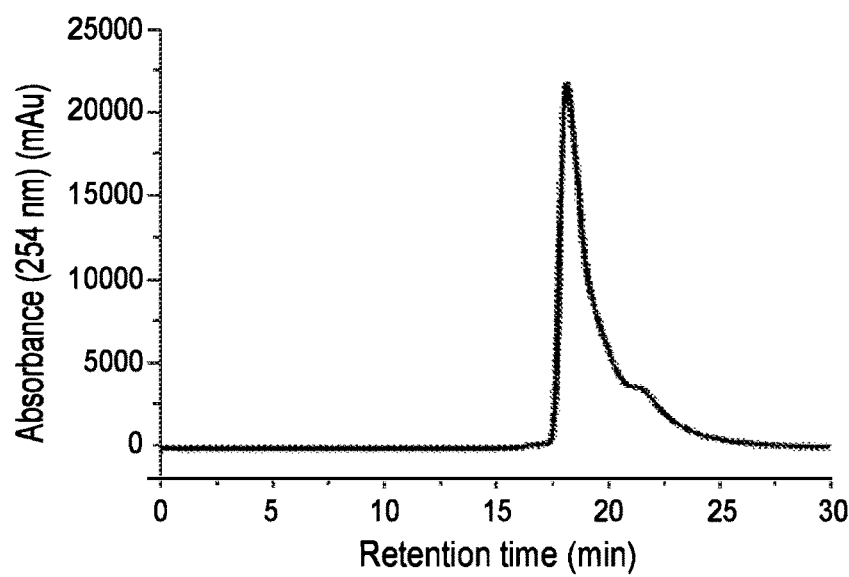
Figure 6C:
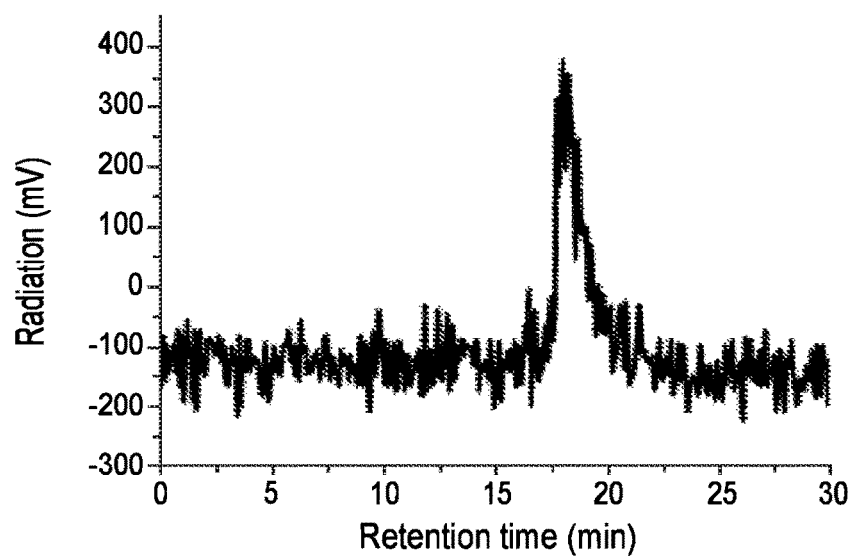

The UV-Vis chromatograms (at two different absorption wavelengths of 280 and 254 nm) and the radiation chromatogram (obtained using a Geiger counter as the detector) of the control are shown in FIG. 6.

Figure 7A:
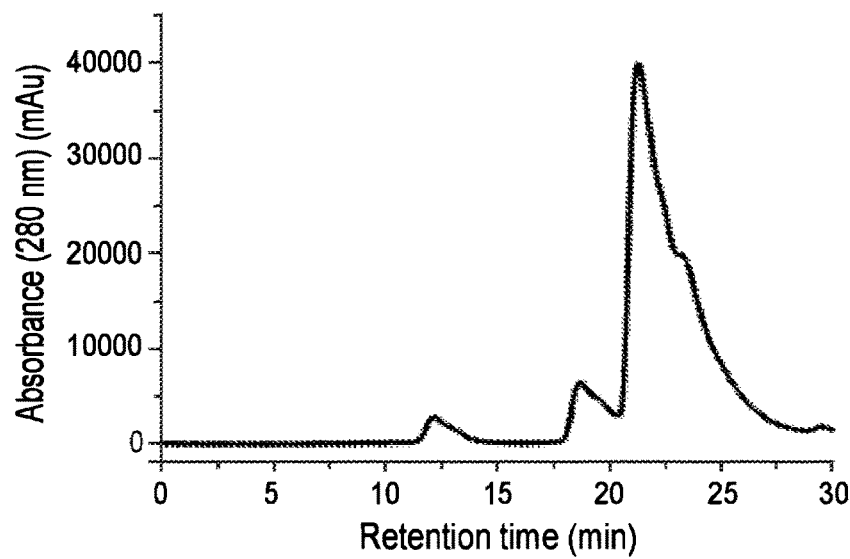
FIGS. 7A-7C. Two Size Exclusion HPLC UV-Vis chromatograms (at two different absorption wavelengths of 280 (FIG. 7A) and 254 nm (FIG. 7B)) and a radiation chromatogram (FIG. 7C) of the $^{89}$Zr DFOSq complex (78 hours after addition of $^{89}$Zr).
Figure 7B:
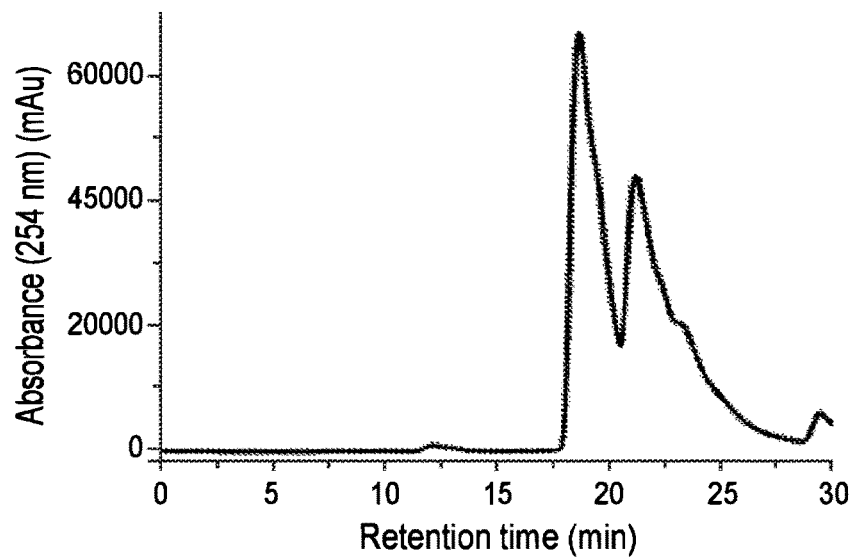
Figure 7C:
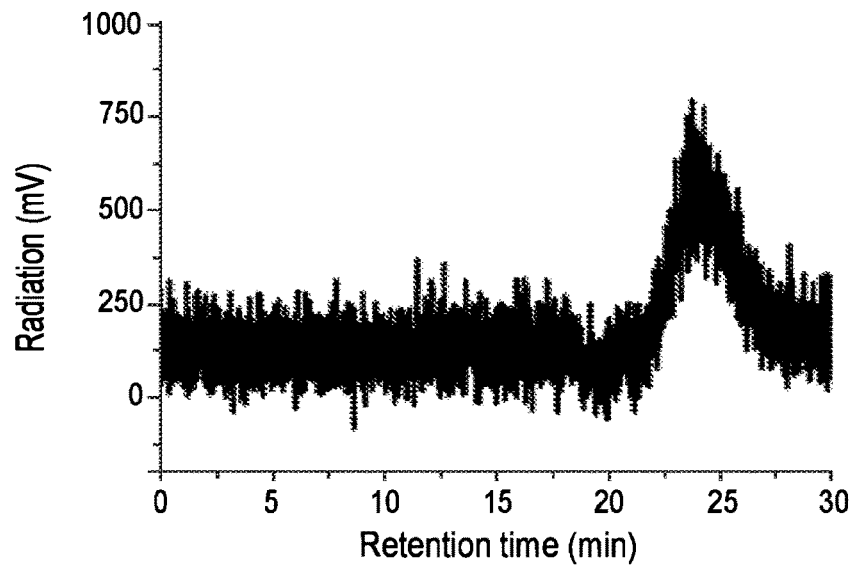

The UV-Vis chromatograms and the radiation chromatogram of the $^{89}$Zr DFOSq complex (78 hours after addition of $^{89}$Zr) are shown in FIG. 7.

Synthesis and Analysis of $^{89}$Zr DFOSq-cRGDfK

A solution of DFOSq (5 mg, 7 µmol) in DMSO (35 µL) was added to cRGDfK (3 mg, 5 µmol) in pH 9 borate buffer (0.5 M, 965 µL). The reaction mixture was allowed to stand at room temperature for 5 d, then purified by semi-preparative HPLC (ProteCol C18 column) to DFOSq-cRGDfK as a white solid (0.002 g, 32%).

HRMS ESI [M+H$^+$]: 604.3196, calculated for $(C_{27}H_{42}N_9O_7)^+$: 604.3202, [M+2H$^+$]: 302.6637, calculated for $(C_{27}H43N_9O_7)_2^+$: 302.6638.

For radiolabelling, aqueous Na$_2$CO$_3$ (2 M, 4.5 µL) was added to a solution of $^{89}$Zr in 1 M oxalic acid (10 MBq, 10 µL) until the pH increased to 10. HEPES buffer (0.5 M, pH 7, 50 µL) was then added and the solution allowed to stand for 5 min. Neutral pH was confirmed, and then a solution of DFOSq-cRGDfK in H$_2$O (10 µL, 0.008 µmol) was added. After 70 min, reaction completion was confirmed by radio-iTLC (Silica infused glass fiber plate, 0.1 M pH 6 citrate buffer as eluent, product R$_f$=0).

Figure 8:
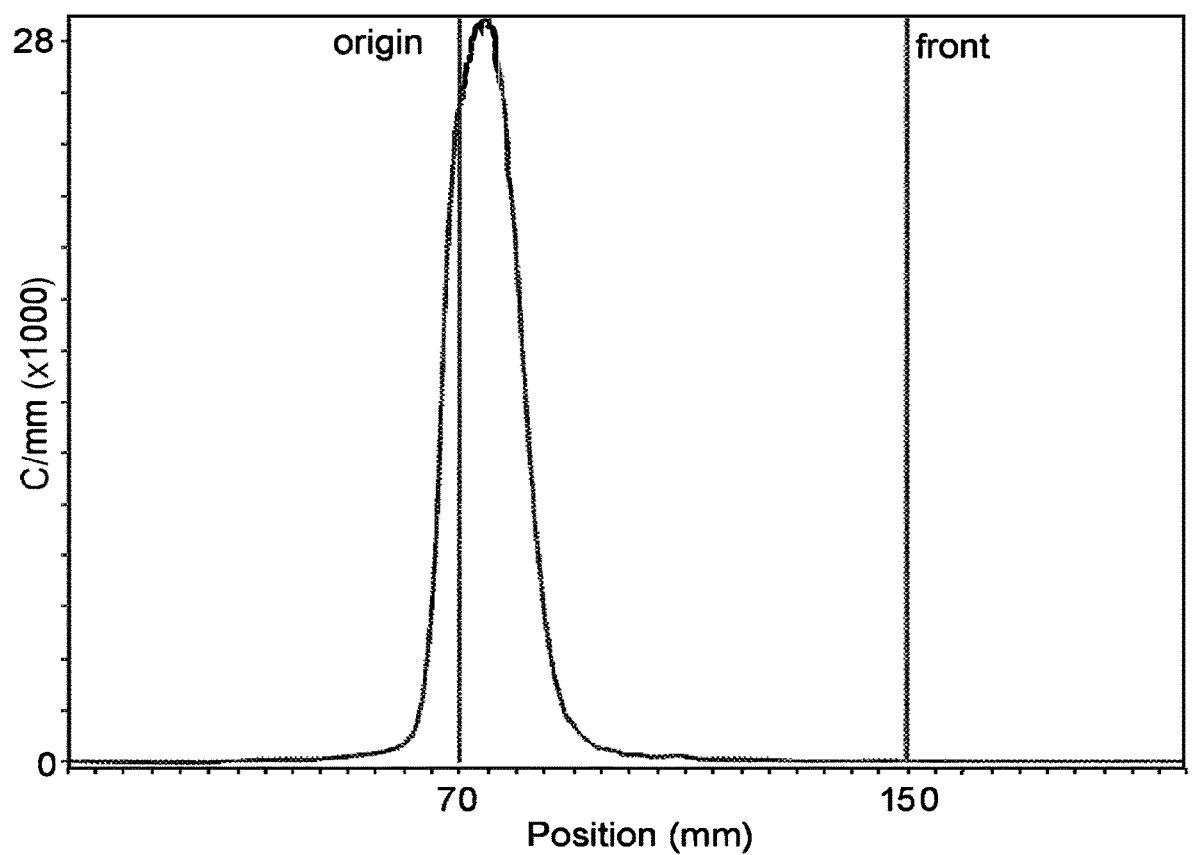
FIG. 8. A radio-iTLC chromatogram of $^{89}$Zr-labelled DFOSq-cRGDfK (taken 60 minutes after addition of $^{89}$Zr).

The radio-iTLC chromatogram of $^{89}$Zr-labelled DFOSq-cRGDfK (taken 60 minutes after addition of $^{89}$Zr) is shown in FIG. 8.

Synthesis and Analysis of $^{89}$Zr DFOSq-Transferrin

Figure 9:
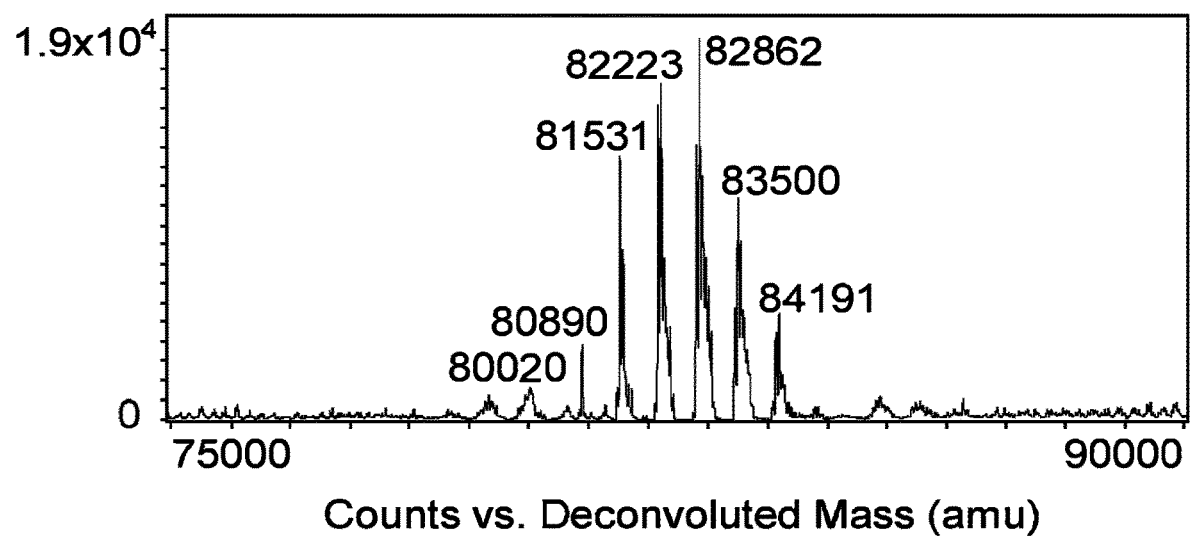
FIG. 9. An LCMS spectrum of DFOSq-transferrin (DFOSq-Tf).

A solution of DFOSq (0.17 mg, 0.25 µmol) in DMSO/H$_2$O (1:10, 26 µL) was added to a solution of human holo-transferrin (1.0 mg, 0.013 µmol) in pH 9 borate buffer (0.5 M, 974 µL). The reaction mixture was allowed to stand at room temperature for 17 h, and was then filtered using Amicon 10 kDa centrifuge filters. The crude product was washed with NaCl solution (0.9% w/v, 2×400 µL) and the concentrate collected to give DFOSq-transferrin (1.25 mg, 0.012 µmol). The product was analysed by LCMS (Agilent Poroshell C18 5 µm 2.1 75 mm column), which indicated a mixture of transferrin (Tf) with 2-8 chelators, and an average of 4.5 chelators/protein (see FIG. 9).

For radiolabelling, aqueous Na$_2$CO$_3$ (2 M, 10 µL) was added to a solution of $^{89}$Zr in 1 M oxalic acid (1.2 MBq, 20 µL) until the pH increased to 10. HEPES buffer (0.5 M, pH 7, 30 µL) was then added and the solution allowed to stand for 5 min. Neutral pH was confirmed, and then a solution of DFOSq-Tf in 0.9% NaCl (2 µL, 100 µg) was added. After 20 min, the reaction was complete and confirmed by radio-iTLC (Silica infused glass fiber plate, 0.1 M pH 6 citrate buffer as eluent, product Rf=0) and SEHPLC (BioSuite 125, 5 µm HR SEC 7.8×300 mm column, 20 mM pH 7 Dulbecco's PBS with 5% iPrOH as eluent, product retention time 12.56 min).

Figure 10:
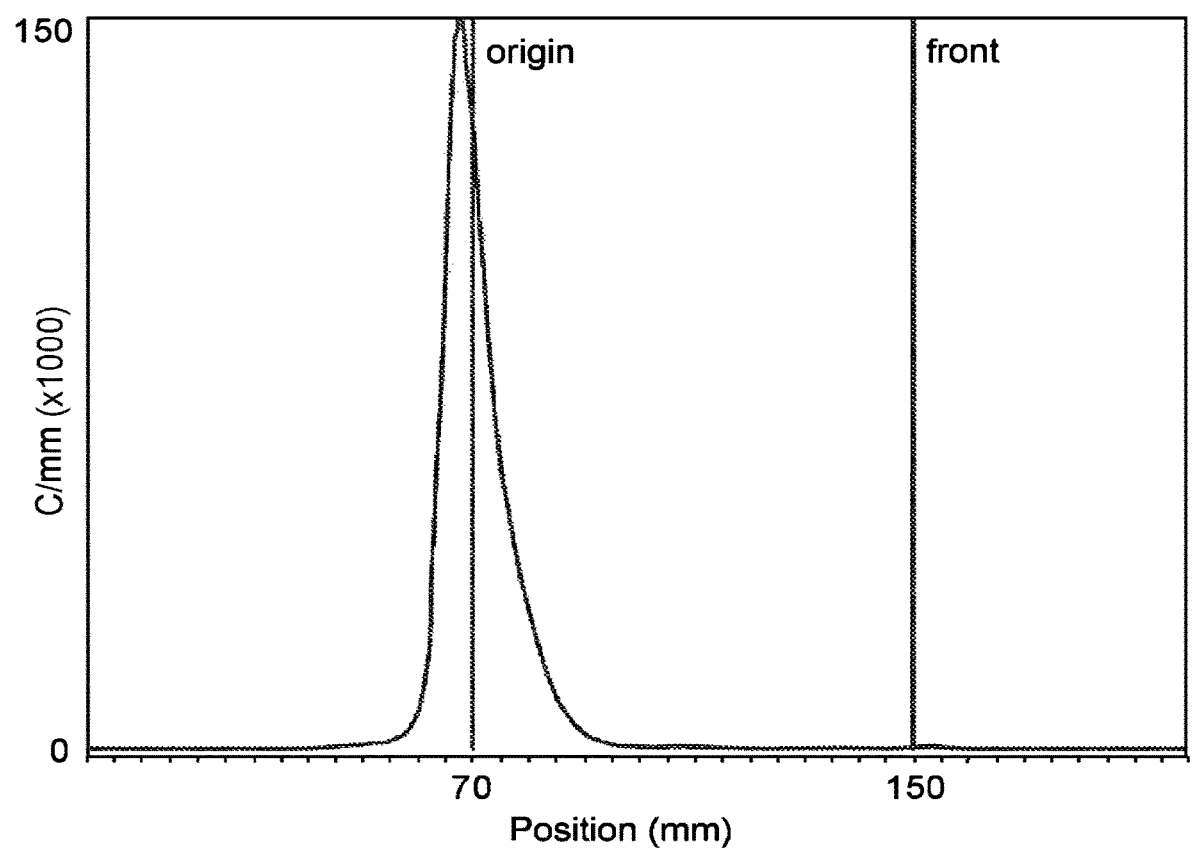
FIG. 10. A radio-iTLC chromatogram of $^{89}$Zr-labelled DFOSq-Tf (taken 20 minutes after addition of $^{89}$Zr).

The radio-iTLC chromatogram of $^{89}$Zr-labelled DFOSq-Tf (taken 20 minutes after addition of $^{89}$Zr) is shown in FIG. 10.

Figure 11A:
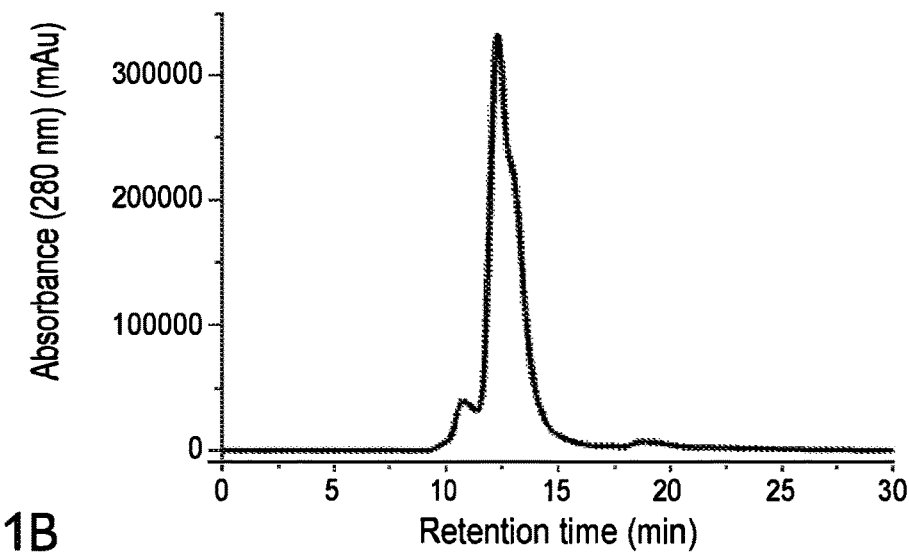
FIGS. 11A-11C. Two Size Exclusion HPLC UV-Vis chromatograms (at two different absorption wavelengths of 280 (FIG. 11A) and 254 nm (FIG. 11B)) and a radiation chromatogram (FIG. 11C) of $^{89}$Zr-labelled DFOSq-Tf (20 minutes after addition of $^{89}$Zr).
Figure 11B:
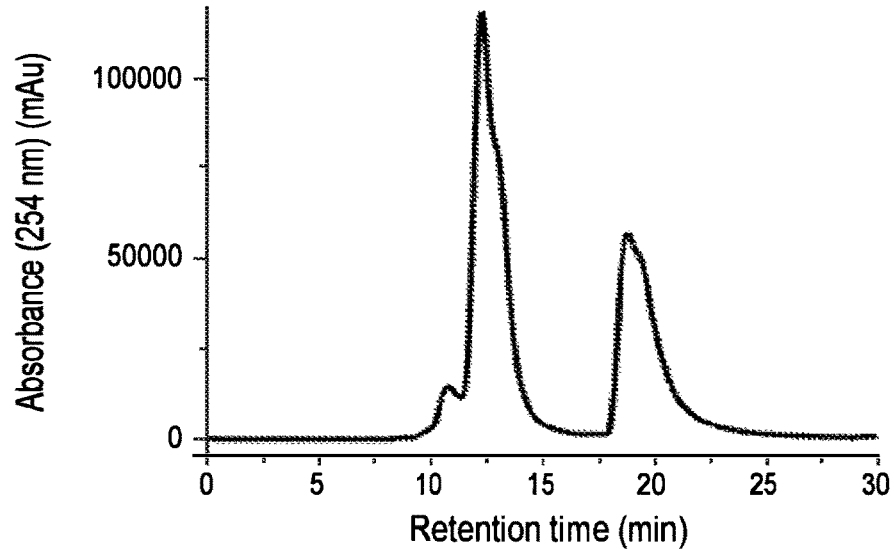
Figure 11C:
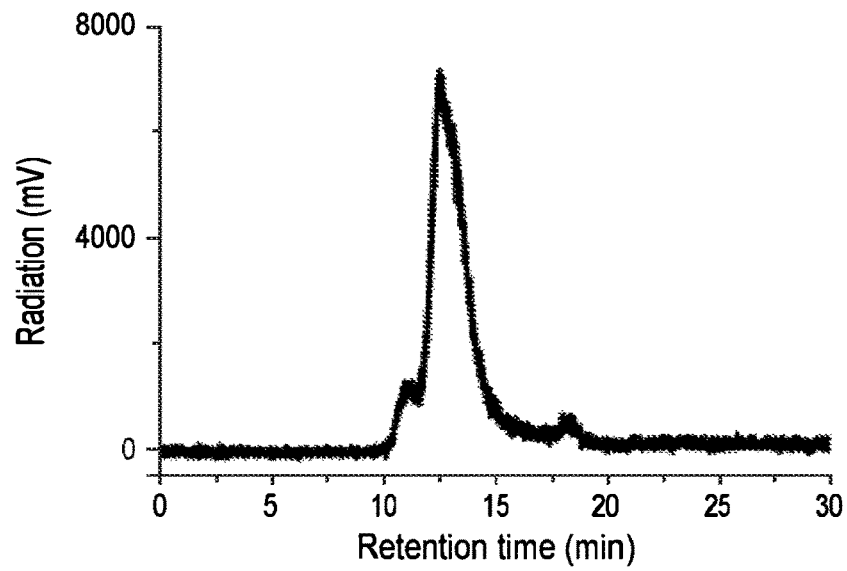

The UV-Vis chromatograms and the radiation chromatogram of $^{89}$Zr-labelled DFOSq-Tf (20 minutes after addition of $^{89}$Zr) are shown in FIG. 11.

Synthesis and Analysis of $^{89}$Zr DFOSq-Herceptin in BT474 Tumour-Bearing Mice—Study 1

Figure 12:
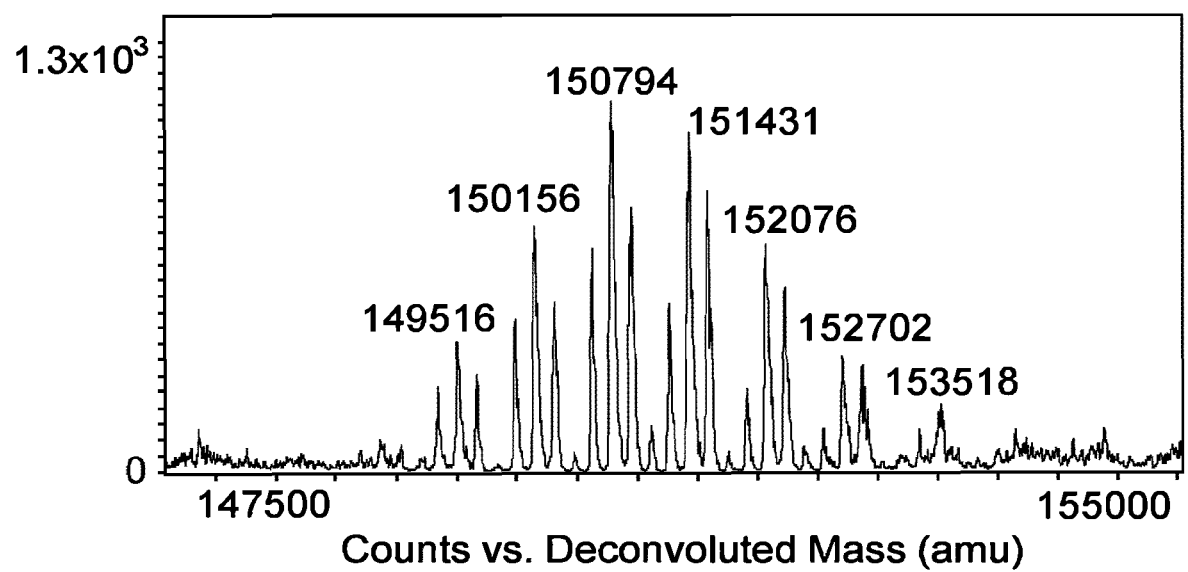
FIG. 12. An LCMS spectrum of DFOSq-herceptin (DFOSq-Herc).

A solution of DFOSq (0.46 mg, 0.67 µmol) in DMSO/H$_2$O (1:10, 228 µL) was added to a solution of clinical grade trastuzumab (5.0 mg, 0.034 µmol), and the reaction mixture was allowed to stand at ambient temperature in pH 9 borate buffer (0.5 M, total volume 1.0 mL). After 16 h, the solution was concentrated using Amicon 50 kDa centrifuge filters. The filter was used to then wash the crude product with NaCl/DMSO solution (0.9% w/v NaCl, 5% DMSO, 4×400 µL) followed by NaCl solution (0.9% w/v, 400 µL), and the concentrate was collected to give DFOSq-herceptin (1.4 mg, 0.0093 µmol, 28%). The product was analysed by LCMS (Agilent Poroshell C18 5 µm 2.1 75 mm column), which indicated a mixture of Herceptin (Herc) with 2-7 chelators, and an average of 4.5 chelators/antibody (see FIG. 12).

For the radiolabelling, aqueous Na$_2$CO$_3$ (2 M, 25 µL) was added to a solution of $^{89}$Zr in 1 M oxalic acid (55 MBq, 75 µL) until the pH increased to 10. HEPES buffer (0.5 M, pH 7, 100 µL) was then added and the solution allowed to stand for 5 min. Neutral pH was confirmed, then a solution of DFOSq-Herc in 0.9% NaCl (4 µL, 225 µg) was added. After 25 min, the reaction completion was confirmed by radio-iTLC (Silica infused glass fiber plate, 0.1 M pH 6 citrate buffer as eluent, product R$_f$=0). The reaction mixture was purified on a PD-10 size exclusion column using pH 7 PBS (20 mM, with 5% sodium gentisate) as eluent. After column loading, flow through was discarded and the first fraction (1.5 mL, 45 MBq) was collected. The product was analysed by radio-iTLC and SEHPLC (BioSuite 125, 5 µm HR SEC 7.8×300 mm column, 20 mM pH 7 Dulbecco's PBS with 5% iPrOH as eluent, product retention time 12.55 min).

Figure 13:
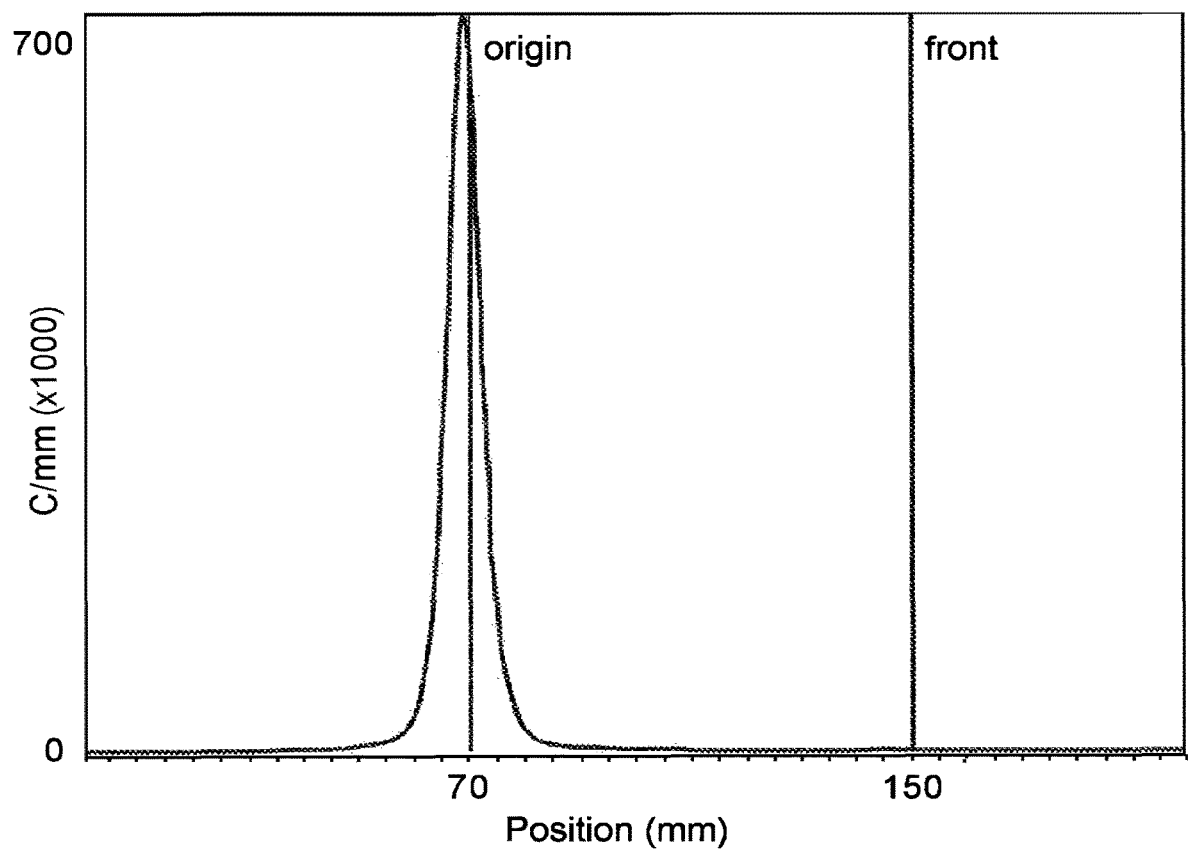
FIG. 13. A radio-iTLC chromatogram of $^{89}$Zr-labelled DFOSq-Herc (taken 25 minutes after addition of $^{89}$Zr).

The radio-iTLC chromatogram of $^{89}$Zr-labelled DFOSq-Herc (taken 25 minutes after addition of $^{89}$Zr) is shown in FIG. 13.

Figure 14:
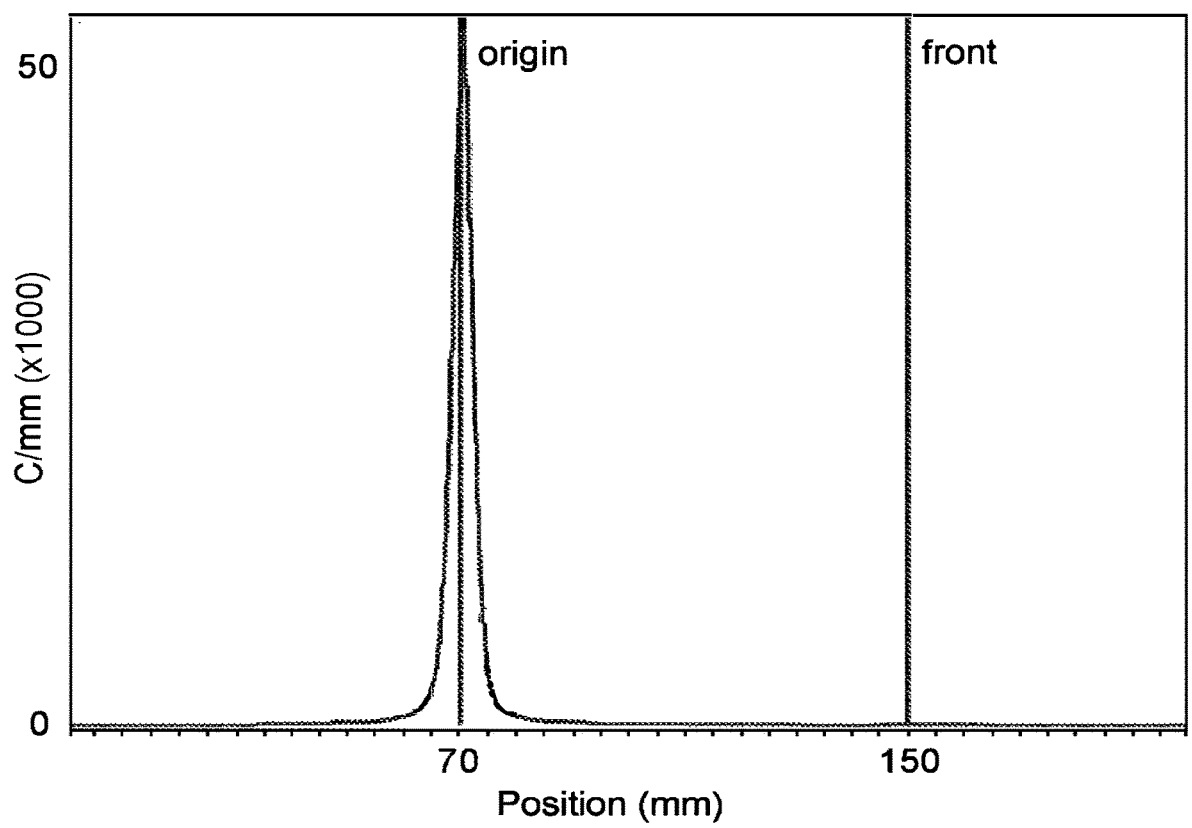
FIG. 14. A radio-iTLC chromatogram of purified $^{89}$Zr-labelled DFOSq-Herc.

The radio-iTLC chromatogram of purified $^{89}$Zr-labelled DFOSq-Herc is shown in FIG. 14.

Figure 15A:
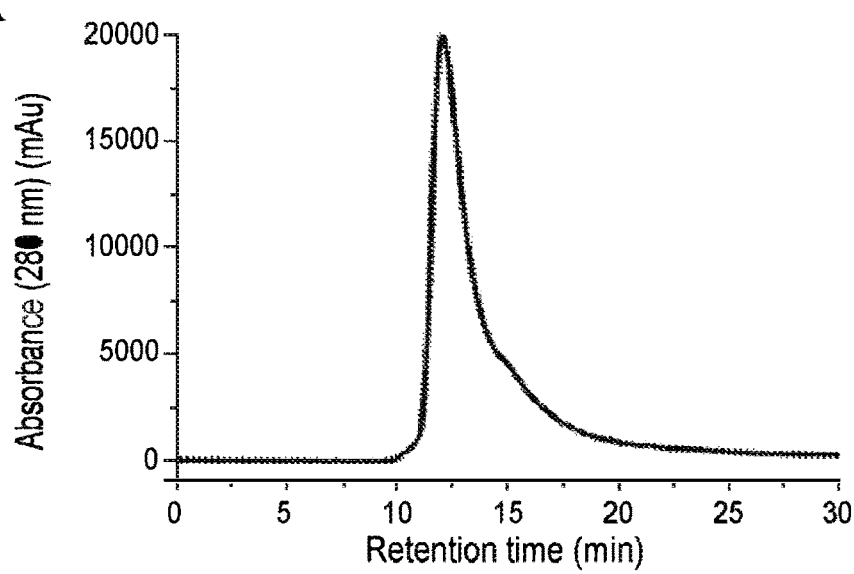
FIGS. 15A-15C. Two Size Exclusion HPLC UV-Vis chromatograms (at two different absorption wavelengths of 280 (FIG. 15A) and 254 nm (FIG. 15B)) and a radiation chromatogram (FIG. 15C) of cold (i.e. unlabelled) DFOSq-Herc.
Figure 15B:
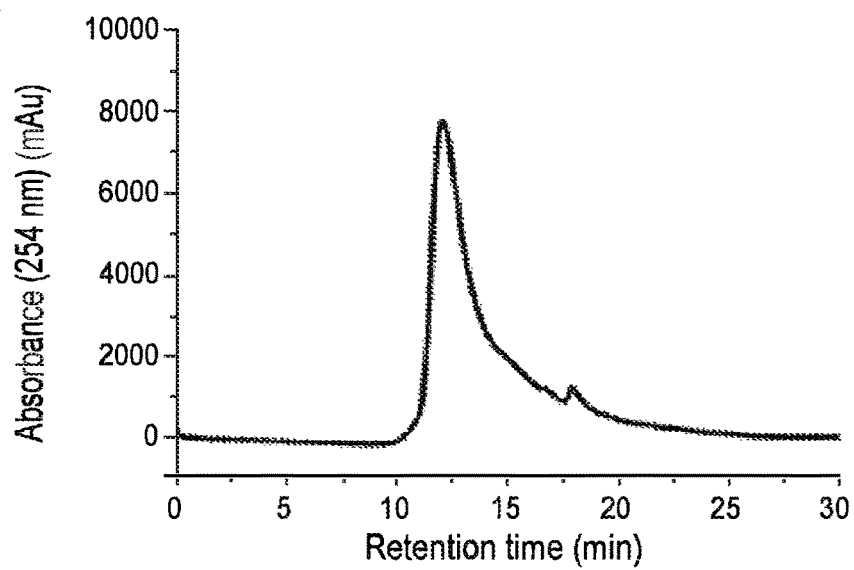
Figure 15C:
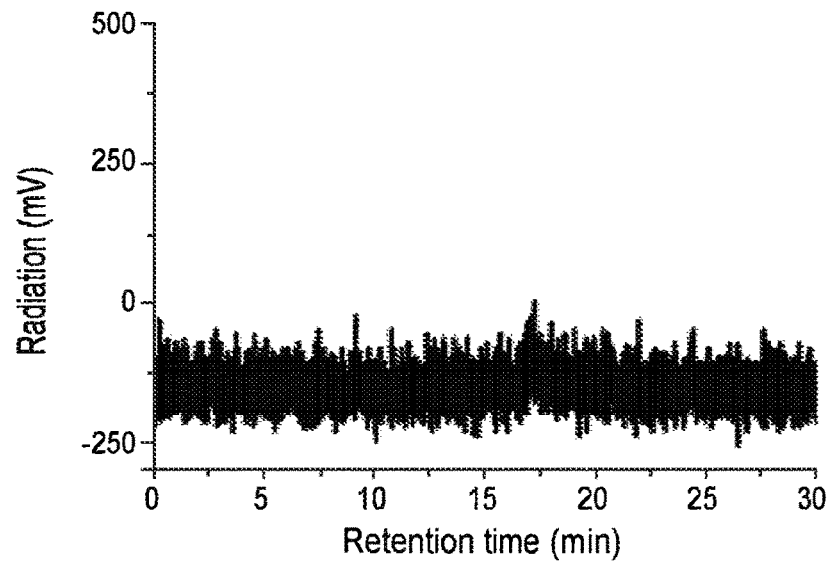

The UV-Vis chromatograms and the radiation chromatogram of cold (i.e. unlabelled) DFOSq-Herc are shown in FIG. 15.

Figure 16A:
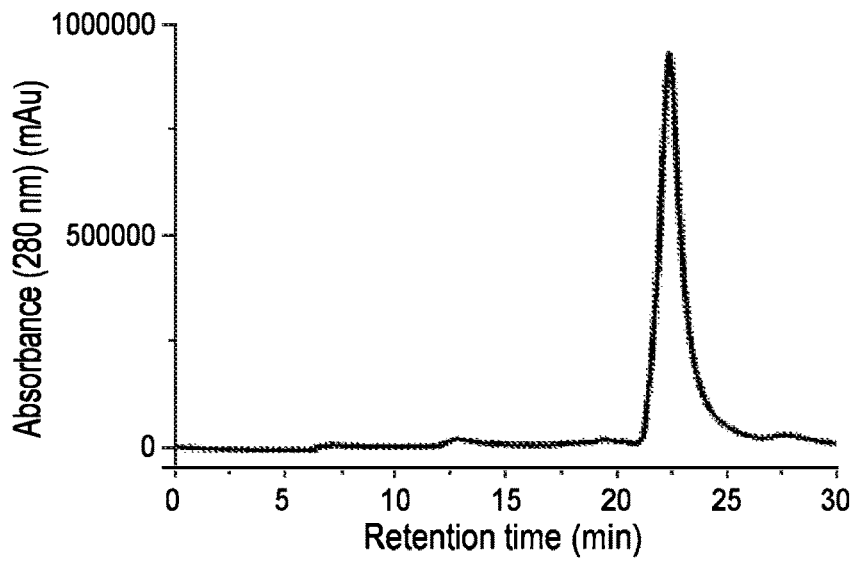
FIGS. 16A-16C. Two Size Exclusion HPLC UV-Vis chromatograms (at two different absorption wavelengths of 280 (FIG. 16A) and 254 nm (FIG. 16B)) and a radiation chromatogram (FIG. 16C) of $^{89}$Zr-labelled DFOSq-Herc (taken 24 hours after purification).
Figure 16B:
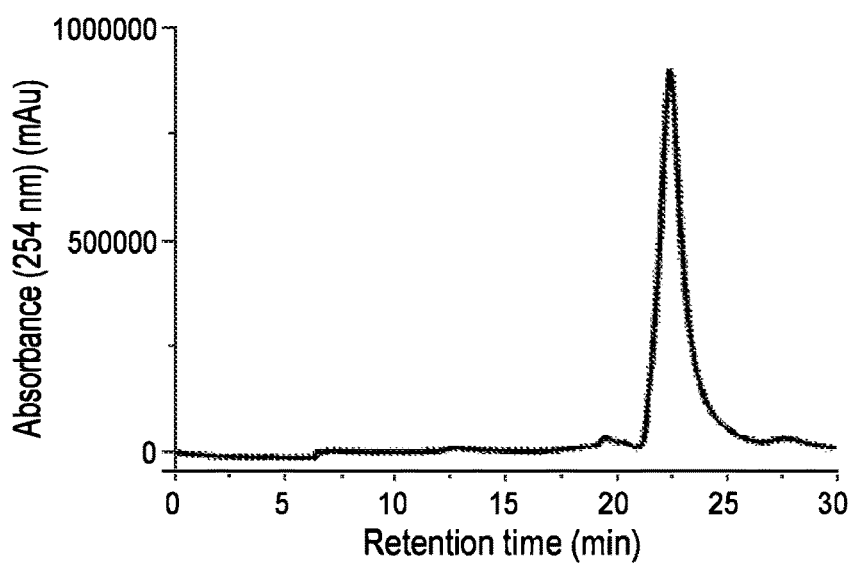
Figure 16C:
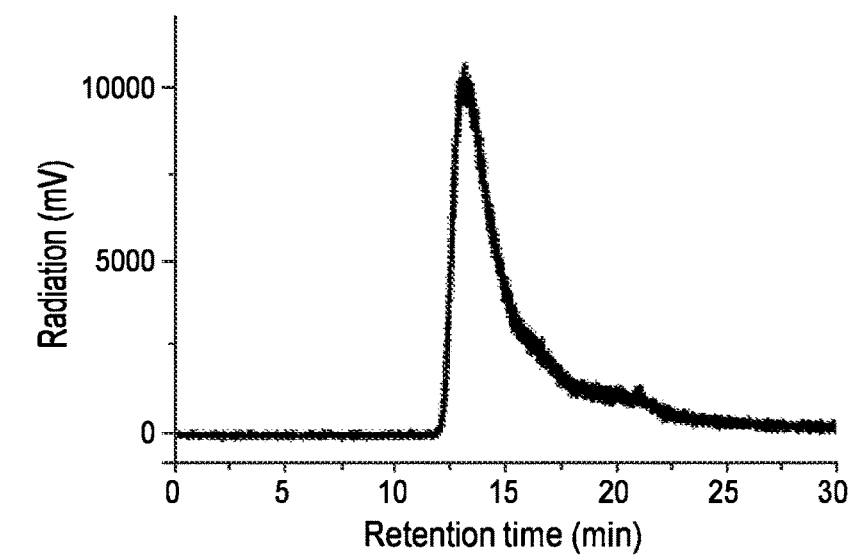

The UV-Vis chromatograms and the radiation chromatogram of $^{89}$Zr-labelled DFOSq-Herc (taken 24 hours after purification) are shown in FIG. 16.

Mouse Imaging Using $^{89}$Zr DFOSq-Herceptin

Figure 17:
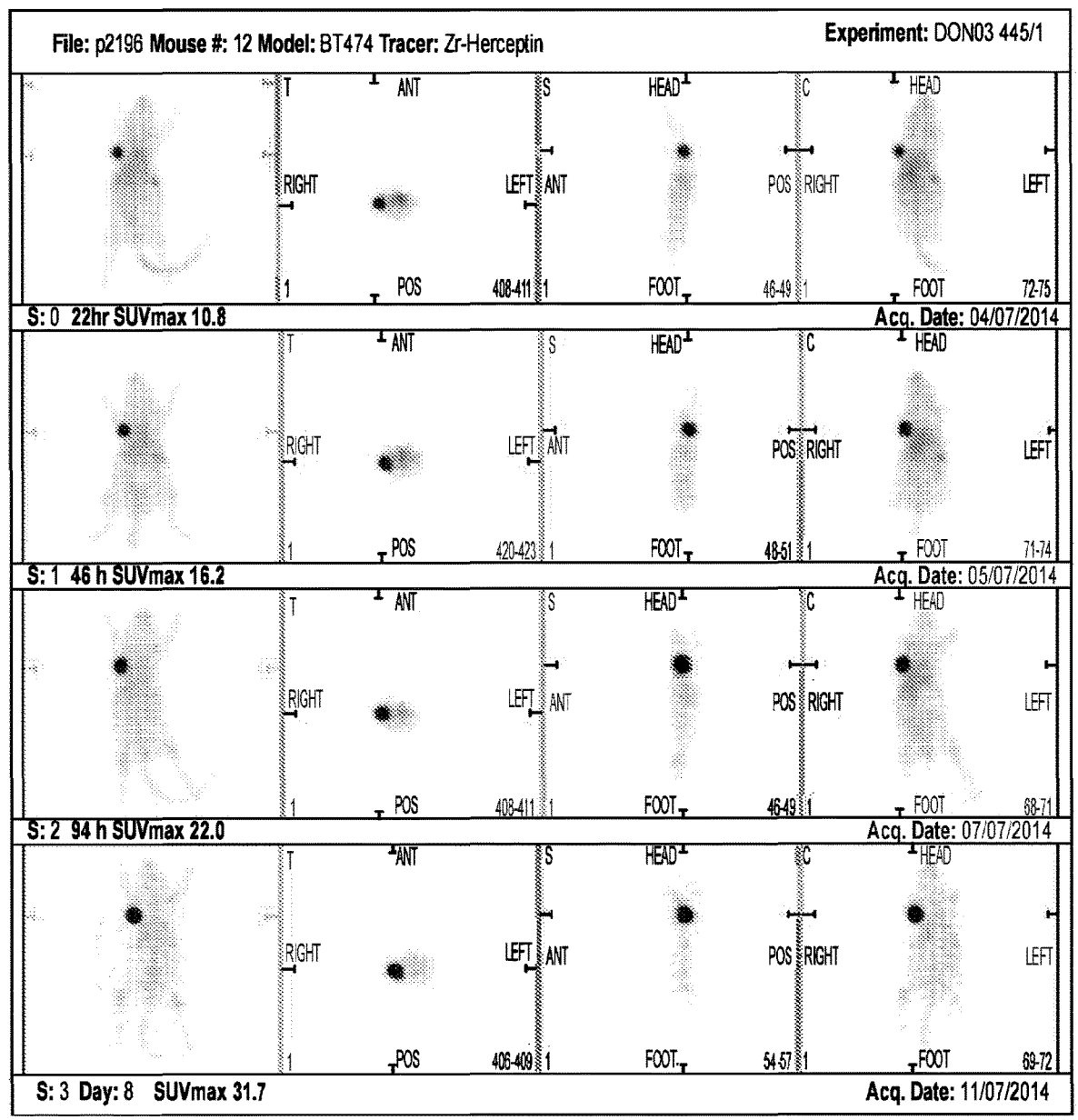
FIG. 17. PET image of mouse 1 after administration of $^{89}$ZrDFOSq-Herceptin.

Two doses of $^{89}$ZrDFOSq-Herceptin in 20 mM PBS (pH 7) with 5% sodium gentisate (200 µL, 6.0 MBq each) were prepared and administered to BT474 tumour-bearing mice via tail vein injection. PET images were taken at intervals of 22 hours, 46 hours, 94 hours and 8 days post administration (see FIGS. 17 and 18).

The table below (Table 1) sets out the standardized uptake value (SUV) for each mouse at each time point.

TABLE 1

Tumour maximum standardised uptake values (SUVs) for BT474 tumour-bearing mice using $^{89}$Zr DFOSq-herceptin

| Post administration timepoint | Mouse 1 SUV$_{max}$ | Mouse 2 SUV$_{max}$ |
|---|---|---|
| 22 h | 10.76 | 11.62 |
| 46 h | 16.17 | 16.24 |
| 94 h | 21.97 | 25.79 |
| 8 d | 31.73 | 37.21 |

A comparative study was also undertaken to compare the efficacy of a compound of the present invention (specifically, $^{89}$Zr(DFO-squarate-trastuzumab)) as a tumour imaging agent, with two other imaging agents ($^{89}$Zr(DFO-maleimide-trastuzumab) and $^9$ZrCl). The $^{89}$Zr(DFO-maleimide-trastuzumab) was prepared by dissolving a 50-fold excess of DFO-maleimide in water, and adding it to trastuzumab (Herceptin) in PBS buffer. Unreacted DFO-maleimide was removed by spin filtration and the purified conjugate was radiolabelled with $^{89}$Zr(ox)$_4$ as described above for DFO-squarate.

Mice with HER2 positive tumours were injected with two doses of a solution containing either $^{89}$Zr(DFO-squarate-trastuzumab), $^{89}$Zr(DFO-maleimide-rastuzumab) or $^{89}$ZrCl, in 20 mM PBS (pH 7) with 5% sodium gentisate (200 μL, 6.0 MBq each). PET images were taken at intervals of 22 hours, 46 hours, 94 hours and 8 days post administration in respect of the $^{89}$Zr(DFO-squarate-trastuzumab)-treated mouse, and at 24 hours for the $^{89}$Zr(DFO-maleimide-trastuzumab)- and $^{89}$ZrCl-treated mice (see FIGS. 1, 2 and 3, respectively).

Imaging Study Using $^{89}$Zr DFOSq-Herceptin in BT474 Tumour-Bearing Mice—Study 2

Trastuzumab (2 mg) was diluted in pH 9.0 borate buffer (0.5 M, 355 μL), and a solution of DFOSq in DMSO (1 mg/mL, 45 μL, 5 eq) was added. The mixture was incubated at ambient temperature for 40 h, and purified using a 50 kDa Amicon spin filter, washing with 4% DMSO in saline (3×300 μL), followed by saline only (300 uL). ESI MS analysis of the purified conjugate indicated 0-5 chelator attachments, with an average of 2 chelators/mAb. The purified DFOSq-trastuzumab solution was used immediately for radiolabelling.

$^{89}$Zr Radiolabelling of DFOSq-Trastuzumab

A solution of $^{89}$Zr in 1 M oxalic acid (150 MBq, 112 μL) was diluted with MilliQ water (250 μL) and aqueous Na$_2$CO$_3$ (2 M, 32.5 μL) was added in small portions until the pH increased to 7. HEPES buffer (0.5 M, pH 7, 120 μL) was then added and the solution allowed to stand for 5 min. DFOSq-trastuzumab in 0.9% NaCl (56 μL, 675 μg) was added. After 30 min, reaction completion was confirmed by radio-iTLC (Silica infused glass fiber plate, 0.1 M pH 6 citrate buffer as eluent, product R$_f$=0). The reaction mixture was purified on a PD-10 size exclusion column using pH 7 Dulbecco's PBS (20 mM, with 5% sodium gentisate) as eluent. After column loading, flow through was discarded and two fractions (Fraction A: 0.5 mL, Fraction B: 1.0 mL, 90.2 MBq) were collected. Fraction B was analysed by SE-HPLC (BioSuite 125, 5 μm HR SEC 7.8×300 mm column, 20 mM pH 7 Dulbecco's PBS with 5% iPrOH as eluent, product retention time ~12.5 min).

$^{89}$Zr-DFOSq-Trastuzumab: Mouse PET Imaging (BT474)

Four doses (7.5 MBq each) were drawn up from the purified mAb solution and administered to BT474 tumour bearing NOD/SCID mice. PET imaging was performed at 24, 48 and 96 hours. Mice were harvested at 96 hours for biodistribution data.

TABLE 2

Tumour maximum standardised uptake values (SUVs) for BT474 tumour-bearing mice using $^{89}$Zr-DFOSq-trastuzumab

|  | Mouse ID #3 | Mouse ID #5 | Mouse ID #6 | Mouse ID #7 |
|---|---|---|---|---|
| 24 h | 8.7 | 11.4 | 12.2 | 9.5 |
| 48 h | 11.6 | 14.4 | 12.9 | 11.0 |
| 96 h | 10.8 | 11.5 | 9.9 | 9.1 |

Synthesis, Analysis and Imaging Study of $^{89}$Zr DFOSq-Herceptin in SKOV3 or LS174T Tumour-Bearing Mice

Conjugation of DFOSq to Trastuzumab

Trastuzumab (10 mg) was diluted in pH 9.0 borate buffer (0.5 M, 1.5 mL), and a solution of DFOSq in DMSO (2 mg/mL, 455 μL, 16 eq) was added. The mixture was incubated at ambient temperature overnight, and purified using a 50 kDa Amicon spin filter, washing with 4% DMSO in saline (2×300 μL), followed by saline only (300 uL). ESI MS analysis of the purified conjugate indicated 1-6 chelator attachments with an average of 3.4 chelators/mAb. The purified DFOSq-trastuzumab solution was stored at 4° C. for 8-9 days prior to radiolabelling.

$^{89}$Zr Radiolabelling of DFOSq-Trastuzumab

A solution of $^{89}$Zr in 1 M oxalic acid (150 MBq, 195 μL) was diluted with MilliQ water (350 μL) and aqueous Na$_2$CO$_3$ (2 M, 65 μL) was added in small portions until the pH increased to 8. HEPES buffer (0.5 M, pH 7, 200 μL) was then added and the solution allowed to stand for 5 min. DFOSq-trastuzumab in 0.9% NaCl (8 μL, 675 μg) was added. After 1 h, reaction completion was confirmed by radio-iTLC (Silica infused glass fiber plate, 0.1 M pH 6 citrate buffer as eluent, product R$_f$=0). The reaction mixture was purified on a PD-10 size exclusion column using pH 7 Dulbecco's PBS (20 mM, with 5% sodium gentisate) as eluent. After column loading, flow through was discarded and the first fraction (1.0 mL, 54 MBq) was collected. The product was analysed by SEHPLC (BioSuite 125, 5 μm HR SEC 7.8×300 mm column, 20 mM pH 7 Dulbecco's PBS with 5% iPrOH as eluent, product retention time ~12.5 min).

A solution of $^{89}$Zr in 1 M oxalic acid (145 MBq, 195 μL) was diluted with MilliQ water (400 μL) and aqueous Na$_2$CO$_3$ (2 M, 75 μL) was added in small portions until the pH increased to 10. HEPES buffer (0.5 M, pH 7, 250 μL) was then added and the solution allowed to stand for 5 min. DFOSq-trastuzumab in 0.9% NaCl (8 μL, 675 μg) was added. After 1.5 h, reaction completion was confirmed by radio-iTLC (Silica infused glass fiber plate, 0.1 M pH 6 citrate buffer as eluent, product R$_f$=0). The reaction mixture was purified on a PD-10 size exclusion column using pH 7 Dulbecco's PBS (20 mM, with 5% sodium gentisate) as eluent. After column loading, 1 mL of flow through was discarded and the first fraction (1.0 mL, 47 MBq) was collected. The product was analysed by SEHPLC (BioSuite 125, 5 μm HR SEC 7.8×300 mm column, 20 mM pH 7 Dulbecco's PBS with 5% iPrOH as eluent, product retention time ~12.5 min). The signal at 11 mins is presumed to be due to antibody aggregation as a result of agitation during storage prior to radiolabelling.

$^{89}$Zr-DFOSq-Trastuzumab: Mouse PET Imaging (SKOV3)

Three doses (7.5 MBq each) were drawn up from the purified mAb solution and administered to SKOV3 tumour bearing NOD/SCID mice. PET imaging was performed at 24, 48 and 96 hours. Mice were harvested at 96 hours for biodistribution data.

TABLE 3

Tumour standardised uptake values (SUVs) for SKOV3 tumour-bearing mice using $^{89}$Zr-DFOSq-trastuzumab

|   | Mouse 1 | Mouse 2 | Mouse 4 |
|---|---------|---------|---------|
| 24 h | 5.27 | 6.32 | 4.68 |
| 48 h | 6.78 | 7.37 | 5.80 |
| 96 h | 4.87 | 7.59 | 4.97 |

TABLE 4

Biodistribution data of SKOV3 mice using $^{89}$Zr-DFOSq-trastuzumab. Values are given in % ID/g.

| Organ | Mouse ID #1 | Mouse ID #2 | Mouse ID #4 | Mean | SD | SEM |
|-------|-------------|-------------|-------------|------|-----|------|
| Blood | 1.10 | 1.78 | 0.47 | 1.12 | 0.65 | 0.33 |
| Lungs | 4.17 | 3.30 | 1.96 | 3.14 | 1.11 | 0.56 |
| Heart | 1.32 | 1.67 | 6.38 | 3.12 | 2.83 | 1.41 |
| Liver | 9.26 | 11.02 | 9.60 | 9.96 | 0.94 | 0.47 |
| Kidneys | 3.53 | 4.07 | 3.14 | 3.58 | 0.47 | 0.23 |
| Muscle | 0.55 | 0.57 | 0.34 | 0.49 | 0.13 | 0.06 |
| Spleen | 77.40 | 106.48 | 118.20 | 100.69 | 21.00 | 10.50 |
| Tumour | 15.81 | 18.26 | 12.37 | 15.48 | 2.96 | 1.48 |

$^{89}$Zr-DFOSq-trastuzumab: mouse PET imaging (LS174T)

Three doses (7.5 MBq each) were drawn up from the purified mAb solution and administered to LS174T tumour bearing BALB/c nude mice. PET imaging was performed at 24, 48 and 96 hours. Mice were harvested at 96 hours for biodistribution data.

TABLE 5

Tumour standardised uptake values for LS174T tumour-bearing mice using $^{89}$Zr-DFOSq-trastuzumab

|   | Mouse 5 | Mouse 6 | Mouse 7 |
|---|---------|---------|---------|
| 24 h | 3.10 | 3.32 | 3.07 |
| 48 h | 3.70 | 3.73 | 4.04 |
| 96 h | 4.72 | 5.32 | 5.65 |

TABLE 6

Biodistribution data of LS174T mice using $^{89}$Zr-DFOSq-trastuzumab. Values are given in % ID/g.

| Organ | Mouse ID #5 | Mouse ID #6 | Mouse ID #7 |   |   |   |
|-------|-------------|-------------|-------------|------|------|------|
| Blood | 12.82 | 12.24 | 11.49 | 12.18 | 0.66 | 0.38 |
| Lungs | 7.99 | 7.04 | 7.38 | 7.47 | 0.48 | 0.28 |
| Heart | 4.85 | 4.41 | 4.61 | 4.62 | 0.22 | 0.13 |
| Liver | 6.37 | 7.88 | 4.58 | 6.28 | 1.65 | 0.95 |
| Kidneys | 6.24 | 8.78 | 6.06 | 7.03 | 1.52 | 0.88 |
| Muscle | 1.34 | 1.37 | 1.23 | 1.31 | 0.08 | 0.04 |
| Spleen | 17.89 | 5.53 | 6.50 | 9.97 | 6.88 | 3.97 |
| Tumour | 13.11 | 12.47 | 13.67 | 13.08 | 0.60 | 0.35 |

Synthesis, Analysis and Imaging Study of $^{89}$Zr DFO-pH-NCS-Herceptin in SKOV3 Tumour-Bearing Mice Synthesis of DFOPhNCS

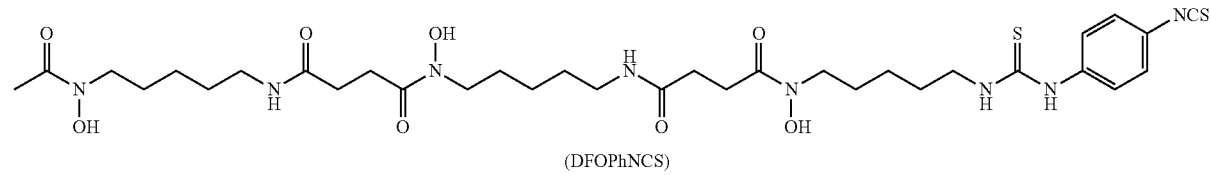

(DFOPhNCS)

Desferrioxamine (203 mg, 0.309 mmol) was stirred in iPrOH/H$_2$O (32:3 mL), and a solution of Ph(NCS)$_2$ (271 mg, 1.41 mmol) in CHCl$_3$ (20 mL) was added. Triethylamine (100 μL, 0.717 mmol) was added immediately, and the reaction mixture was stirred for 1.5 h at ambient temperature. HCl (0.1 M, 25 mL) was added and the organic layer was separated. The solvent was evaporated to give a beige solid which was triturated with CH$_2$Cl$_2$. The remaining solid was filtered off and dried to give DFOPhNCS as a white powder (207 mg, 89%). ESIMS [M+H]$^+$: 753.34, calculated for (C$_{33}$H$_{53}$N$_8$O$_8$S$_2$)$^+$: 753.34. Analytical HPLC: Method A, retention time 8.95 min. $^1$H NMR (500 MHz, dmso) δ 7.98 (s, 1H), 7.78 (s, 2H), 7.57 (d, J=8.8 Hz, 2H), 7.36 (d, J=8.9 Hz, 2H), 3.52-3.39 (m, J=13.9, 7.0 Hz, 8H), 3.00 (dd, J=12.7, 6.5 Hz, 4H), 2.61-2.54 (m, J=3.9 Hz, 4H), 2.31-2.24 (m, J=10.4, 5.4 Hz, 4H), 1.96 (s, 3H), 1.59-1.45 (m, J=22.1, 14.6, 7.3 Hz, 8H), 1.42-1.33 (m, 4H), 1.30-1.16 (m, J=18.8, 15.3, 7.1 Hz, 8H).

Conjugation of DFOPhNCS to Trastuzumab

Procedure followed directly from Vosjan, M. J. W. D.; Perk, L. R.; Visser, G. W. M.; Budde, M.; Jurek, P.; Kiefer, G. E.; van Dongen, G. A. M. S., *Nat. Protocols* 2010, 5 (4), 739-743.

Trastuzumab (3.03 mg) was diluted in saline (1 mL), and the solution adjusted to pH 9 with 0.1 M Na$_2$CO$_3$. A three-fold excess of DFOPhNCS in DMSO (2.3 mg/mL, 20 μL) was added to the mAb solution in portions with constant gentle shaking. The mixture was incubated at 37° C. at 550 rpm for 30 mins, and purified on a PD-10 column using gentisic acid (5 mg/mL)/sodium acetate (0.25 M) buffer (pH 5.5) as eluent. The purified DFOPhNCS-mAb solution was stored at −20° C. for 5 days prior to radiolabelling. ESI MS analysis of the conjugate indicated 0-1 chelator attachments, with an average of 0.2 chelators/mAb.

$^{89}$Zr Radiolabelling of DFOPhNCS-Trastuzumab

Procedure followed directly from Vosjan, M. J. W. D. et al (above).

Na$_2$CO$_3$ (2 M, 90 μL) was added to a solution of $^{89}$Zr (200 μL, 55 MBq) in oxalic acid (1 M). The mixture was incubated at ambient temperature for three minutes with gentle shaking. HEPES buffer (0.5 M, pH 7.2, 300 μL) was then added, followed by the DFOPhNCS-trastuzumab solution (710 μL), then HEPES buffer (0.5 M, pH 7.0, 700 μL). The reaction mixture was incubated at ambient temperature with frequent gentle shaking. iTLC analysis (20 mM citric acid, pH 5 as eluent) was performed at various timepoints to monitor radiolabelling progress (1 hr: 30% labelling, 1.5 hr: 53% labelling, 2 hr: % labelling).

After 2 h reaction time, the mixture was purified using a PD-10 column conditioned with fresh sodium acetate (0.25 M)/gentisic acid (5 mg/mL) buffer, pH 5-6. The purified $^{89}$Zr-DFOPhNCS-trastuzumab (1 mL, 21.8 MBq) was analysed by iTLC and SEC-HPLC.

$^{89}$Zr-DFOPhNCS-Trastuzumab: Mouse Pet Imaging SKOV3

Three doses (3.5 MBq each) were drawn up from the purified mAb solution and administered to SKOV3 tumour bearing NOD/SCID mice. PET imaging was performed at 24, 48 and 96 hours. Mice were harvested at 96 hours for biodistribution data.

TABLE 7

Biodistribution data of SKOV3 mice using $^{89}$Zr-DFOPhNCS-trastuzumab

| Mouse # | Time | SUVmax | Tmax: Bav | Liverav | Tmax: Liverav | Boneav | Tmax: Boneav |
|---|---|---|---|---|---|---|---|
| 16 | 24 | 3.53 | 3.41 | 0.39 | 1.34 | 0.17 | 3.09 |
|  | 48 | 3.47 | 4.26 | 0.37 | 1.41 | 0.18 | 2.88 |
|  | 96 | 2.20 | 4.24 | 0.41 | 1.03 | 0.21 | 2.02 |
| 28 | 24 | 5.48 | 3.96 | 0.51 | 1.61 | 0.19 | 4.26 |
|  | 48 | 5.89 | 5.12 | 0.47 | 1.91 | 0.18 | 4.86 |
|  | 96 | 4.19 | 6.09 | 0.42 | 1.89 | 0.21 | 3.72 |
| 33 | 24 | 5.30 | 4.07 | 0.53 | 1.48 | 0.17 | 4.70 |
|  | 48 | 4.62 | 3.71 | 0.50 | 1.40 | 0.17 | 4.20 |
|  | 96 | 3.86 | 5.36 | 0.60 | 1.23 | 0.22 | 3.37 |

Competition Study 1

Synthesis of DFO-cRGDfK Derivatives

An aqueous solution of cRGDfK (100 uL, 2 mg, 2 μmol) was increased to pH 9 using sodium carbonate solution. A solution of DFOSq in DMSO (100 uL, 2 eq) in pH 9 borate buffer (0.5 M, 100 μL). The reaction mixture was allowed to stand at room temperature overnight, then purified by semi-preparative HPLC (ProteCol C18 column, H$_2$O/MeCN, 0.1% TFA) and freeze dried to give DFOSq-cRGDfK as a white solid. DFOPhNCS-cRGDfK was prepared from DFO-Ph-NCS using the same procedure, however due to precipitation this was centrifuged prior to purification and only the soluble material was purified. An aqueous solution of each DFO-cRGDfK derivative was prepared at equal concentrations, and this was confirmed by Fe$^{3+}$ titration using UV-Vis spectrometry (425 nm).

Competition Experiment

A solution of $^{89}$Zr (2 uL, ~2 MBq) in 1 M oxalic acid was diluted with H$_2$O (50 uL) and neutralised using 2 M Na$_2$CO$_3$ (1 uL), then buffered with pH 7.4 HEPES buffer (5 uL). A small amount of the buffered Zr solution (5 uL) was then added to each DFO-cRGDfK solution (50 uL each). After 20 mins, reaction completion was confirmed by radio-iTLC. Each sample was run on HPLC (Phenomenex Luna column) as a standard. The DFOPhNCS-cRGDfK ligand elutes at 20.1 mins, the Zr complex at 18.5 mins (FIG. 39). The DFOSq-cRGDfK ligand elutes at 18.0 mins, the Zr complex at 15.5 mins (FIG. 40). An unidentified impurity in the DFOSq-cRGDfK ligand solution also eluted at 18.0 minutes, however this did not bind Zr.

A solution of both ligands in equal concentrations (40 uL each) was prepared and thoroughly mixed, and 5 uL of the buffered Zr solution was added. The reaction mixture was analysed after 45 minutes by HPLC, and indicated the formation of exclusively the ZrDFOSq-cRGDfK complex (FIG. 41).

Competition Study 2

Synthesis of DFO-SO$_3$H Derivatives: DFOSqTaur

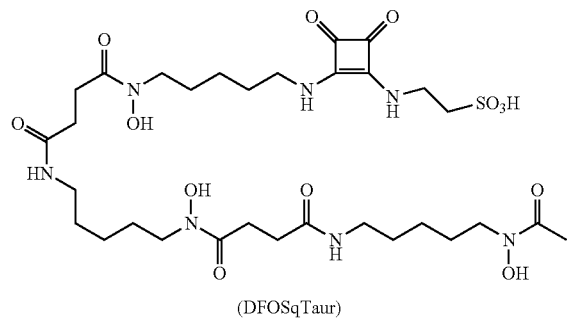 [SMILES: CC(=O)N(O)CCCCCNC(=O)CCC(=O)N(O)CCCCCNC(=O)CCC(=O)N(O)CCCCCNc1c(NCCS(=O)(=O)O)c(=O)c1=O]

(DFOSqTaur)

Figure 42:
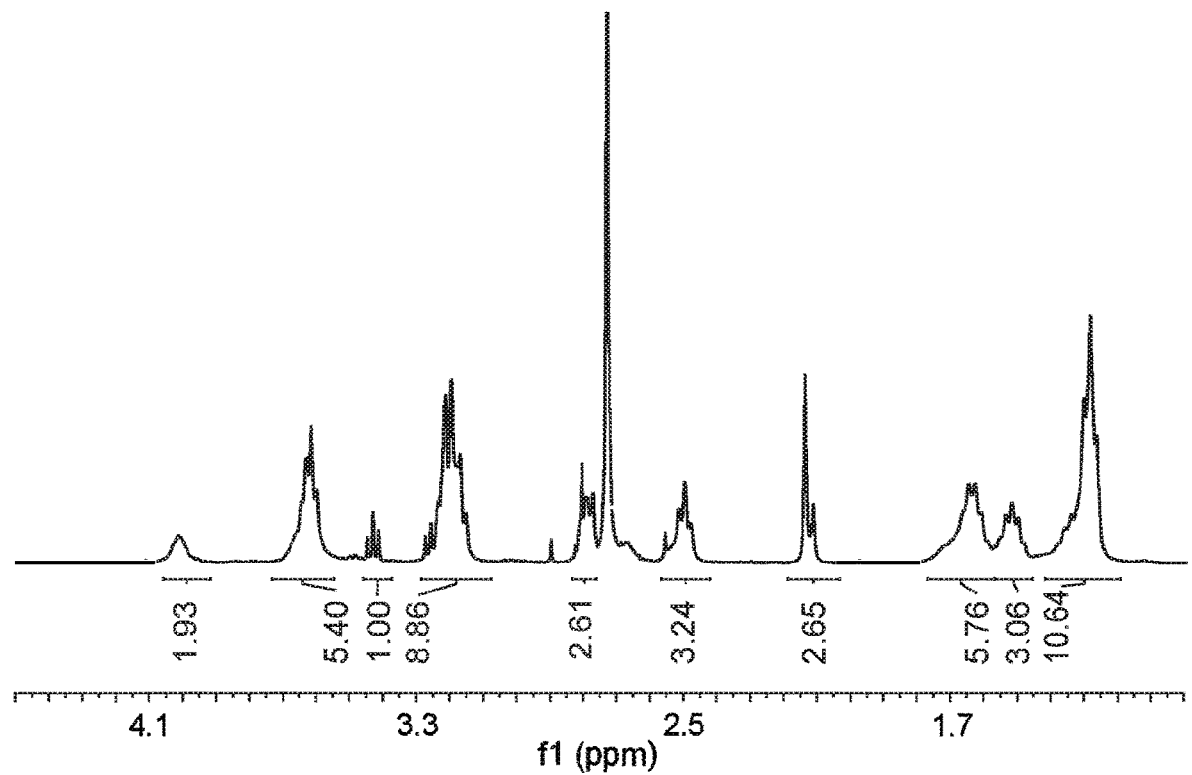
FIG. 42. $^1$H NMR (400 MHz, D$_2$O) spectrum of DFOSqTaur.
Figure 43:
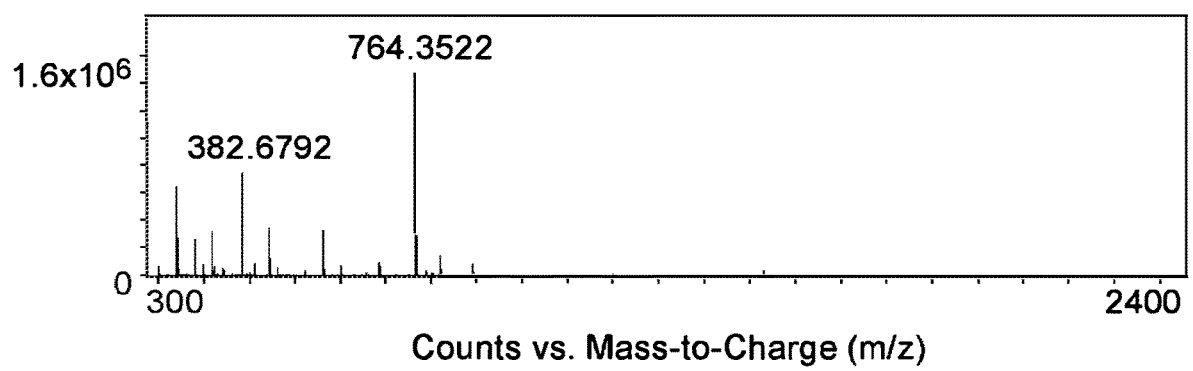
FIG. 43. ESI-MS spectrum of DFOSqTaur. [M+H]+ (calc) m/z=764.35.

A small amount of triethylamine (5 drops) was added to a solution of taurine (18 mg, 0.14 mmol) in H$_2$O. DFOSq (100 mg, 0.15 mmol) was dissolved in DMSO and added to the taurine solution, and the reaction mixture stirred at ambient temperature overnight. The solvent was evaporated and the crude material dissolved in H$_2$O with gently heating, and any unreacted DFOSq removed by centrifugation. The solvent was evaporated to give a white powder. FIGS. 42 and 43 show the $^1$H NMR and ESI-MS spectra of DFOSqTaur.

Synthesis of DFO-SO$_3$H Derivatives: DFOPhSO$_3$H

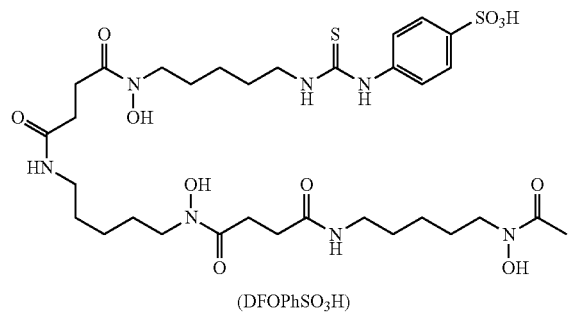 [SMILES: CC(=O)N(O)CCCCCNC(=O)CCC(=O)N(O)CCCCCNC(=O)CCC(=O)N(O)CCCCCNC(=S)Nc1ccc(S(=O)(=O)O)cc1]

(DFOPhSO$_3$H)

Figure 44:
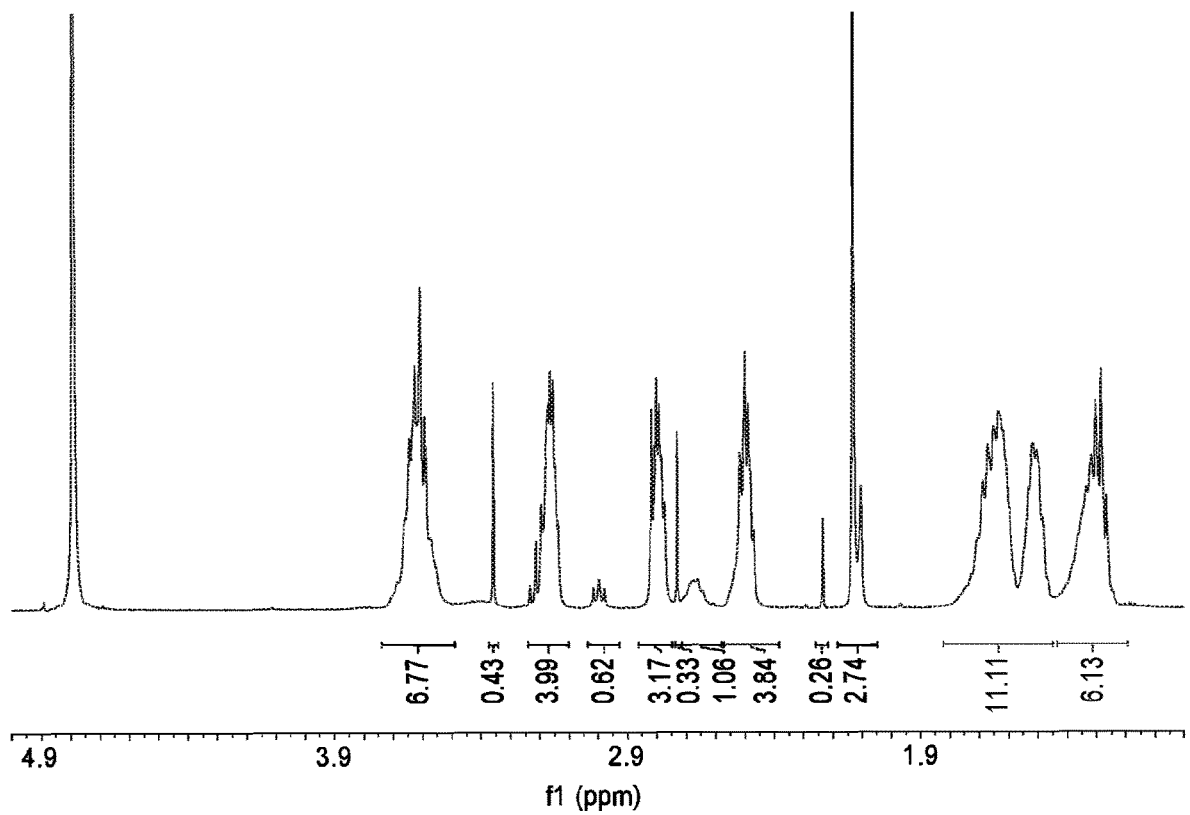
FIG. 44. $^1$H NMR (400 MHz, D$_2$O) spectrum of DFOPhSO$_3$H.
Figure 45:
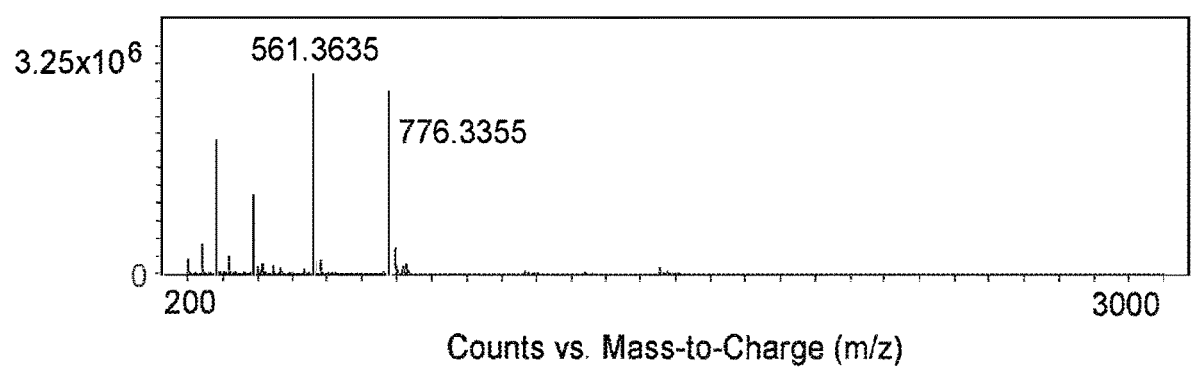
FIG. 45. ESI-MS spectrum of DFOPhSO3H. [M+H]+ (calc) m/z=776.33.

A small amount of triethylamine (5 drops) was added to a solution of 4-sulfophenyl isothiocyanate sodium salt monohydrate (38 mg, 0.15 mmol) in MeOH. DFO mesylate (100 mg, 0.15 mmol) was added to the solution, and H$_2$O (1 mL) was added to improve solubility. The reaction mixture stirred at ambient temperature overnight. The solvent was removed by evaporation, and the crude white powder washed thoroughly with MeOH at 40° C. to give the product as a white powder. FIGS. 44 and 45 show the $^1$H NMR and ESI-MS spectra of DFOPhSO$_3$H.

Competition Experiment

Figure 46:
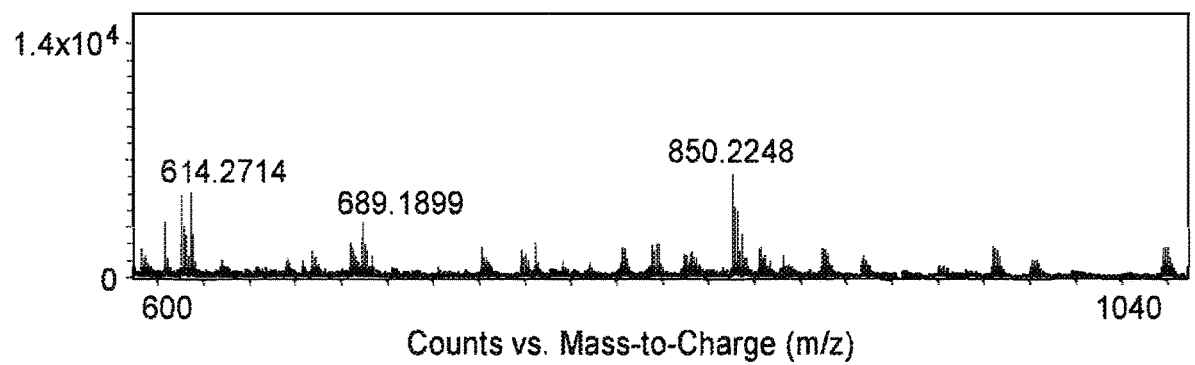
FIG. 46. ESI-MS spectrum of DFOPhSO$_3$H/DFOSqTaur/Zr reaction mixture.

A 3 mM stock solution of each ligand, DFOPhSO$_3$H and DFOSqTaur, was prepared in a mixture of H$_2$O and MeOH (concentrations were confirmed prior to dilution by UV-Vis Fe$^{3+}$ titration in H$_2$O, 430 nm). A mixture of both solutions (25 uL each) was mixed thoroughly and heated to 50° C. A stock solution of ZrCl$_4$(THF)$_2$ in H$_2$O/MeOH (3 mM) was also prepared, and 20 uL of this was added to the ligand mixture. The mixture was incubated at 50° C. for 7 hours. ESI-MS analysis of the mixture at 7 h (FIG. 46) indicated the presence of the ZrDFOSqTaur complex (FIG. 46), [M]+ m/z (calc)=850.22.

The invention claimed is:
1. A pharmaceutical composition comprising a radionuclide-labelled conjugate of:
   a compound of formula (I):

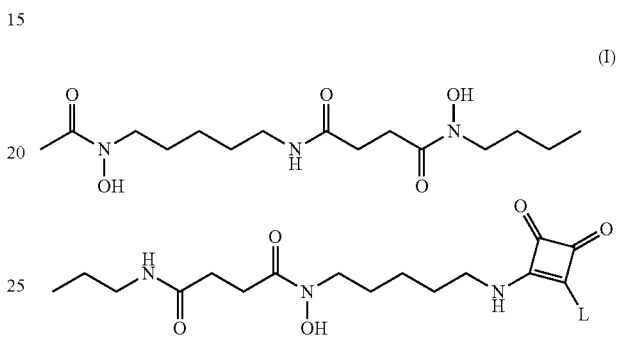

(I)

or a pharmaceutically acceptable salt thereof, wherein L is a leaving group selected from azide, halogen, cyanate, and OR, wherein R is selected from C$_1$ to C$_{10}$ alkyl, C$_1$ to C$_{10}$ heteroalkyl, C$_2$ to C$_{10}$ alkene, C$_2$ to C$_{10}$ alkyne, and aryl, each of which is optionally substituted,
   a molecule to target a tissue or tumour, and
   a radionuclide complexed thereto,
   and one or more pharmaceutically acceptable carrier substances, excipients and/or adjuvants.

2. The pharmaceutical composition of claim 1, wherein L is OR.

3. The pharmaceutical composition of claim 2, wherein R is C$_1$ to C$_6$ alkyl.

4. The pharmaceutical composition of claim 3, wherein R is methyl or ethyl.

5. The pharmaceutical composition of claim 1, wherein L is selected from O-p-toluenesulfonate, O-methanesulfonate, O-trifluoromethanesulfonate, O-benzenesulfonate, and O-m-nitrobenzenesulfonate.

6. The pharmaceutical composition of claim 1, wherein the radionuclide is selected from a radioisotope of zirconium, gallium, lutetium, holmium, scandium, titanium, indium, and niobium.

7. The pharmaceutical composition of claim 6, wherein the radionuclide is a radioisotope of zirconium, gallium or indium.

8. The pharmaceutical composition of claim 1, wherein the molecule is a polypeptide.

9. The pharmaceutical composition of claim 8, wherein the polypeptide is an antibody.

10. The pharmaceutical composition of claim 9, wherein the antibody is selected from trastuzumab, rituximab, and cetuximab.

11. The pharmaceutical composition of claim 9, wherein the antibody is selected from ranibizumab, bevacizumab, fresolimumab, panitumumab, pertuzumab, and ofatumumab.

12. The pharmaceutical composition of claim 1, wherein the molecule is a peptide.

13. The pharmaceutical composition of claim 12, wherein the peptide is a targeting peptide.

14. The pharmaceutical composition of claim 13, wherein the targeting peptide is selected from a cyclic RGD sequence, bombesin, and glu-N(CO)N-lys PSMA.

15. The pharmaceutical composition according to claim 1, wherein the composition is formulated for parenteral administration.

16. The pharmaceutical composition according to claim 1, further comprising an anti-cancer agent.

17. The pharmaceutical composition according to claim 16, wherein the anti-cancer agent is selected from: fluorouracil, imiquimod, anastrozole, axitinib, belinostat, bexarotene, bicalutamide, bortezomib, busulfan, cabazitaxel, capecitabine, carmustine, cisplatin, dabrafenib, daunorubicin hydrochloride, docetaxel, doxorubicin, eloxati, erlotinib, etoposide, exemestane, fulvestrant, methotrexate, gefitinib, gemcitabine, ifosfamide, irinotecan, ixabepilone, lanalidomide, letrozole, lomustine, megestrol acetate, temozolomide, vinorelbine, nilotinib, tamoxifen, oxaliplatin, paclitaxel, raloxifene, pemetrexed, sorafenib, thalidomide, topotecan, vermurafenib, and vincristine.

* * * * *